(12) United States Patent
Tegels et al.

(10) Patent No.: US 11,701,226 B2
(45) Date of Patent: Jul. 18, 2023

(54) PROSTHETIC HEART VALVES AND APPARATUS AND METHODS FOR DELIVERY OF SAME

(71) Applicant: Tendyne Holdings, Inc., St. Paul, MN (US)

(72) Inventors: Zachary J. Tegels, Minneapolis, MN (US); Zachary Vidlund, Robbinsdale, MN (US); Robert M. Vidlund, Forest Lake, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 301 days.

(21) Appl. No.: 17/319,136

(22) Filed: May 13, 2021

(65) Prior Publication Data

US 2021/0259837 A1 Aug. 26, 2021

Related U.S. Application Data

(63) Continuation of application No. 16/310,661, filed as application No. PCT/US2017/039972 on Jun. 29, 2017, now Pat. No. 11,090,157.

(Continued)

(51) Int. Cl.
*A61F 2/24* (2006.01)

(52) U.S. Cl.
CPC ............ *A61F 2/2436* (2013.01); *A61F 2/243* (2013.01); *A61F 2/2439* (2013.01); *A61F 2/2418* (2013.01);
(Continued)

(58) Field of Classification Search
CPC ...... A61F 2/2436; A61F 2/243; A61F 2/2439; A61F 2210/0014; A61F 2220/0075;
(Continued)

(56) References Cited

U.S. PATENT DOCUMENTS 2,697,008 A  12/1954 Ross
3,409,013 A  11/1968 Berry
(Continued)

FOREIGN PATENT DOCUMENTS

CN  1486161 A  3/2004
CN  1961845 A  5/2007
(Continued)

OTHER PUBLICATIONS

US 9,155,620 B2, 10/2015, Gross et al. (withdrawn)
(Continued)

*Primary Examiner* — Darwin P Erezo
*Assistant Examiner* — Brigid K Byrd
(74) *Attorney, Agent, or Firm* — Sleman & Lund LLP

(57) ABSTRACT

Apparatus and methods are described herein for various embodiments of a prosthetic heart valve, delivery apparatus and delivery methods for delivering a prosthetic heart valve to a heart of a patient via a transapical or transvascular delivery approach. In some embodiments, a prosthetic heart valve includes an outer frame coupled to an inner frame and the outer frame is movable between a first configuration relative to the inner frame and a second inverted configuration relative to the inner frame. The valve can be delivered to a heart using an apparatus that includes a delivery sheath that defines a lumen that can receive the prosthetic heart valve therein when the outer frame is in the inverted configuration. Actuation wires are releasably coupled to the outer frame and can be used to help revert the outer frame after the valve is deployed outside of the delivery sheath and within the heart.

19 Claims, 47 Drawing Sheets

Related U.S. Application Data

(60) Provisional application No. 62/356,828, filed on Jun. 30, 2016.

(52) U.S. Cl.
CPC ............ *A61F 2210/0014* (2013.01); *A61F 2220/0075* (2013.01); *A61F 2220/0091* (2013.01); *A61F 2230/0034* (2013.01); *A61F 2230/0093* (2013.01); *A61F 2250/0039* (2013.01); *A61F 2250/0063* (2013.01)

(58) Field of Classification Search
CPC ...... A61F 2230/0034; A61F 2002/9511; A61F 2002/9505; A61F 2/966; A61F 2002/9665
See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Frescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |

(56) References Cited

U.S. PATENT DOCUMENTS

| | | |
|---|---|---|
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |

(56) References Cited

U.S. PATENT DOCUMENTS

| | | |
|---|---|---|
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 10,327,894 B2 | 6/2019 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |

(56) References Cited

U.S. PATENT DOCUMENTS

| | | |
|---|---|---|
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0088431 A1 | 4/2007 | Bourang et al. |
| 2007/0093890 A1 | 4/2007 | Eliasen et al. |
| 2007/0100439 A1 | 5/2007 | Cangialosi et al. |
| 2007/0112355 A1 | 5/2007 | Salahieh et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0195199 A1 | 8/2008 | Kheradvar et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1* | 1/2009 | Goetz .................. A61F 2/2418 623/2.18 |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |

(56) References Cited

U.S. PATENT DOCUMENTS

| | | |
|---|---|---|
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0256754 A1 | 10/2010 | Styrc |
| 2010/0280589 A1 | 11/2010 | Styrc |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0208283 A1 | 8/2011 | Rust |
| 2011/0218619 A1 | 9/2011 | Benichou et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0123898 A1 | 5/2013 | Tung et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0197629 A1 | 8/2013 | Gainor et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243965 A1* | 8/2014 | Benson ................ A61F 2/2418 623/2.18 |
| 2014/0243966 A1 | 8/2014 | Garde et al. |
| 2014/0277419 A1 | 9/2014 | Garde et al. |
| 2014/0288639 A1 | 9/2014 | Gainor |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0343670 A1 | 11/2014 | Bakis et al. |
| 2014/0358224 A1 | 12/2014 | Tegels et al. |
| 2014/0364718 A1 | 12/2014 | Straubinger et al. |
| 2014/0364944 A1 | 12/2014 | Lutter et al. |
| 2014/0371844 A1* | 12/2014 | Dale ..................... A61F 2/2436 623/2.11 |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |

(56) References Cited

U.S. PATENT DOCUMENTS

| | | | |
|---|---|---|---|
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0007970 A1 | 1/2017 | Baruch et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0189174 A1 | 7/2017 | Braido et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2017/0325955 A1 | 11/2017 | Richter et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101686858 A | 3/2010 |
| CN | 101861134 A | 10/2010 |
| CN | 101180010 | 12/2010 |
| CN | 101984938 A | 3/2011 |
| CN | 102639179 A | 8/2012 |
| CN | 102791223 A | 11/2012 |
| CN | 102858276 A | 1/2013 |
| CN | 102869317 A | 1/2013 |
| CN | 102869318 A | 1/2013 |
| CN | 102869321 A | 1/2013 |
| CN | 103220993 A | 7/2013 |
| CN | 103826569 A | 5/2014 |
| CN | 103974674 A | 8/2014 |
| CN | 104055602 A | 9/2014 |
| CN | 105188612 A | 12/2015 |
| CN | 105208973 A | 12/2015 |
| DE | 2246526 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 | 10/2004 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2009514628 A | 4/2009 |
| JP | 2009519783 A | 5/2009 |
| JP | 2009530070 A | 8/2009 |
| JP | 2010518947 A | 6/2010 |
| JP | 2013512765 A | 4/2013 |
| JP | 2014524760 A | 9/2014 |
| JP | 2014533190 A | 12/2014 |
| NL | 1017275 C2 | 8/2002 |
| SU | 1271508 | 11/1986 |
| WO | 9217118 A1 | 10/1992 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 200041652 A1 | 7/2000 |
| WO | 200047139 A1 | 8/2000 |
| WO | 2001035878 A2 | 5/2001 |
| WO | 2001049213 A2 | 7/2001 |
| WO | 0154625 A1 | 8/2001 |
| WO | 2001054624 A1 | 8/2001 |
| WO | 2001056512 A1 | 8/2001 |
| WO | 2001061289 A1 | 8/2001 |
| WO | 0176510 A2 | 10/2001 |
| WO | 200176510 A2 | 10/2001 |
| WO | 0182840 | 11/2001 |
| WO | 2001082840 A1 | 11/2001 |
| WO | 2002004757 A1 | 1/2002 |
| WO | 0222054 A1 | 3/2002 |
| WO | 2002022054 A1 | 3/2002 |
| WO | 2002028321 A2 | 4/2002 |
| WO | 0236048 A1 | 5/2002 |
| WO | 2002041789 A2 | 5/2002 |
| WO | 0243620 A1 | 6/2002 |
| WO | 0249540 A2 | 6/2002 |
| WO | 2002043620 A1 | 6/2002 |
| WO | 2002049540 A2 | 6/2002 |
| WO | 02076348 A1 | 10/2002 |
| WO | 2003003943 A1 | 1/2003 |
| WO | 2003030776 A2 | 4/2003 |
| WO | 2003047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |

(56) References Cited

FOREIGN PATENT DOCUMENTS

| | | | |
|---|---|---|---|
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012158837 A1 | 11/2012 |
| WO | 2012177942 A2 | 12/2012 |
| WO | 2013028387 A2 | 2/2013 |
| WO | 2013045262 A1 | 4/2013 |
| WO | 2013059747 A1 | 4/2013 |
| WO | 2013028387 | 5/2013 |
| WO | 2013096411 A1 | 6/2013 |
| WO | 2013175468 A2 | 11/2013 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2014210124 A1 | 12/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

International Search Report (dated Sep. 20, 2017).
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration In Dilated Hearts," Interactive Cardiovascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
Inoue, K. et al., "Clinical Application of Transvenous Mitral Commissurotomy by a New Balloon Catheter," The Journal of Thoracic and Cardiovascular Surgery, 1984, 87:394-402.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, Georg, et al., Mitral valved stent implantation, European Journal of Cardio-Thoracic Surgery, 2010, vol. 38, pp. 350-355.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic valve," ASAIO Journal, Sep./ Oct. 1996, 42(5):M381-M385.
Orton, C., "Mitralseal: Hybrid Transcatheter Mitral Valve Replacement," Symposium: Small Animal Proceedings, 2011, pp. 311-312.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.

(56) References Cited

OTHER PUBLICATIONS

Rosch, J. et al., "The Birth, Early Years and Future of Interventional Radiology," J Vasc Interv Radiol., Jul. 2003, 4:841-853.
Ross, D. N., "Aortic Valve Surgery," Guy's Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
"Shape Memory Alloys," Retrieved from the Internet: <http://webdocs.cs.ualberta.ca/.about.database/MEMS/sma.html>, Nov. 14, 2012, 3 pages.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.
Search Report from 1st Chinese Office Action for Application No. 201780052626.9 dated Jun. 2, 2020; 4 pages.
Bernacca, G. M. et al., "Polyurethane heart valves: Fatigue failure, calcification, and polyurethane structure," Journal of Biomedical Materials Research, Mar. 5, 1997, 34(3):371-379.
Uchida, B. T. et al., "Modifications of Gianturco Expandable Wire Stents," Am. J. Roentgenol., May 1988, 150 (5):1185-1187.

* cited by examiner

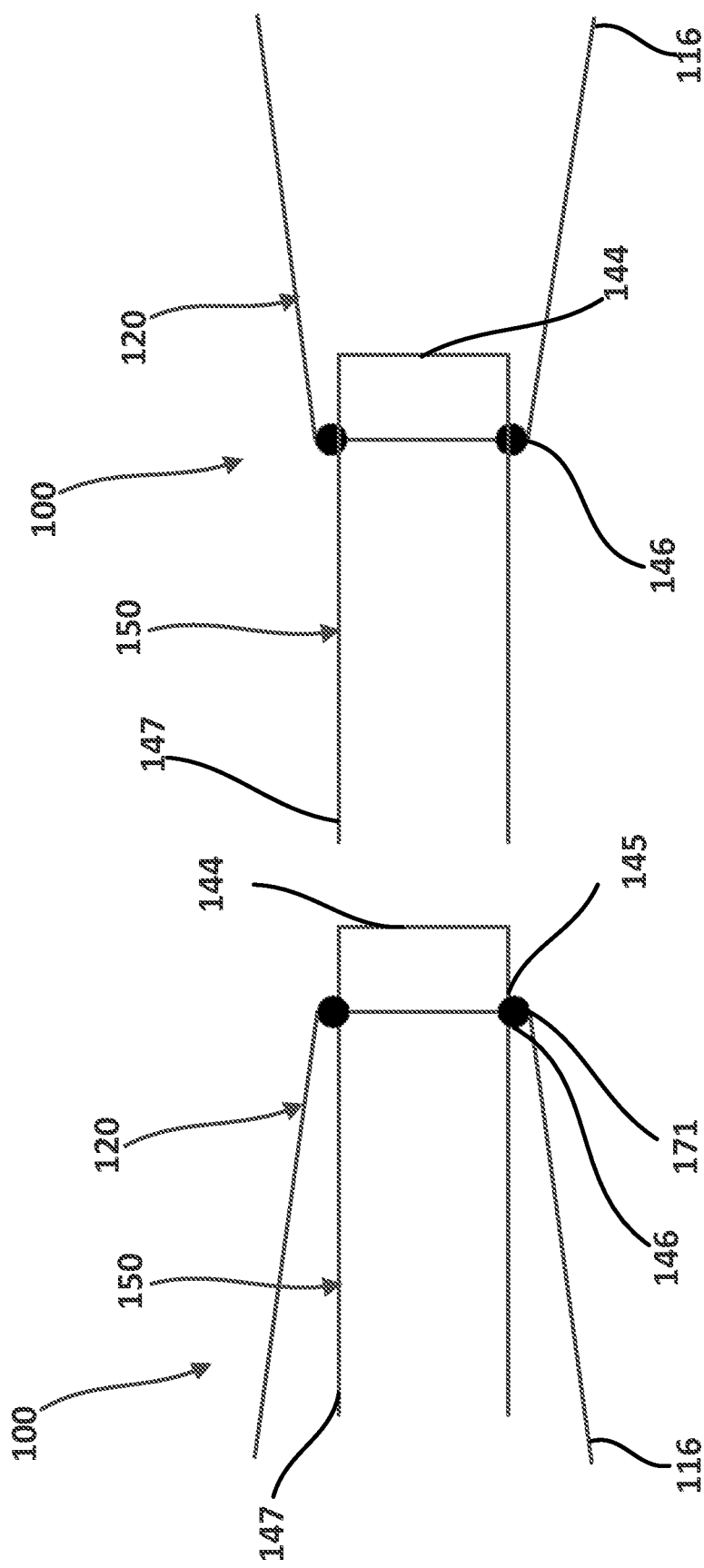

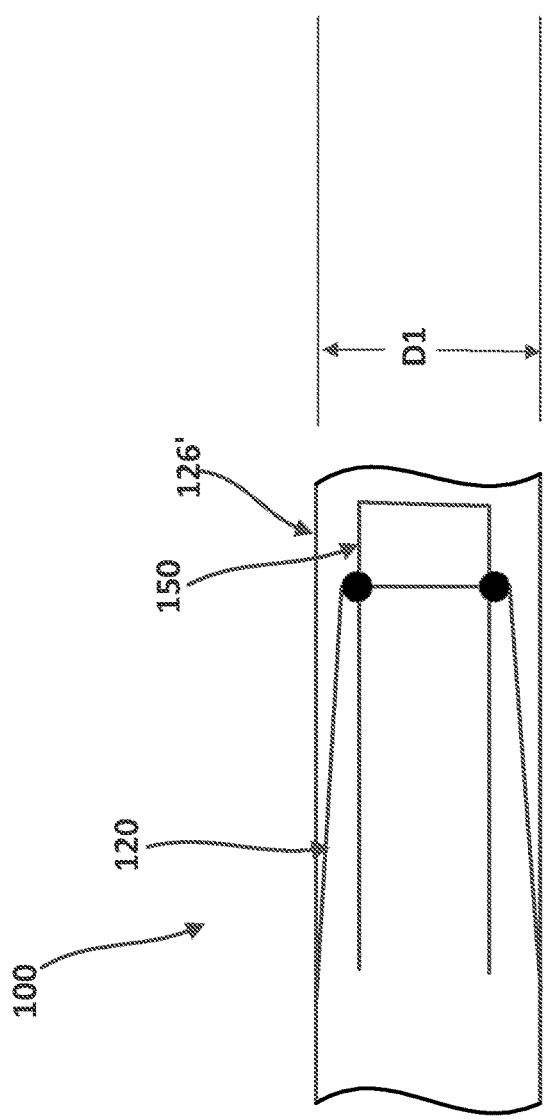
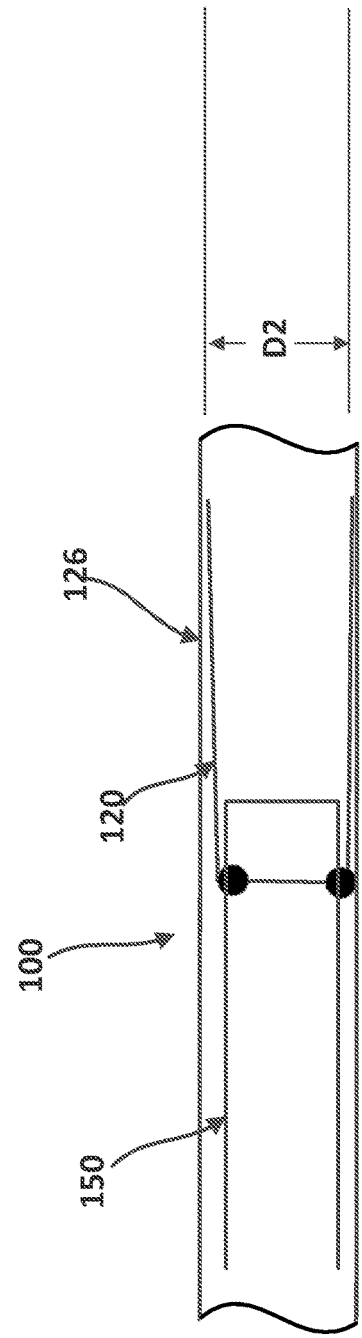
FIG. 1C
FIG. 1D

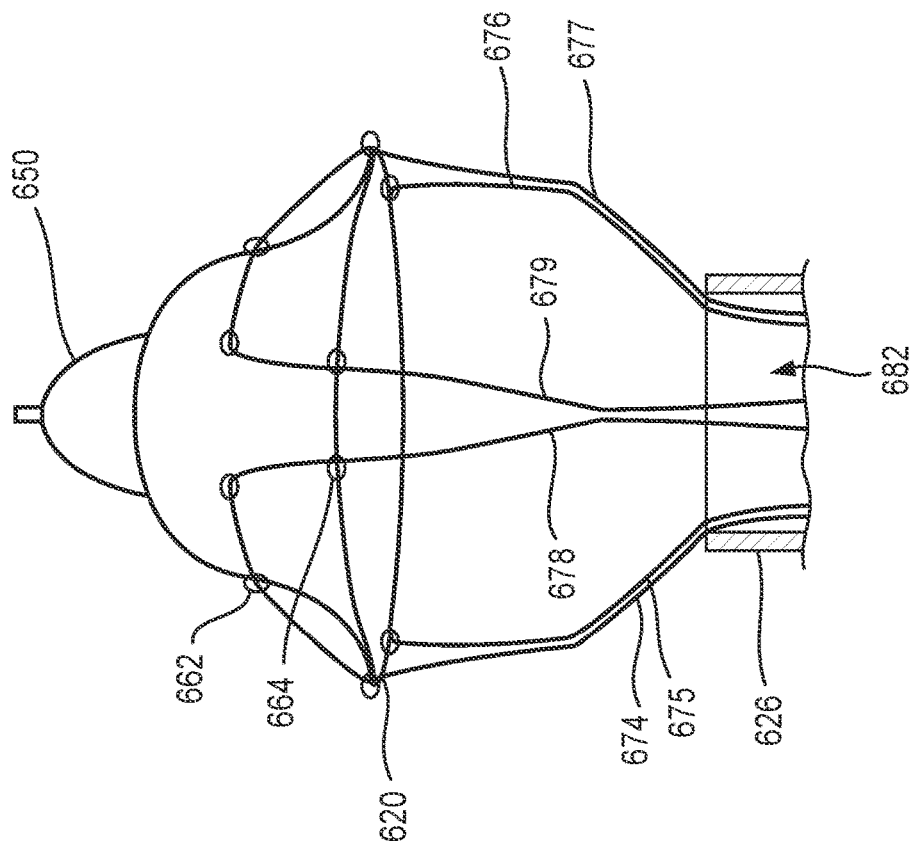
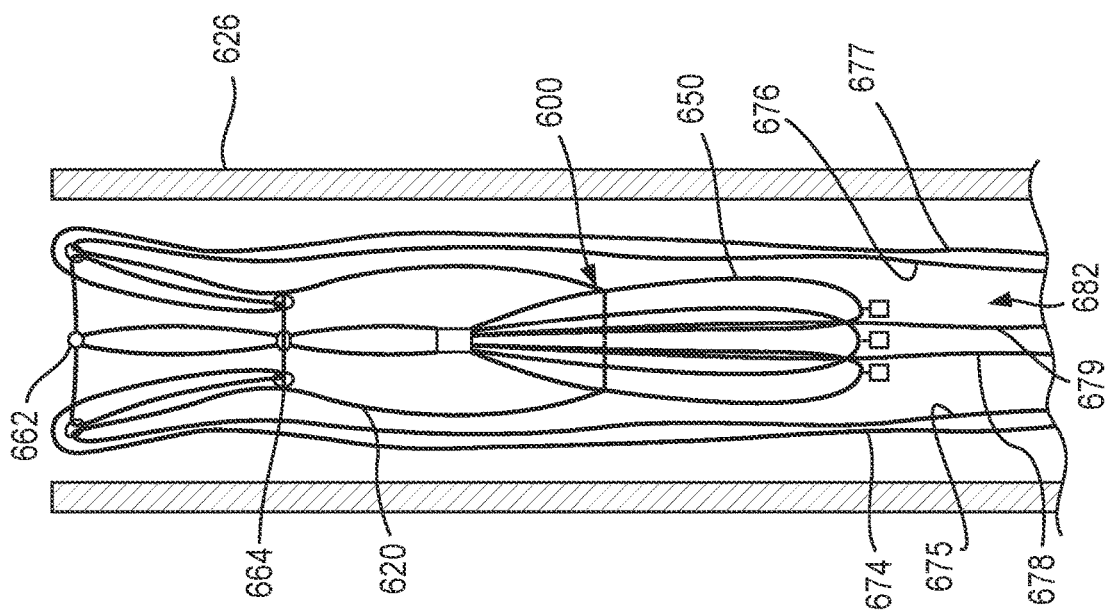

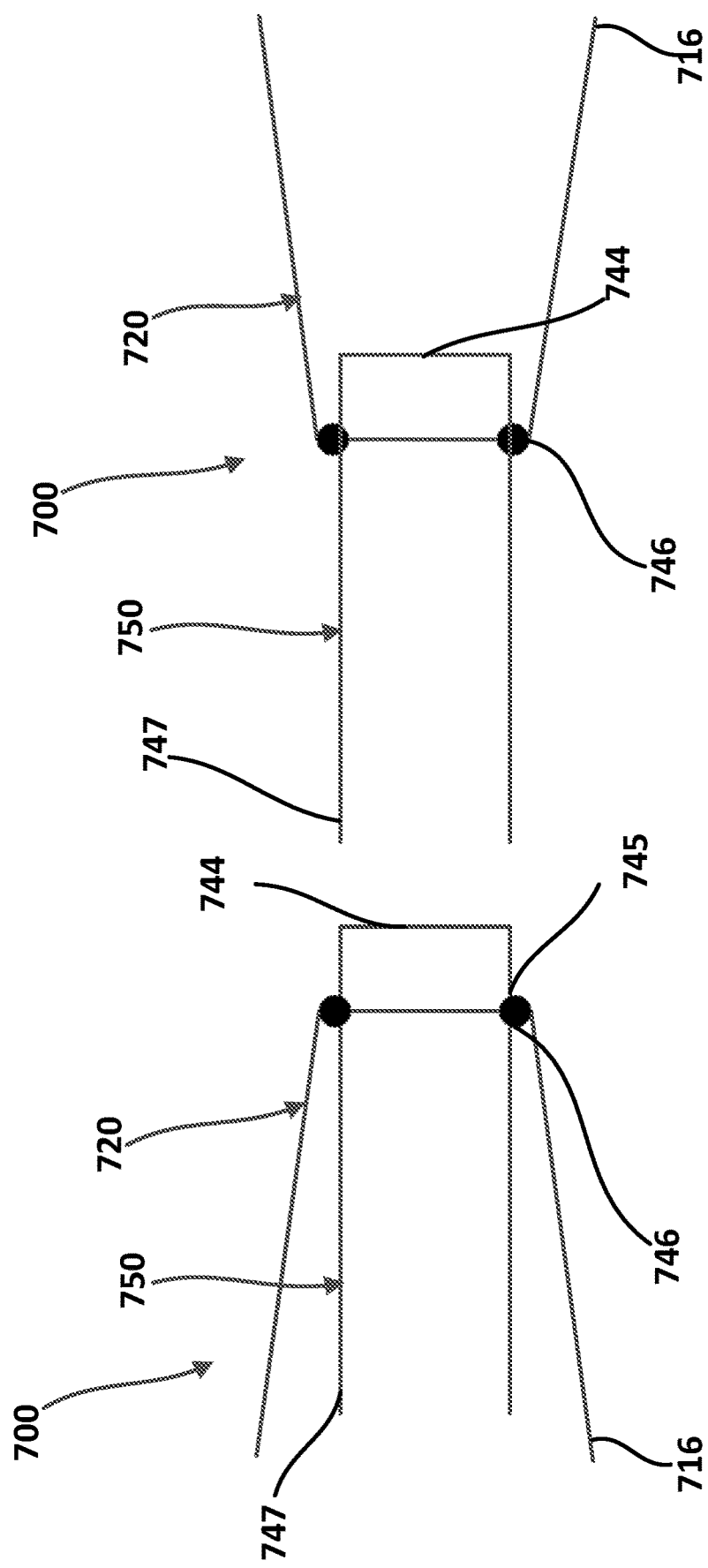

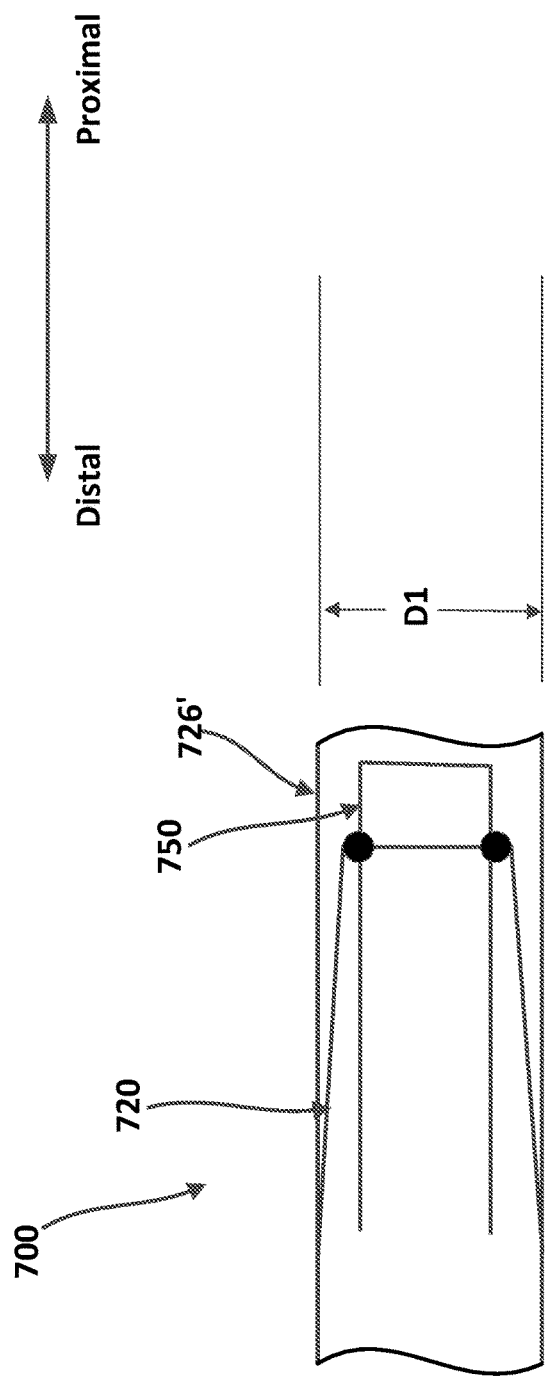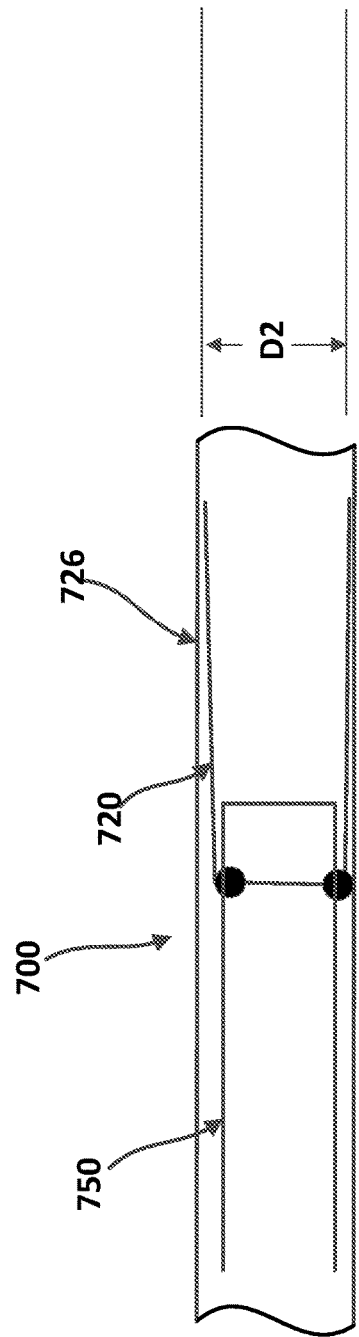

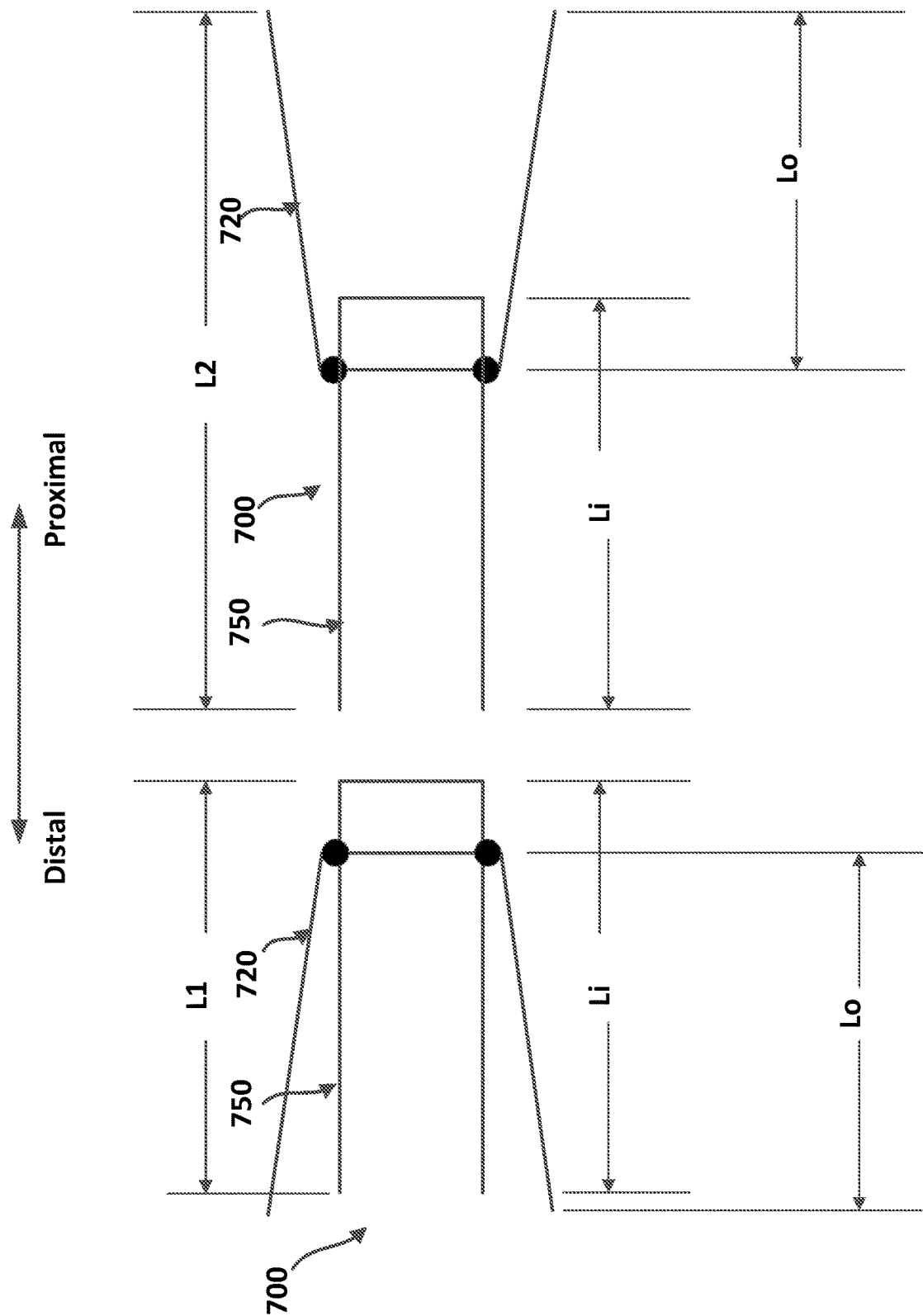

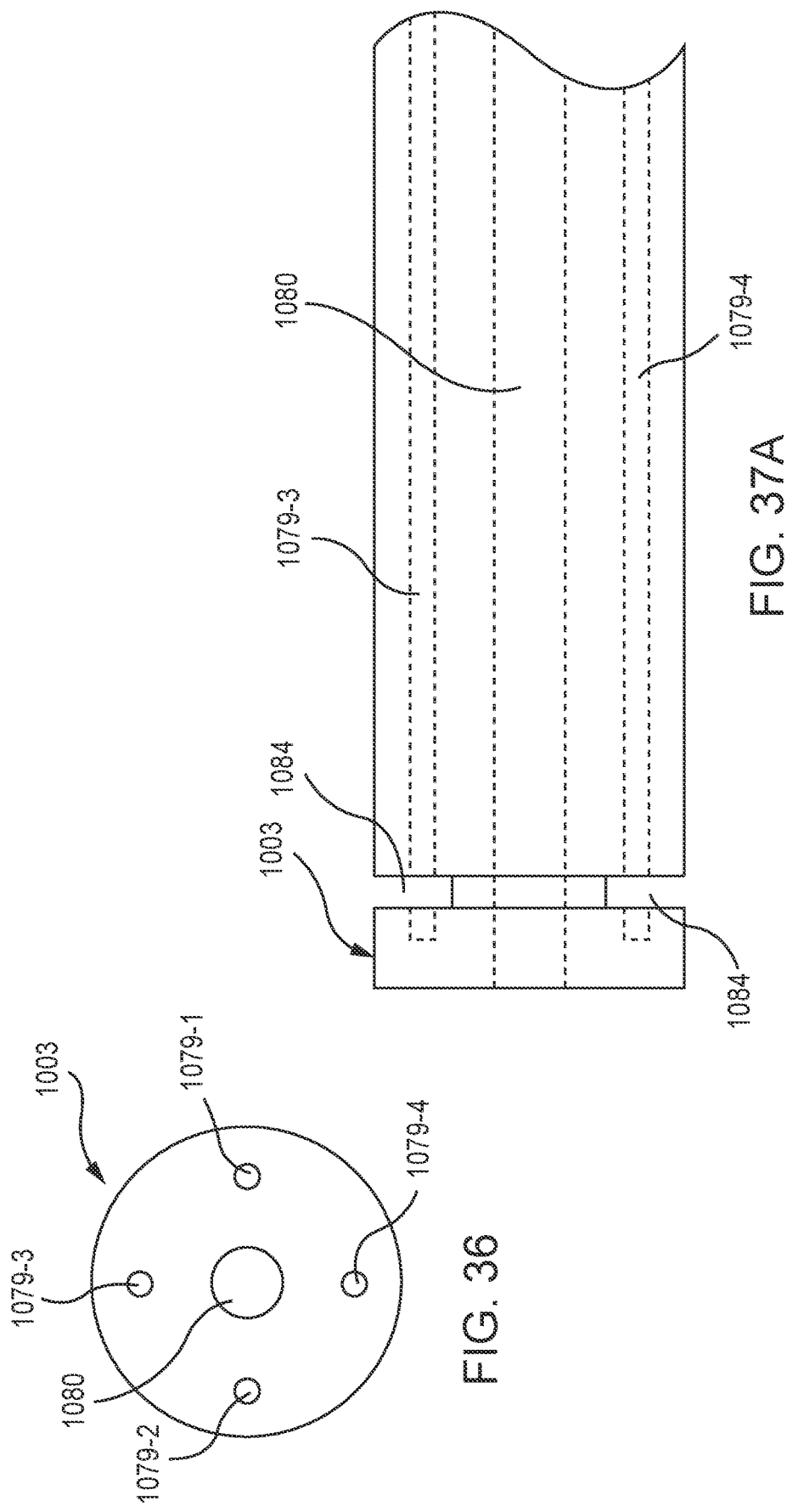

PROSTHETIC HEART VALVES AND APPARATUS AND METHODS FOR DELIVERY OF SAME

CROSS-REFERENCE TO RELATED APPLICATIONS

This application is a continuation of U.S. patent application Ser. No. 16/310,661, filed Dec. 17, 2018, which is a national phase entry under 35 U.S.C. § 371 of International Application No. PCT/US2017/039972 filed Jun. 29, 2017, published in English, which claims priority to and the benefit of U.S. Provisional Application No. 62/356,828, filed Jun. 30, 2016, entitled "Prosthetic Heart Valves and Apparatus and Methods for Delivery of Same," the disclosures of which are all incorporated herein by reference in their entireties.

BACKGROUND

Embodiments are described herein that relate to devices and methods for use in the delivery and deployment of prosthetic valves, and particularly to devices and methods for prosthetic heart valves that provide for delivery of the prosthetic heart valves to within a heart of a patient in an inverted configuration.

Prosthetic heart valves can pose particular challenges for delivery and deployment within a heart. Valvular heart disease, and specifically, aortic and mitral valve disease is a significant health issue in the United States (US); annually approximately 90,000 valve replacements are conducted in the US. Traditional valve replacement surgery involving the orthotopic replacement of a heart valve is considered an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus elimination of the extra-corporeal component of the procedure could result in reduction in morbidities and cost of valve replacement therapies could be significantly reduced.

While replacement of the aortic valve in a transcatheter manner is the subject of intense investigation, lesser attention has been focused on the mitral valve. This is in part reflective of the greater level of complexity associated to the native mitral valve apparatus, and thus, a greater level of difficulty with regards to inserting and anchoring the replacement prosthesis. A need exists for delivery devices and methods for transcatheter mitral valve replacements.

Some known delivery methods include delivering a prosthetic mitral valve through an apical puncture site. In such a procedure, the valve is placed in a compressed configuration within a lumen of a delivery catheter of, for example, 34-36 Fr (i.e. an outer diameter of about 11-12 mm). Delivery of a prosthetic valve to the atrium of the heart can be accomplished, for example, via a transfemoral approach, transatrially directly into the left atrium of the heart, a jugular approach or transapically. In many cases, it is desirable for the prosthetic valve to have a small outer perimeter or profile to allow insertion through a smaller delivery catheter of, for example, 28 Fr (i.e. an outer diameter of about 9 mm).

Thus, a need exist for prosthetic heart valves that can have a small profile during delivery while still maintaining the size and characteristics needed to perform their desired function within the heart.

A need also exists for devices and methods for delivering and deploying a prosthetic heart valve within a heart, with the valve disposed within a small diameter delivery sheath and then moving the valve to an expanded configuration within the heart.

SUMMARY

Apparatus and methods are described herein for various embodiments of a prosthetic heart valve, delivery apparatus and delivery methods for delivering a prosthetic heart valve to a heart of a patient via a transvascular and a transapical delivery approach. In some embodiments, a prosthetic heart valve includes an outer frame coupled to an inner frame and the outer frame is movable between a first configuration relative to the inner frame and a second inverted configuration relative to the inner frame. The valve can be delivered to a heart using an apparatus that includes a delivery sheath that defines a lumen that can receive the prosthetic heart valve therein when the outer frame is in the inverted configuration. Actuation wires are releasably coupled to the outer frame and can be used to help revert the outer frame after the valve is deployed outside of the delivery sheath and within the heart.

BRIEF DESCRIPTION OF THE FIGURES

FIGS. 1A and 1B are schematic illustrations of a portion of a prosthetic heart valve, according to an embodiment, shown in a first configuration and a second configuration, respectively.

FIGS. 1C and 1D are schematic illustrations of the portion of the prosthetic heart valve of FIGS. 1A and 1B, respectively, shown disposed within a delivery sheath.

FIG. 29A is a cross-sectional side view of a prosthetic heart valve in an inverted configuration inside a lumen of a delivery sheath, according to an embodiment.

FIG. 29B is a side view of the prosthetic heart valve of FIG. 9A in a reverted configuration and outside the delivery sheath.

FIGS. 30A and 30B are schematic illustrations of a portion of a prosthetic heart valve, according to an embodiment, shown in a first configuration and a second configuration, respectively.

FIGS. 30C and 30D are schematic illustrations of the portion of the prosthetic heart valve of FIGS. 30A and 30B, respectively, shown disposed within a delivery sheath.

FIGS. 31A and 31B are schematic illustrations of the portion of a prosthetic heart valve of FIGS. 30A and 30B, shown in the first configuration and the second configuration, respectively.

FIG. 36 is a proximal end view of a tube member of the delivery system of FIG. 34.

FIG. 37A is a side view of a portion of the tube member of FIG. 36.

DETAILED DESCRIPTION

Figure 2B:
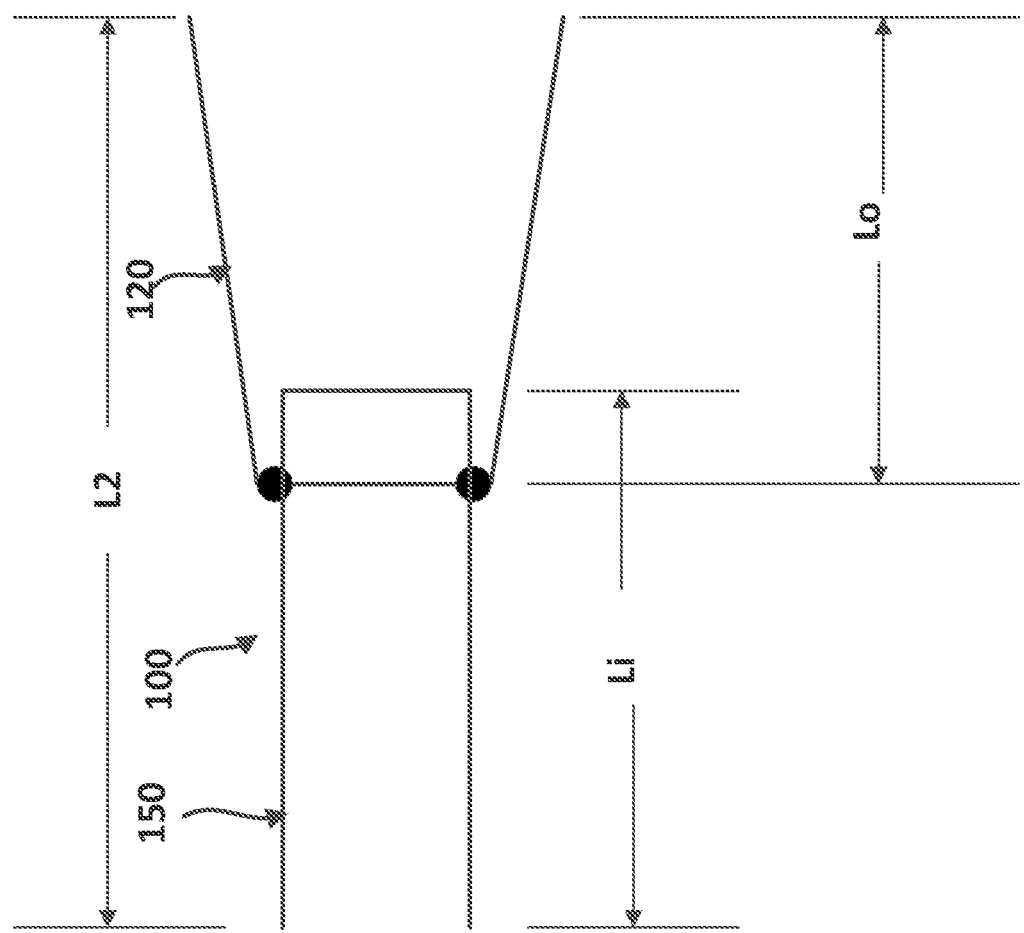
FIGS. 2A and 2B are schematic illustrations of the portion of a prosthetic heart valve of FIGS. 1A and 1B, shown in the first configuration and the second configuration, respectively.

Apparatus and methods are described herein for prosthetic heart valves, such as prosthetic mitral valves, that can be configured to be moved to an inverted configuration for delivery of the prosthetic valve to within a heart of a patient. As described herein, in some embodiments, a prosthetic valve includes an outer frame that can be inverted relative to an inner frame when the prosthetic valve is in a biased expanded configuration. The prosthetic mitral valve can be formed with, for example, a shape-memory material. After inverting the outer frame, the prosthetic valve can be inserted into a lumen of a delivery sheath such that the prosthetic valve is moved to a collapsed configuration.

The delivery sheath can be used to deliver the prosthetic valve to within a patient's heart using a variety of different delivery approaches for delivering a prosthetic heart valve (e.g., prosthetic mitral valve) where the inverted prosthetic valve would enter the heart through the atrium of the heart. For example, the prosthetic valves described herein can be delivered using a transfemoral delivery approach as described in PCT International Application No. PCT/US15/14572 (the "572 PCT application") and/or in PCT International Application No. PCT/US16/12305 (the "'305 PCT Application"), each disclosure of which is incorporated by reference in its entirety herein, or via a transatrial approach, such as described in U.S. Provisional Patent Application Ser. No. 62/220,704, entitled "Apparatus and Methods for Transatrial Delivery of Prosthetic Mitral Valve," filed Sep. 18, 2015 (the "'704 provisional application"), which is incorporated herein by reference in its entirety. In another example, the prosthetic valves described herein (e.g., an inverted valve as described herein) could be delivered via a transjugular approach, e.g., via the right atrium and through the atrial septum and into the left atrium, as described in U.S. Provisional Patent Application Ser. No. 62/305,678, entitled "Apparatus and Methods for Delivery of Prosthetic Mitral Valve," (the "'678 provisional application") and in U.S. Patent Application Pub. No. 2017/0079790, entitled "Apparatus and Methods for Delivery of Prosthetic Mitral Valve," (the "'790 publication") each incorporated by reference in its entirety herein. The prosthetic valves described herein can also be delivered apically if desired. With a transapical approach, after the delivery sheath has been disposed within the left atrium of the heart, the prosthetic mitral valve is moved distally out of the delivery sheath such that the inverted outer frame reverts and the prosthetic valve assumes its biased expanded configuration. The prosthetic mitral valve can then be positioned within a mitral annulus of the heart.

In some embodiments, an apparatus includes a delivery sheath that defines a lumen, an elongate member that defines a first lumen and a second lumen and is at least partially disposed within the lumen of the delivery sheath. The apparatus further includes a prosthetic heart valve disposed at least partially within the lumen of the delivery sheath in a collapsed configuration and circumferentially about a portion of the elongate member. The prosthetic heart valve includes an outer frame coupled to an inner frame. The outer frame is movable between a first configuration relative to the inner frame and a second configuration relative to the inner frame in which the outer frame is inverted relative to the inner frame. The prosthetic heart valve is disposed within the lumen of the delivery sheath with the outer frame in the second configuration and disposed axially proximal to the inner frame. The apparatus further includes a first actuation wire releasably coupled to a first portion of the outer frame and routed from the first portion through the first lumen of the elongate member and out a proximal end portion of the delivery sheath. The apparatus further includes a second actuation wire releasably coupled to a second portion of the outer frame and routed from the second portion through the second lumen of the elongate member and out the proximal end portion of the delivery sheath. The first portion and the second portion of the outer frame are configured to be disposed within an atrium of a heart when implanted within the heart.

In some embodiments, a method includes inserting a distal end portion of a delivery sheath through an apical region of a heart and into an atrium of the heart. The delivery sheath has a prosthetic heart valve disposed within a lumen of the delivery sheath. The prosthetic heart valve includes an outer frame and an inner frame coupled to the outer frame. The outer frame is movable between a first position relative to the inner frame and a second position relative to the inner frame in which the outer frame is inverted relative to the inner frame. The prosthetic heart valve is disposed within the lumen of the delivery sheath with the outer frame in the second position relative to the inner frame during the inserting. The method further includes moving the prosthetic heart valve distally out of the delivery sheath. The method further includes causing the outer frame of the prosthetic heart valve to transition to the first position relative to the inner frame such that the prosthetic heart valve at least partially assumes a biased expanded configuration. The method further includes positioning the prosthetic heart valve within an annulus of the heart.

In some embodiments, a method includes inserting a distal end portion of a delivery sheath into an atrium of a heart. The delivery sheath has a prosthetic heart valve disposed within a lumen of the delivery sheath. The prosthetic heart valve includes an outer frame and an inner frame coupled to the outer frame. The outer frame is movable between a first position relative to the inner frame and a second position relative to the inner frame in which the outer frame is inverted relative to the inner frame. The prosthetic heart valve is disposed within the lumen of the delivery sheath with the outer frame in the second position relative to the inner frame and disposed at least partially axially proximal to the inner frame during the inserting. The method further includes moving the prosthetic heart valve distally out of the delivery sheath. The method further includes causing the outer frame of the prosthetic heart valve to transition to the first position relative to the inner frame such that the prosthetic heart valve at least partially assumes a biased expanded configuration. The method further includes positioning the prosthetic heart valve within an annulus of the heart.

In some embodiments, an apparatus includes an outer sheath that defines a lumen, a delivery sheath that defines a lumen and is movably disposed within the lumen defined by the outer sheath, and a prosthetic heart valve disposed within the lumen of the delivery sheath in a collapsed configuration. The prosthetic heart valve includes an outer frame coupled to an inner frame. The inner frame is removably coupled to a distal end portion of a valve holder. The outer frame is movable between a first configuration relative to the inner frame and a second configuration relative to the inner frame in which the outer frame is inverted relative to the inner frame. The prosthetic heart valve is disposed within the lumen of the delivery sheath with the outer frame in the second configuration. The apparatus further includes a first actuation wire releasably copuled to a first portion of the outer frame, and a second acutation wire releasably coupled to a second portion of the outer frame. Each of the first acutation wire and the second acutation wire has (1) a first portion extending proximally from the outer frame, through the lumen of the outer sheath, along an outside wall of the delivery sheaht, and through a first side aperture defined by the delivery sheath, and (2) a second portion extending proximally from the outer frame, through the lumen of the outer sheaht, along the outside all of the delivery sheaht, and through a second side aperture defined by the delivery sheath. The first portion and the second portion of each of the first acutation wire and the second acutation wire are configured to be pulled proximally to urge the outer frame from the second configuration towards the first configuration relative to the inner frame.

In some embodiments, an apparatus includes a prosthetic valve that includes an inner frame and an outer frame coupled to the inner frame at multiple coupling joints. The multiple coupling joints are configured to allow the outer frame to be moved relative to inner frame such that the prosthetic valve can be moved between a first configuration and a second configuration. The outer frame and the inner frame collectively define a first length of the prosthetic valve when the prosthetic valve is in the first configuration and a second length of the prosthetic valve when the prosthetic valve is in the second configuration and the second length is greater than the first length. The inner frame has a length that is the same when the prosthetic valve is in both the first configuration and the second configuration.

In some embodiments, an apparatus includes a prosthetic heart valve that includes an inner frame and an outer frame coupled to the inner frame at multiple coupling joints. The prosthetic valve is movable between a first configuration and a second configuration. The multiple coupling joints are configured to allow the outer frame to be moved between a first position relative to the inner frame and a second position relative to inner frame in which the outer frame is inverted relative to the inner frame. The prosthetic valve is in the first configuration when the outer frame is in the first position, and in the second configuration when the outer frame is in the second position.

In some embodiments, an apparatus includes a prosthetic heart valve that includes an inner frame, and an outer frame coupled to the inner frame at multiple coupling joints. The multiple coupling joints are configured to allow the outer frame to be moved relative to inner frame such that the prosthetic valve can be moved between a first configuration and a second configuration. The outer frame has an outer frame coupling portion coupled to the inner frame at multiple coupling joints and an outer frame free end portion. The inner frame has an inner frame coupling portion coupled to the outer frame at the multiple coupling joints. A first end portion and an inner frame free end portion are on an opposite end of the inner frame from the first end portion. The multiple coupling joints are disposed between the outer frame free end portion and the first end portion of the inner frame when the prosthetic valve is in the first configuration. The multiple coupling joints are disposed between the inner frame free end portion and the outer frame free end portion when the prosthetic valve is in the second configuration.

In some embodiments, an apparatus includes a prosthetic heart valve that includes an inner frame coupled to an outer frame at multiple coupling joints. The multiple coupling joints are configured to allow the outer frame to be moved relative to inner frame such that the prosthetic valve can be moved between a first configuration and a second configuration. The outer frame has an outer frame coupling portion coupled to the inner frame at the multiple coupling joints and an outer frame free end portion. The inner frame has an inner frame coupling portion coupled to the outer frame at the multiple coupling joints and an inner frame free end portion. The outer frame free end portion and the inner frame free end portion each open in the same direction when the prosthetic valve is in the first configuration. The outer frame free end portion and the inner frame free end portion open in opposite directions when the prosthetic valve is in the second configuration.

In some embodiments, an apparatus includes a delivery sheath that defines a lumen, a valve holder movably disposable within the lumen of the delivery sheath and a prosthetic heart valve disposed at least partially within the lumen of the delivery sheath in a collapsed configuration. The prosthetic heart valve includes an outer frame coupled to an inner frame and the inner frame is removably coupled to a distal end portion of the valve holder. The outer frame is movable between a first configuration relative to the inner frame and a second configuration relative to the inner frame in which the outer frame is inverted relative to the inner frame. The prosthetic heart valve is disposed within the lumen of the delivery sheath with the outer frame in the second configuration. A first actuation wire is releasably coupled to a first portion of an open free end portion of the outer frame and a second actuation wire is releasably coupled to a second portion of the open free end portion of the outer frame. Each of the first actuation wire and the second actuation wire have a first portion extending proximally from the outer frame and a second portion extending proximally from the outer frame. The first portion and the second portion of each of the first actuation wire and the second actuation wire are configured to be pulled proximally to urge the outer frame from the second configuration towards the first configuration relative to the inner frame.

In some embodiments, an apparatus includes an outer sheath that defines a lumen, an inner sheath movably disposed within the lumen of the outer sheath and defining a lumen, a tube member movably disposed within the lumen of the outer sheath and defining a lumen, a valve holder movably disposed within the lumen of the inner sheath and within a lumen defined by the tube member and a prosthetic heart valve disposed at least partially within the lumen of the outer sheath and at least partially within the lumen of the inner sheath. The prosthetic heart valve includes an outer frame coupled to an inner frame and the inner frame is removably coupled to a distal end portion of the valve holder. The outer frame is movable between a first configuration relative to the inner frame and a second configuration relative to the inner frame in which the outer frame is inverted relative to the inner frame. The prosthetic heart valve is disposed within the lumen of the outer sheath and the lumen of the inner sheath with the outer frame in the second configuration. A first actuation wire is releasably coupled to a first portion of an open free end portion of the outer frame and releasably coupled to the tube member at a first location on the tube member. A second actuation wire is releasably coupled to a second portion of the open free end portion of the outer frame and releasably coupled to the tube member at a second location on the tube member.

In some embodiments, a method includes inserting a distal end portion of a delivery sheath into a left atrium of a heart. The delivery sheath having a prosthetic mitral valve disposed within a lumen of the delivery sheath and the prosthetic mitral valve has an outer frame coupled to an inner frame such that the outer frame can be moved between a first position relative to the inner frame and a second position relative to the inner frame in which the outer frame is inverted relative to the inner frame. The prosthetic valve is disposed within the lumen of the delivery sheath with the outer frame in the second positon relative to the inner frame. The prosthetic mitral valve is moved distally out of the delivery sheath causing the outer frame of the prosthetic mitral valve to revert back to the first position relative to the inner frame such that the prosthetic mitral valve at least partially assumes a biased expanded configuration. The prosthetic mitral valve is positioned within a mitral annulus of the heart.

Figure 2A:
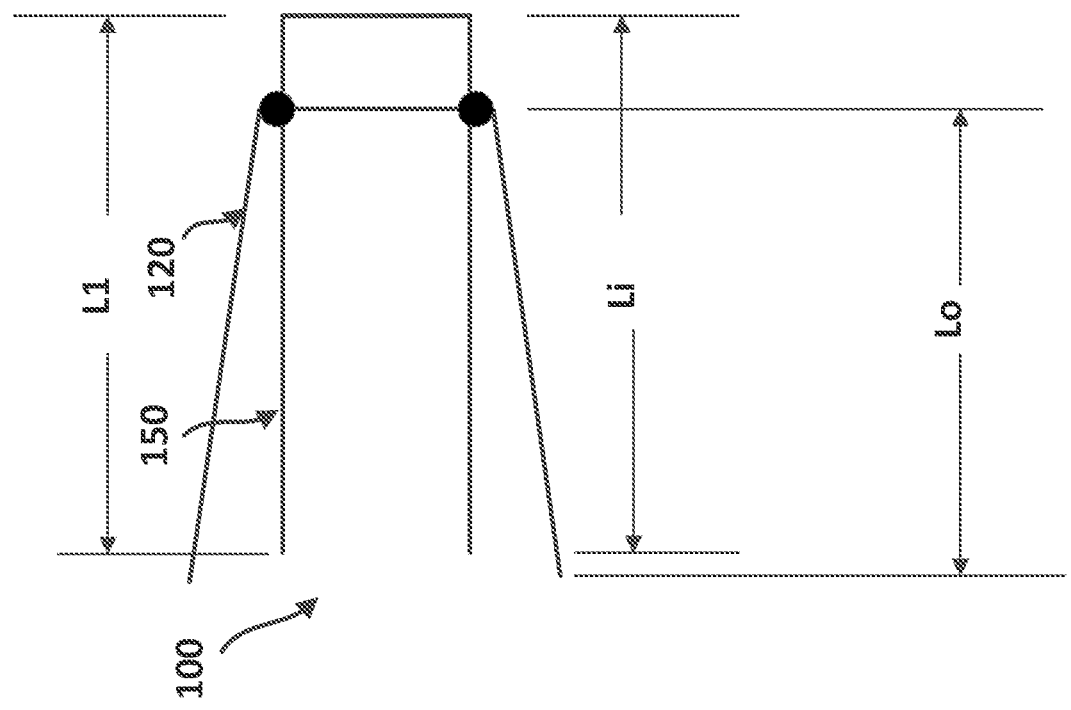

FIGS. 1A and 1B are schematic illustrations of a portion of a prosthetic heart valve 100, according to an embodiment, shown in a first configuration and a second configuration respectively, and FIGS. 1C and 1D illustrate the portions of the prosthetic heart valve 100 of FIGS. 1A and 1B, respectively, shown disposed within a lumen of a delivery sheath 126. FIGS. 2A and 2B illustrate a portion of the prosthetic heart valve 100 of FIGS. 1A and 1B, respectively, and show length dimensions for the prosthetic heart valve in each of the first configuration and the second configuration. As described above, in some situations, such as when delivering a prosthetic valve to the heart via a transfemoral, transatrial or transjugular approach, because of the smaller size of the lumen of the delivery sheath, the size of the prosthetic valve during delivery should be sized accordingly. Thus, it is desirable to have a prosthetic valve that can be reconfigured between a biased expanded configuration for implantation in the heart (e.g., within a native mitral annulus) and a delivery configuration that has a smaller outer perimeter or profile to allow for delivery within the lumen of the delivery sheath. The prosthetic valve 100 and the embodiments of a prosthetic valve described herein can be constructed and formed to achieve these desired functions and characteristics.

The prosthetic heart valve 100 (also referred to herein as "prosthetic valve" or "valve") can be, for example, a prosthetic mitral valve. The valve 100 includes an outer frame 120 and an inner frame 150. The outer frame 120 and the inner frame 150 are each formed as a tubular structure as described in more detail below with reference to FIGS. 3-15. The outer frame 120 and the inner frame 150 can be coupled together at multiple coupling joints 146 disposed about a perimeter of the inner frame 150 and a perimeter of the outer frame 120 as described in more detail below. The valve 100 can also include other features, such as those described with respect to FIGS. 3-15 below. For illustration purposes, only the inner frame 150 and the outer frame 120 are discussed with respect to FIGS. 1A-2B. The various characteristics and features of valve 100 described with respect to FIGS. 1A-2B can apply to any of the prosthetic valves described here.

The outer frame 120 is configured to have a biased expanded or undeformed shape and can be manipulated and/or deformed (e.g., compressed or constrained) and, when released, return to its original (expanded or undeformed) shape. For example, the outer frame 120 can be formed of materials, such as metals or plastics, which have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used. The inner frame 150 can be formed from a laser-cut tube of Nitinol®. The inner frame 150 can also have a biased expanded or undeformed shape and can be manipulated and/or deformed (e.g., compressed and/or constrained) and, when released, return to its original (expanded or undeformed) shape. Further details regarding the inner frame 150 and the outer frame 120 are described below with respect to valve 200 and FIGS. 3-15.

The valve 100 can be delivered and deployed within a left atrium of a heart using a variety of different delivery approaches including, for example, a transfemoral delivery approach, as described in the '572 PCT application and/or in the '305 PCT application, or a transatrial or transjugular approach, as described in the '704 provisional application, the '678 provisional application and the '790 publication") incorporated by reference above. As described above, in some situations, such as when delivering a prosthetic valve to the heart via a transfemoral or transatrial approach, because of the smaller size of the lumen of the delivery sheath, the size of the prosthetic valve during delivery should be sized accordingly. Thus, it is desirable to have a prosthetic valve that can be reconfigured between a biased expanded configuration for implantation in the heart (e.g., within a native mitral annulus) and a delivery configuration that has a smaller outer perimeter or profile to allow for delivery within the lumen of the delivery sheath. The prosthetic valve 100 and the embodiments of a prosthetic valve described herein can be constructed and formed to achieve these desired functions and characteristics.

More specifically, the valve 100 can have a biased expanded configuration (as shown in FIGS. 1A and 2A), an inverted configuration (as shown in FIGS. 1B and 2B), and a compressed or collapsed configuration (as shown in FIGS. 1C and 1D). The expanded configuration allows the valve 100 to function when implanted within the heart. The valve 100 can be moved to the inverted configuration and the compressed or collapsed configuration for delivery of the valve 100 to the heart of a patient.

To enable the valve 100 to be moved to the inverted configuration, the outer frame 120 can be coupled to the inner frame 150 in such a manner to allow the outer frame 120 to move relative to the inner frame 150. More specifically, the coupling joints 146 can couple the outer frame 120 to the inner frame 150 in such a manner to allow the outer frame 120 to be moved relative to the inner frame 150. For example, in some embodiments, the coupling joints 146 can be configured to allow the outer frame 120 to rotate about the coupling joint 146 relative to the inner frame 150. In some embodiments, coupling joints can provide a pivotal coupling between the outer frame 120 and the inner frame 150. In some embodiments, the coupling joints can provide a flexible attachment between the outer frame 120 and the inner frame 150. The coupling joints 146 can be a variety of different types and configurations as described herein with reference to the various embodiments of a prosthetic valve. For example, the coupling joints 146 can include a living hinge, a flexible member, sutures, a suture wrapped through an opening, a pin or tab inserted through an opening or any combinations thereof.

To move the valve 100 from the expanded configuration (FIG. 1A) to the inverted configuration (FIG. 1B), the outer frame 120 is moved to a prolapsed or inverted configuration relative to the inner frame 150, as shown in FIGS. 1B, 1D and 2B, by moving (e.g., rotating, pivoting, flexing) the outer frame 120 about the coupling joints 146. The elastic or superelastic structure of outer frame 120 of valve 100 also allows the outer frame 120 to be moved to, and disposed in, the prolapsed or inverted configuration relative to the inner frame 150. To move the outer frame 120 to the inverted configuration relative to the inner frame 150, the outer frame 120 is folded or inverted distally (to the right in FIG. 1B) relative to the inner frame 150 via the coupling joints 146. As shown in FIGS. 1A and 2A, the outer frame 120 is in a first position relative to the inner frame 150 prior to being inverted in which an open or free end portion 116 (also referred to the atrium portion 116 of the outer frame 120) is disposed proximally or to the left of the coupling joints 146 and in the same direction as a free end portion 147 (also referred to as a second end portion of the inner frame) of the inner frame 150. When the outer frame 120 is moved to an inverted configuration (i.e., second positon relative to the inner frame 150), the free end portion 116 is disposed distally of the coupling joints 146 (or to the right in FIGS. 1B and 2B) and in an opposite direction as the free end portion 147 of the inner frame 150. Said another way, when the valve 100 is in a biased expanded configuration (e.g., FIG. 1A), the coupling joints 146 are disposed between a first end portion 144 (also referred to as a tether coupling portion) of the inner frame 150 and the free end portion 116 of the outer frame 120. When the valve 100 is in the inverted configuration (e.g., FIG. 1B) (i.e., the outer frame 120 has been moved to an inverted configuration or position), the coupling joints 146 are disposed between the free end portion or second end portion 147 of the inner frame 150 and the free end portion 116 of the outer frame 120.

When in the inverted configuration, an overall length of the valve 100 is increased, but a length of the inner frame 150 and a length of the outer frame 120 remains the same (or substantially the same). For example, as shown in FIGS. 2A and 2B an overall length L1 of the valve 100 in the biased expanded configuration (prior to being inverted as shown in FIG. 2A) is less than the overall length L2 of the valve 100 when in the inverted configuration (FIG. 2B). A length Li of the inner frame 150 and a length Lo of the outer frame 120 is substantially the same (or the same) when the valve 100 is in both the biased expanded configuration and the inverted configuration. In addition, in some instances, depending on the specific configuration of the outer frame, an overall outer perimeter or outer diameter of the valve 100 can be smaller when the valve 100 is in the inverted configuration.

With the valve 100 in the inverted configuration, the valve 100 can be placed within a lumen of the delivery sheath 126 for delivery of the valve 100 to the left atrium of the heart, as shown in FIG. 1D. When placed within the lumen of the delivery sheath 126, the valve 100 is moved to the collapsed or compressed configuration in which the outer diameter or outer perimeter of the valve 100 is reduced. Because the valve 100 is in the inverted configuration, the valve 100 is able to be placed within a smaller delivery sheath 126 than would otherwise be possible. For example, for comparison purposes, FIG. 1C illustrates the valve 100 placed within a lumen of a delivery sheath 126' where the valve 100 has not been moved to an inverted configuration prior to being disposed within the delivery sheath 126'. As shown in FIG. 1C, an outer diameter of the valve 100 is reduced, but not to as small of a diameter as for the valve 100 when placed in a delivery sheath 126 when in the inverted configuration. Thus, in FIG. 1C, the valve 100 has an overall outer perimeter or outer diameter D1 and in FIG. 1D, the valve 100 has an overall outer perimeter or outer diameter D2, which is less than D1.

Thus, by disposing the outer frame 120 in the inverted configuration, the valve 100 can be collapsed into a smaller overall diameter, i.e. placed in a smaller diameter delivery sheath 126, than would be possible if the valve 100 were merely collapsed radially. This is because when the valve is in the biased expanded configuration, the inner frame 150 is nested within an interior of the outer frame 120, and thus the outer frame 120 must be collapsed around the inner frame 150. In some embodiments, the inner frame 150 and the outer frame are disposed concentrically. Whereas in the inverted configuration, the inner frame 150 and the outer frame 120 are arranged axially with respect to each other (i.e., the inner frame is not nested within the outer frame 150), such that the outer frame 120 can be collapsed without needing to accommodate all of the structure of the inner frame 150 inside it. In other words, with the inner frame 150 disposed mostly inside or nested within the outer frame 120, the layers or bulk of the frame structures cannot be compressed to as small a diameter. In addition, if the frames are nested, the structure is less flexible, and therefore, more force is needed to bend the valve, e.g. to pass through tortuous vasculature or to make tight turn in the left atrium after passing through the atrial septum to be properly oriented for insertion into the mitral valve annulus.

Figure 3:
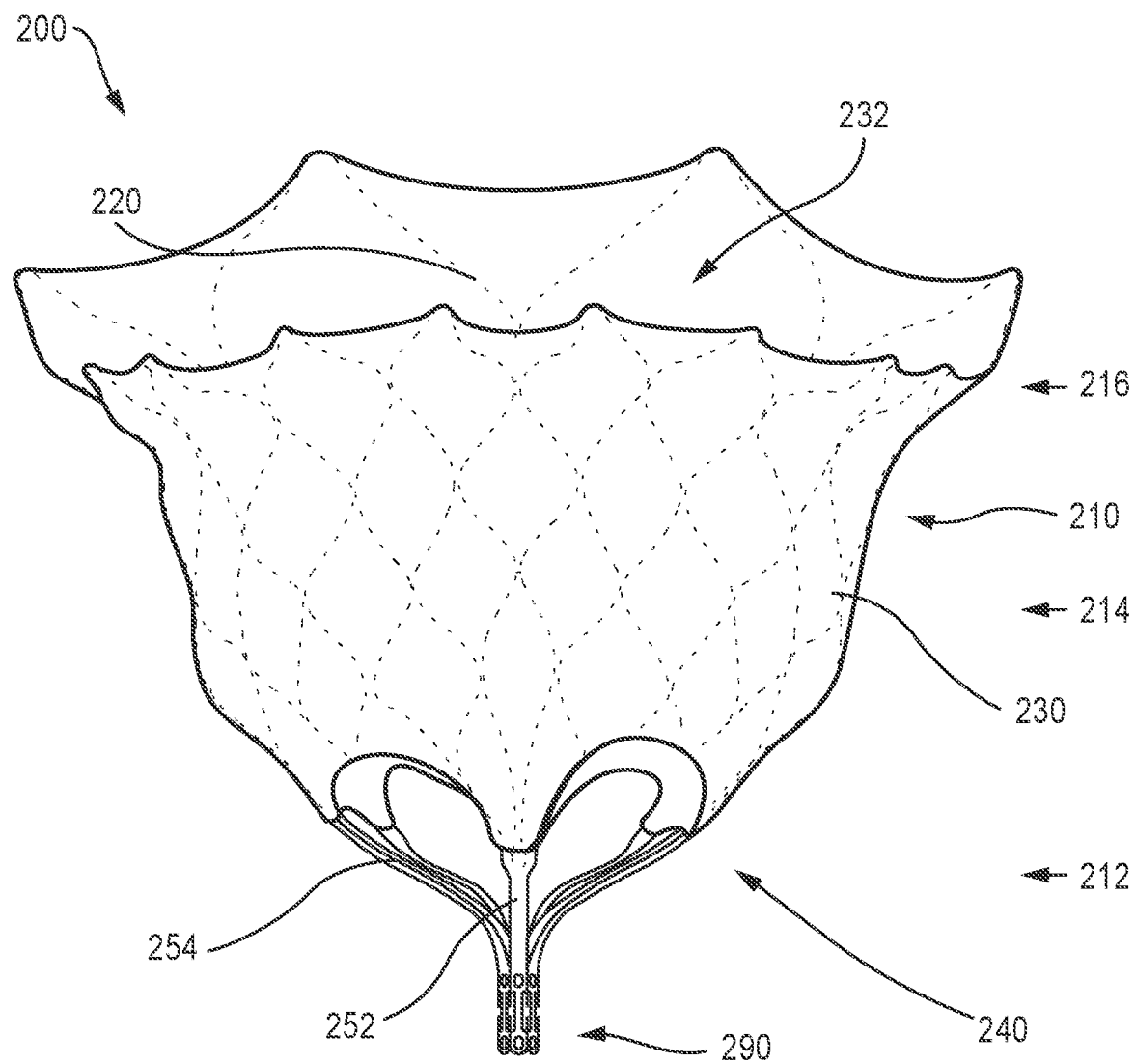
FIGS. 3-5 are front, bottom, and top views of a prosthetic heart valve according to an embodiment.
Figure 4:
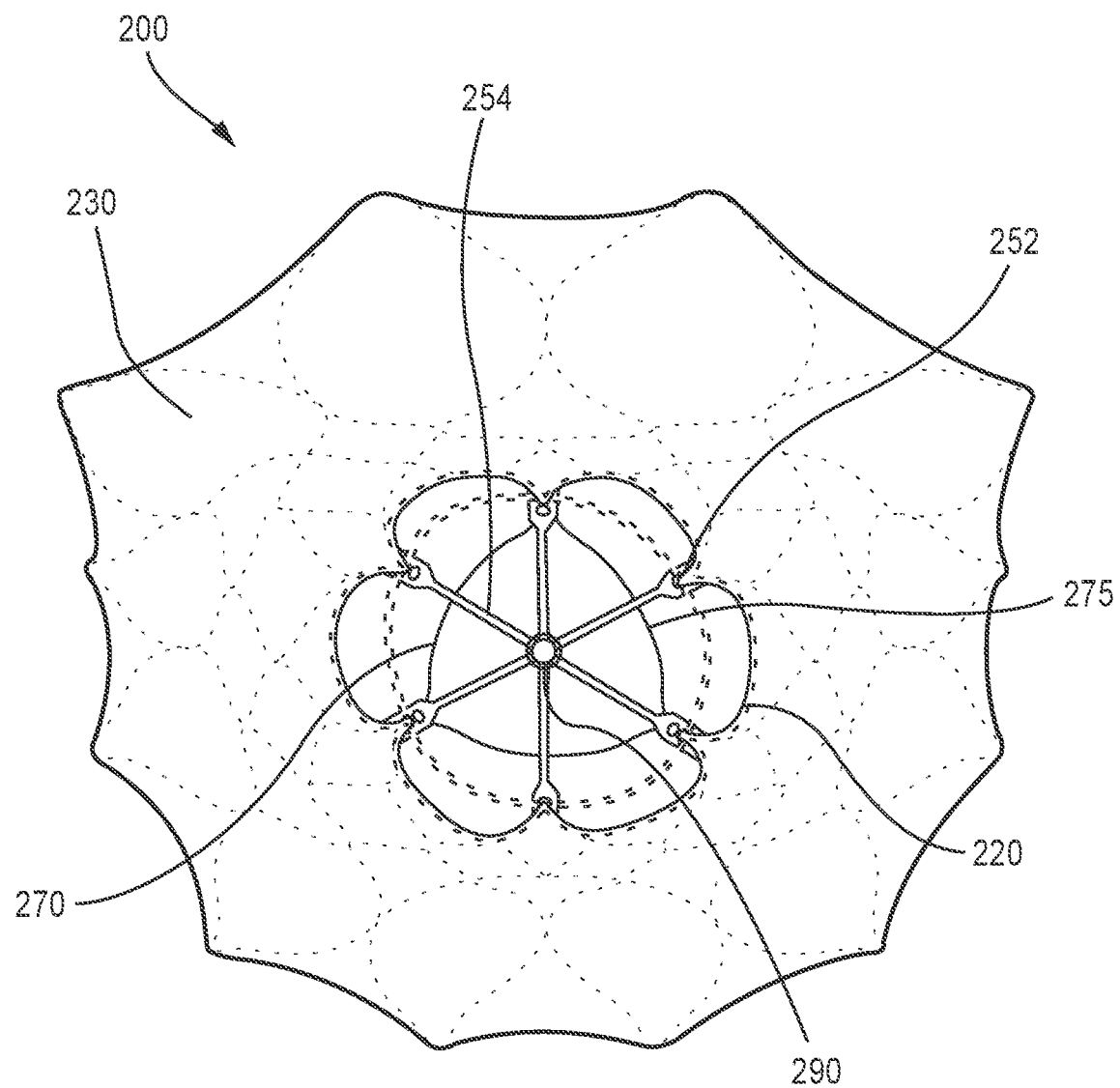
Figure 5:
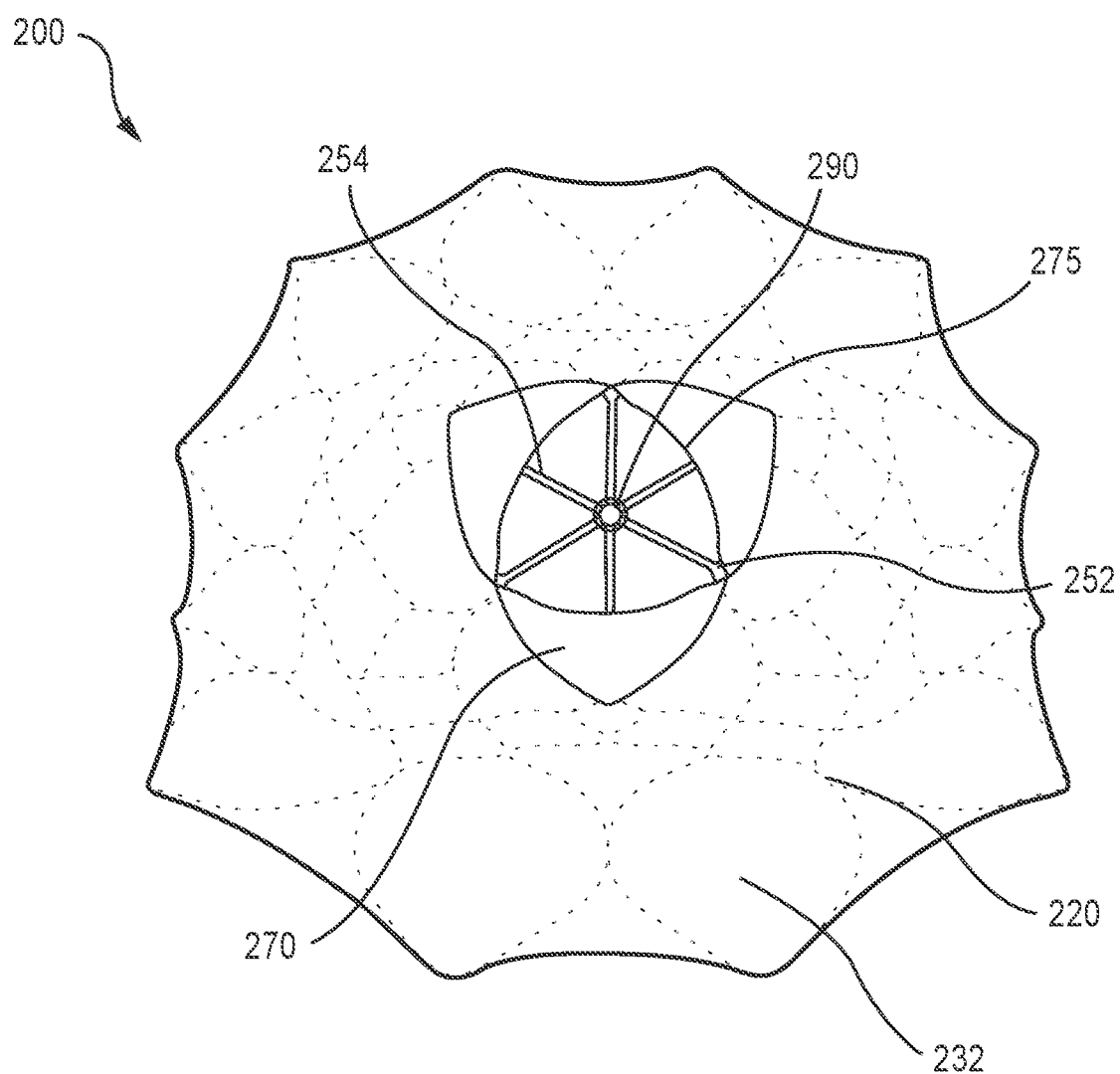

FIGS. 3-14 illustrate another embodiment of a prosthetic heart valve that can be delivered and deployed within a left atrium of a heart using a variety of different delivery approaches including, for example, a transfemoral delivery approach or a transatrial delivery approach. FIGS. 3-5 are front, bottom, and top views, respectively, of a prosthetic heart valve 200 according to an embodiment. Prosthetic heart valve 200 (also referred to herein as "valve" or "prosthetic valve") is designed to replace a damaged or diseased native heart valve such as a mitral valve. Valve 200 includes an outer frame assembly 210 and an inner valve assembly 240 coupled to the outer frame assembly 210.

As shown, outer frame assembly 210 includes an outer frame 220, covered on all or a portion of its outer face with an outer covering 230, and covered on all or a portion of its inner face by an inner covering 232. Outer frame 220 can provide several functions for prosthetic heart valve 200, including serving as the primary structure, as an anchoring mechanism and/or an attachment point for a separate anchoring mechanism to anchor the valve to the native heart valve apparatus, a support to carry inner valve assembly 240, and/or a seal to inhibit paravalvular leakage between prosthetic heart valve 200 and the native heart valve apparatus.

Outer frame 220 has a biased expanded configuration and can be manipulated and/or deformed (e.g., compressed and/or constrained) and, when released, return to its original unconstrained shape. To achieve this, outer frame 220 can be formed of materials, such as metals or plastics, which have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 3, outer frame assembly 210 has an upper end (e.g., at the atrium portion 216), a lower end (e.g., at the ventricle portion 212), and a medial portion (e.g., at the annulus portion 214) therebetween. The upper end or atrium portion 216 (also referred to as "outer free end portion") defines an open end portion of the outer frame assembly 210. The medial or annulus portion 214 of the outer frame assembly 210 has a perimeter that is configured (e.g., sized, shaped) to fit into an annulus of a native atrioventricular valve. The upper end of the outer frame assembly 210 has a perimeter that is larger than the perimeter of the medial portion. In some embodiments, the perimeter of the upper end of the outer frame assembly 210 has a perimeter that is substantially larger than the perimeter of the medial portion. As shown best in FIG. 5, the upper end and the medial portion of the outer frame assembly 210 has a D-shaped cross-section. In this manner, the outer frame assembly 210 promotes a suitable fit into the annulus of the native atrioventricular valve.

Inner valve assembly 240 includes an inner frame 250, an outer covering (not shown), and leaflets 270. As shown, the inner valve assembly 240 includes an upper portion having a periphery formed with multiple arches. The inner frame 250 includes six axial posts or frame members that support the outer covering of the inner valve assembly 240 and leaflets 270. Leaflets 270 are attached along three of the posts, shown as commissure posts 252 (best illustrated in FIG. 4), and the outer covering of the inner valve assembly 240 is attached to the other three posts, 254 (best illustrated in FIG. 4), and optionally to commissure posts 252. Each of outer covering of the inner valve assembly 240 and leaflets 270 are formed of approximately rectangular sheets of material, which are joined together at their upper, or atrium end. The lower, ventricle end of the outer covering of the inner valve assembly 240 may be joined to inner covering 232 of outer frame assembly 210, and the lower, ventricle end of leaflets 270 may form free edges 275, though coupled to the lower ends of commissure posts 252.

Although inner valve assembly 240 is shown as having three leaflets, in other embodiments, an inner valve assembly can include any suitable number of leaflets. The leaflets 270 are movable between an open configuration and a closed configuration in which the leaflets 270 coapt, or meet in a sealing abutment.

Outer covering 230 of the outer frame assembly 210 and inner covering 232 of outer frame assembly 210, outer covering 260 of the inner valve assembly 240 and leaflets 270 of the inner valve assembly 240 may be formed of any suitable material, or combination of materials, such as those discussed above. In this embodiment, the inner covering 232 of the outer frame assembly 210, the outer covering of the inner valve assembly 240, and the leaflets 270 of the inner valve assembly 240 are formed, at least in part, of porcine pericardium. Moreover, in this embodiment, the outer covering 230 of the outer frame assembly 210 is formed, at least in part, of polyester.

Figure 6:
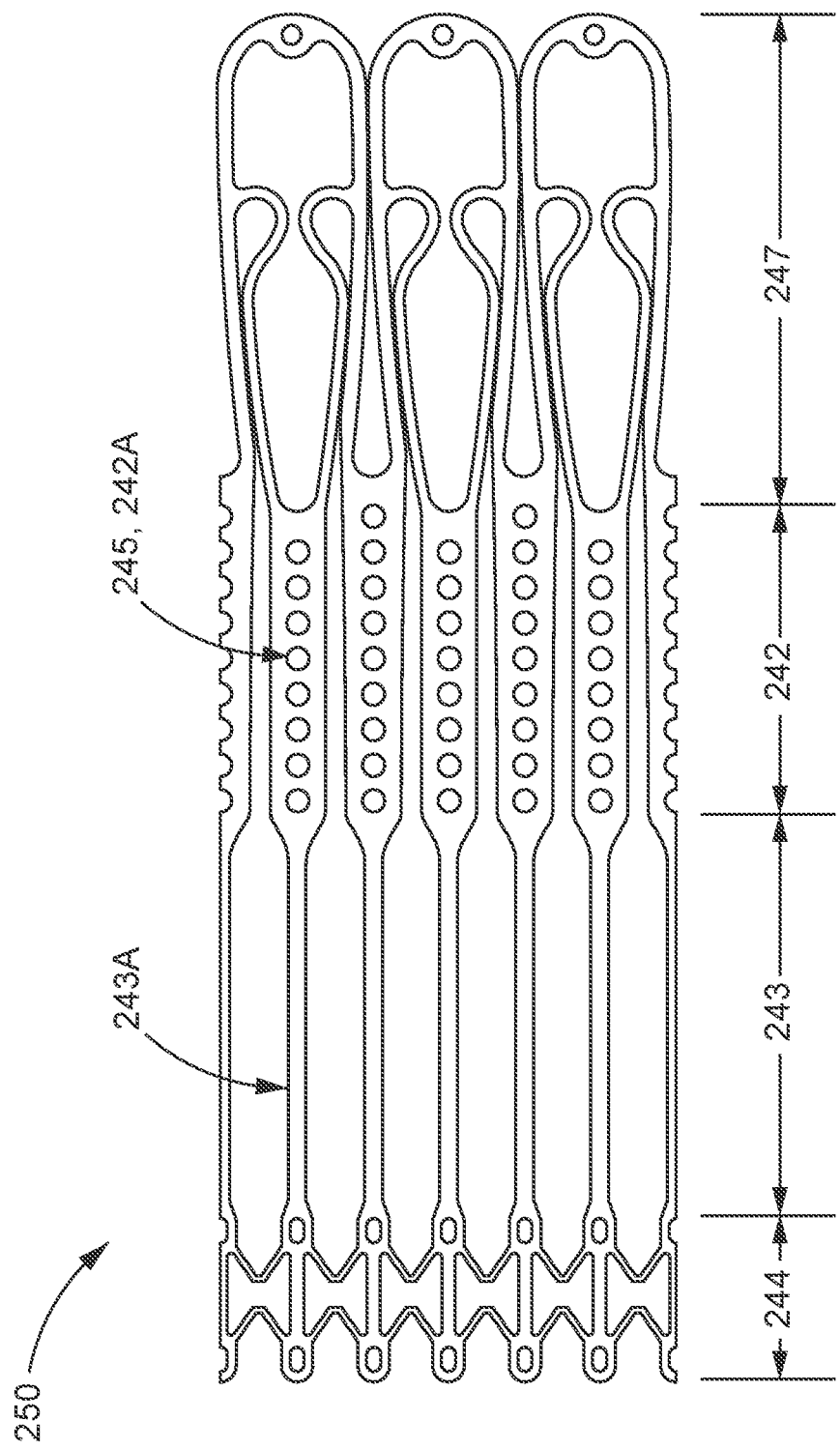
FIG. 6 is an opened and flattened view of the inner frame of the prosthetic heart valve of FIGS. 3-5, in an unexpanded configuration.
Figure 7:
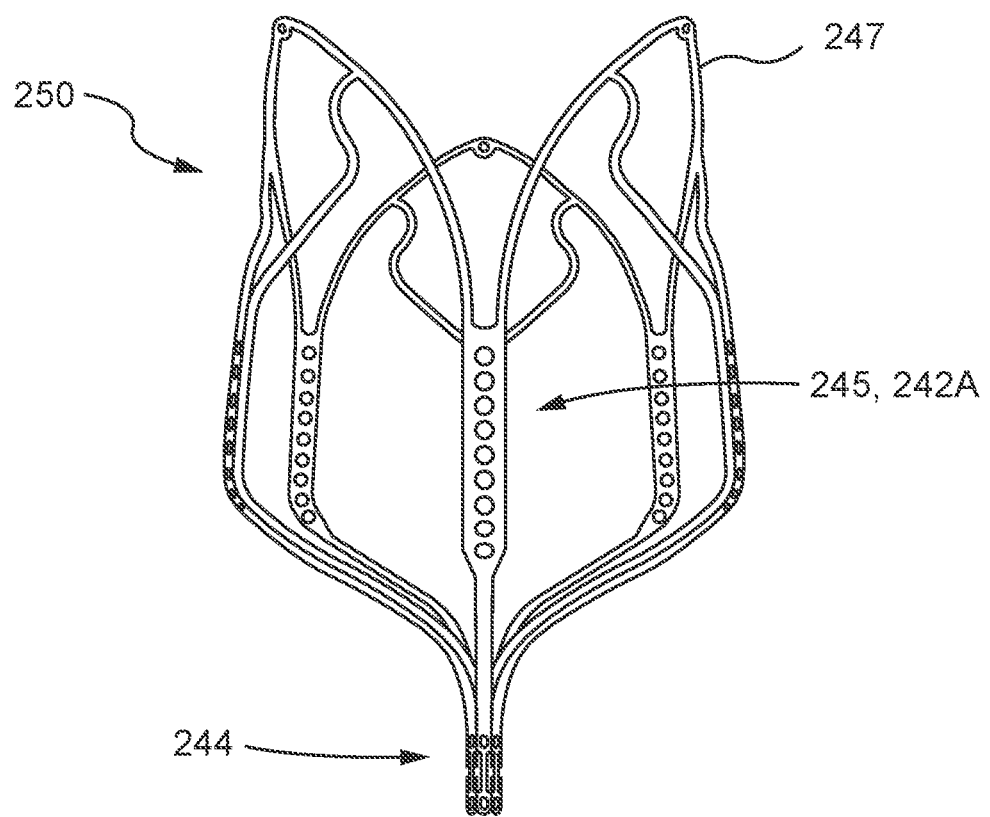
FIGS. 7 and 8 are side and bottom views, respectively, of the inner frame of FIG. 6 in an expanded configuration.
Figure 8:
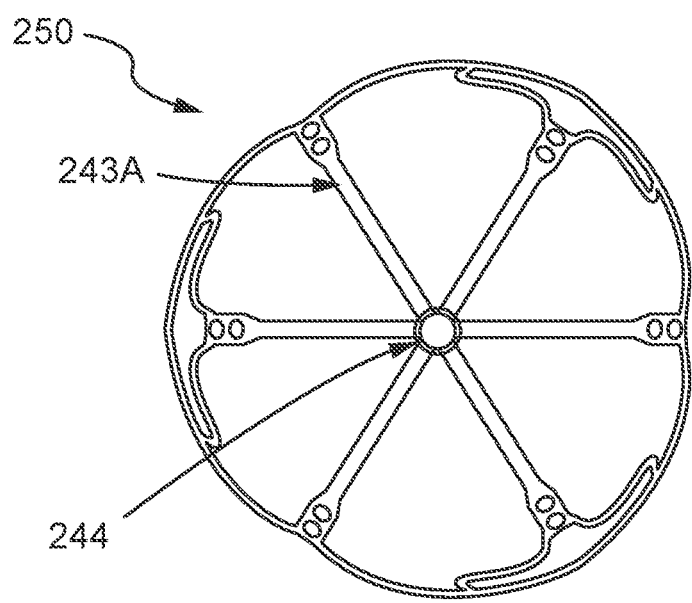

Inner frame 250 is shown in more detail in FIGS. 6-8. Specifically, FIGS. 6-8 show inner frame 250 in an undeformed, initial state (FIG. 6), a side view of the inner frame 250 in an expanded configuration (FIG. 7), and a bottom view of the inner frame 250 in the expanded configuration (FIG. 8), respectively, according to an embodiment.

In this embodiment, inner frame 250 is formed from a laser-cut tube of Nitinol®. Inner frame 250 is illustrated in FIG. 6 in an undeformed, initial state, i.e. as laser-cut, but cut and unrolled into a flat sheet for ease of illustration. Inner frame 250 can be divided into four portions, corresponding to functionally different portions of the inner frame 250 in final form: atrial portion 247, body portion 242, strut portion 243, and tether clamp or connecting portion 244. Strut portion 243 includes six struts, such as strut 243A, which connect body portion 242 to tether connecting portion 244.

Tether connecting portion 244 (also referred to as first end portion of inner frame) includes longitudinal extensions of the struts, connected circumferentially by pairs of opposed, slightly V-shaped connecting members (or "micro-Vs"). Tether connecting portion 244 is configured to be radially collapsed by application of a compressive force, which causes the micro-Vs to become more deeply V-shaped, with the vertices moving closer together longitudinally and the open ends of the V shapes moving closer together circumferentially. Thus, tether connecting portion 244 can be configured to compressively clamp or grip one end of a tether, either connecting directly onto a tether line (e.g. braided filament line) or onto an intermediate structure, such as a polymer or metal piece that is in term firmly fixed to the tether line.

In contrast to tether connecting portion 244, atrial portion 247 (also referred to as "inner frame free end portion") and body portion 242 are configured to be expanded radially. Strut portion 243 forms a longitudinal connection and radial transition between the expanded body portion and the compressed tether connecting portion 244. Body portion 242 provides an inner frame coupling portion 245 that includes six longitudinal posts, such as post 242A. The inner frame coupling portion 245 can be used to attach leaflets 270 to inner frame 240, and/or can be used to attach inner assembly 240 to outer assembly 210, such as by connecting inner frame 250 to outer frame 220. In the illustrated embodiment, the posts include openings through which connecting members (such as suture filaments and/or wires) can be passed to couple the posts to other structures.

Inner frame 250 is shown in a fully deformed, i.e. the final, deployed configuration, in side view and bottom view in FIGS. 7 and 8, respectively.

Figure 9:
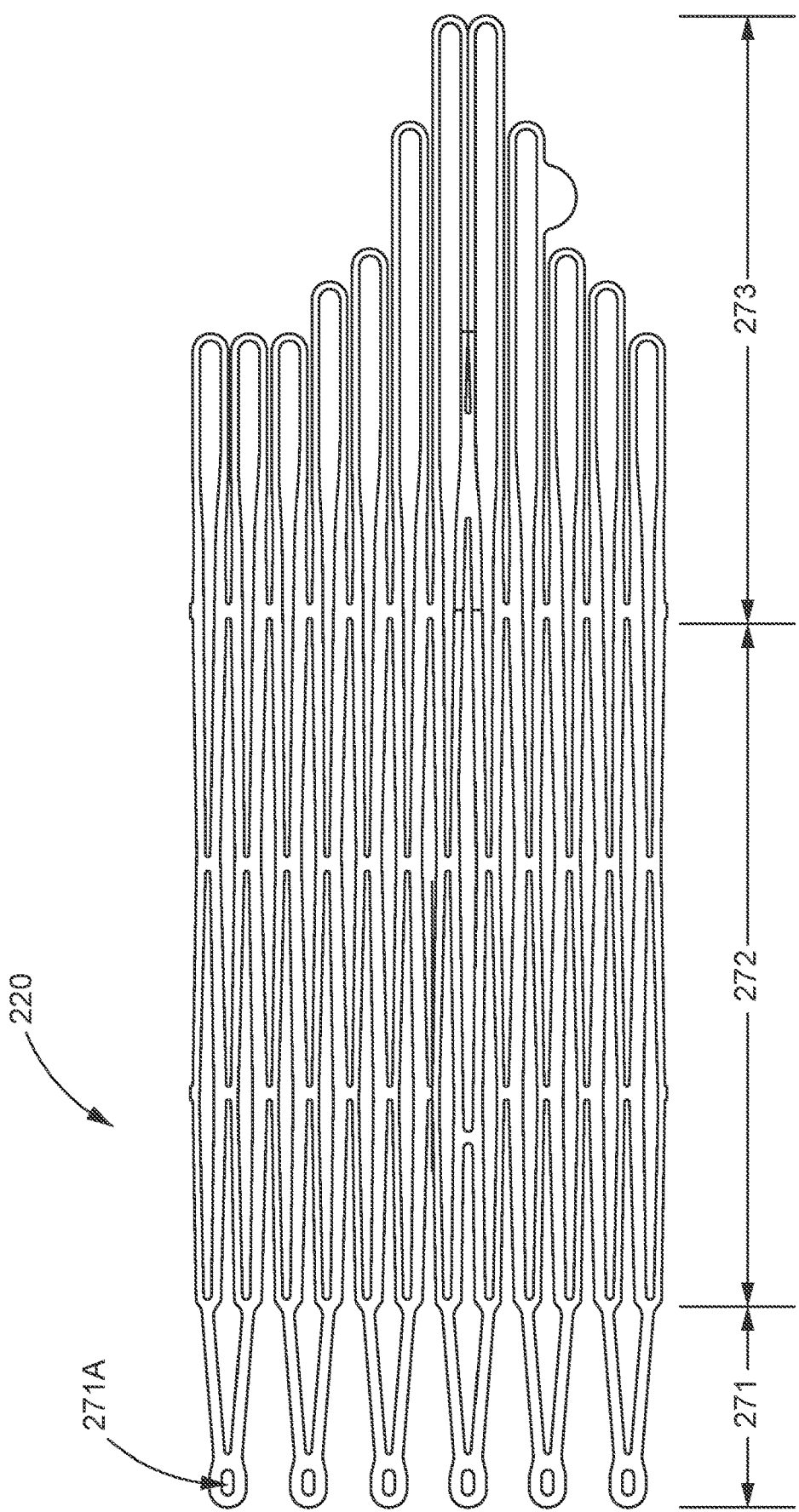
FIG. 9 is an opened and flattened view of the outer frame of the valve of FIGS. 3-5, in an unexpanded configuration.
Figure 10:
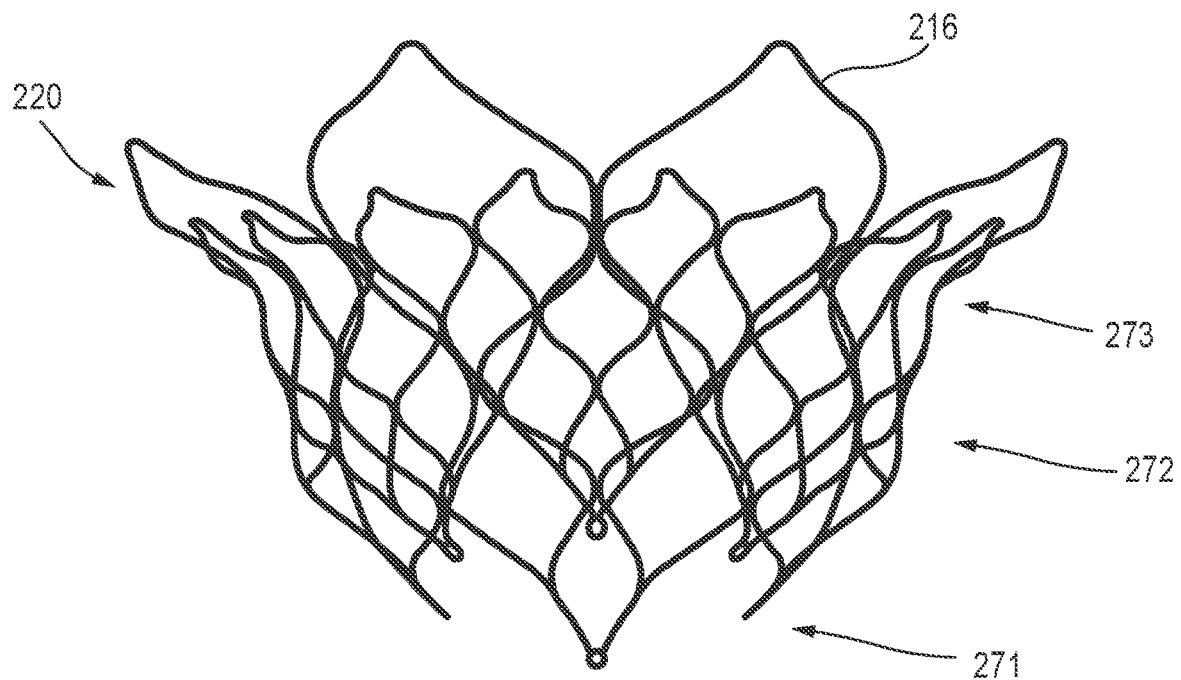
FIGS. 10 and 11 are side and top views, respectively, of the outer frame of FIG. 9 in an expanded configuration.
Figure 11:
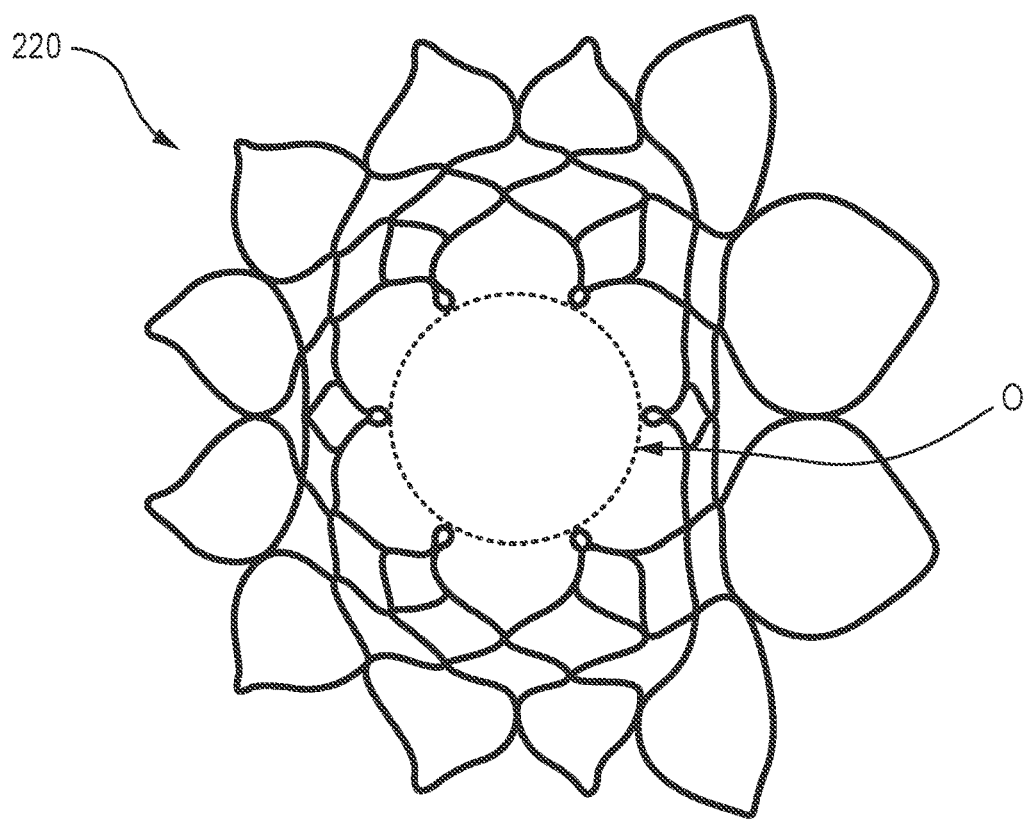

Outer frame 220 of valve 200 is shown in more detail in FIGS. 9-11. In this embodiment, outer frame 220 is also formed from a laser-cut tube of Nitinol®. Outer frame 220 is illustrated in FIG. 9 in an undeformed, initial state, i.e. as laser-cut, but cut and unrolled into a flat sheet for ease of illustration. Outer frame 220 can be divided into an outer frame coupling portion 271, a body portion 272, and a cuff portion 273 (which includes the atrium or free end portion 216), as shown in FIG. 9. Outer frame coupling portion 271 includes multiple openings or apertures, such as 271A, by which outer frame 220 can be coupled to inner frame 250, as discussed in more detail below.

Outer frame 220 is shown in a fully deformed, i.e. the final, deployed configuration, in side view and top view in FIGS. 10 and 11, respectively. As best seen in FIG. 11, the lower end of outer frame coupling portion 271 forms a roughly circular opening (identified by "O" in FIG. 11). The diameter of this opening preferably corresponds approximately to the diameter of body portion 242 of inner frame 250, to facilitate coupling of the two components of valve 200.

Figure 12:
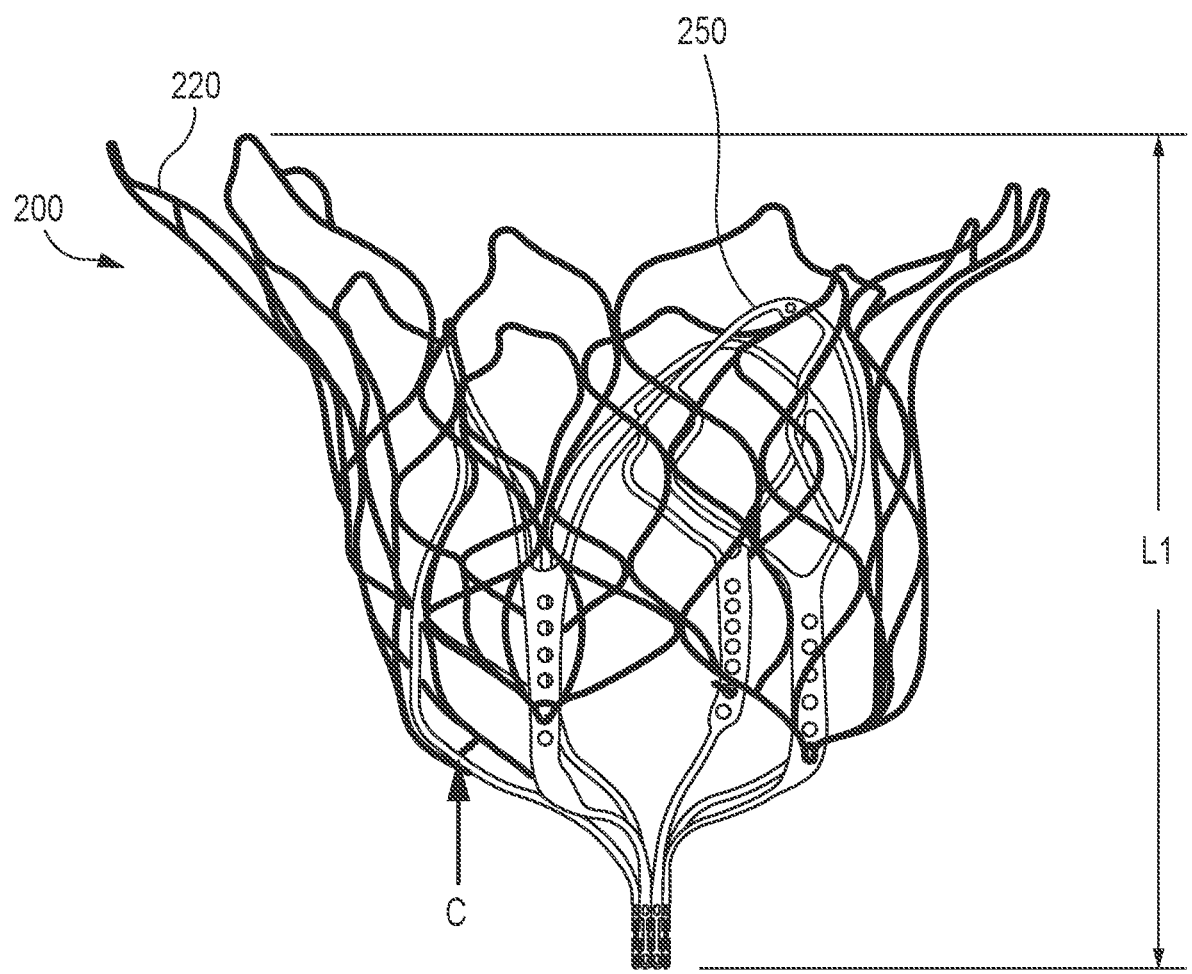
FIGS. 12-14 are side, front, and top views of an assembly of the inner frame of FIGS. 6-8 and the outer frame of FIGS. 9-11.
Figure 13:
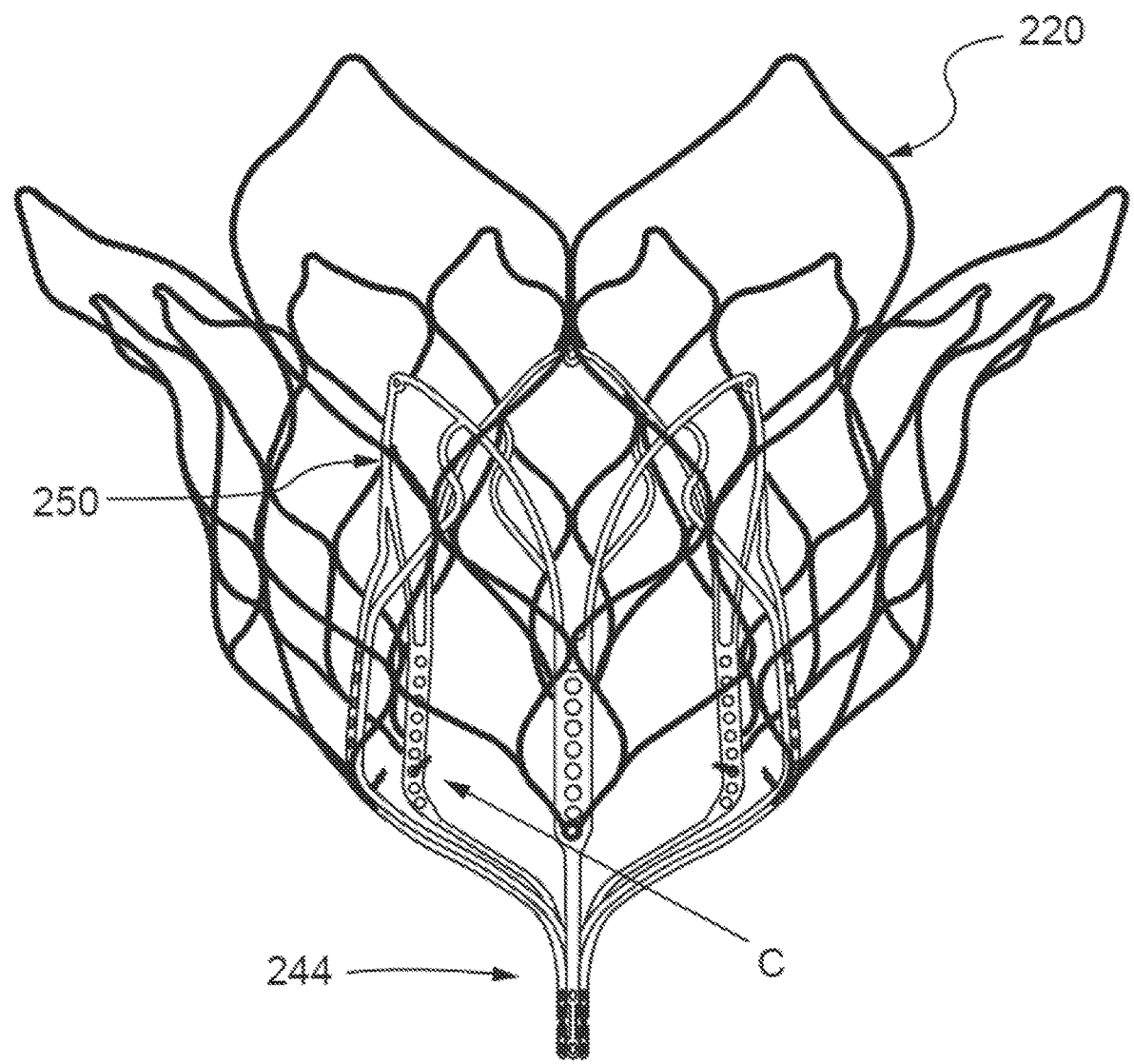
Figure 14:
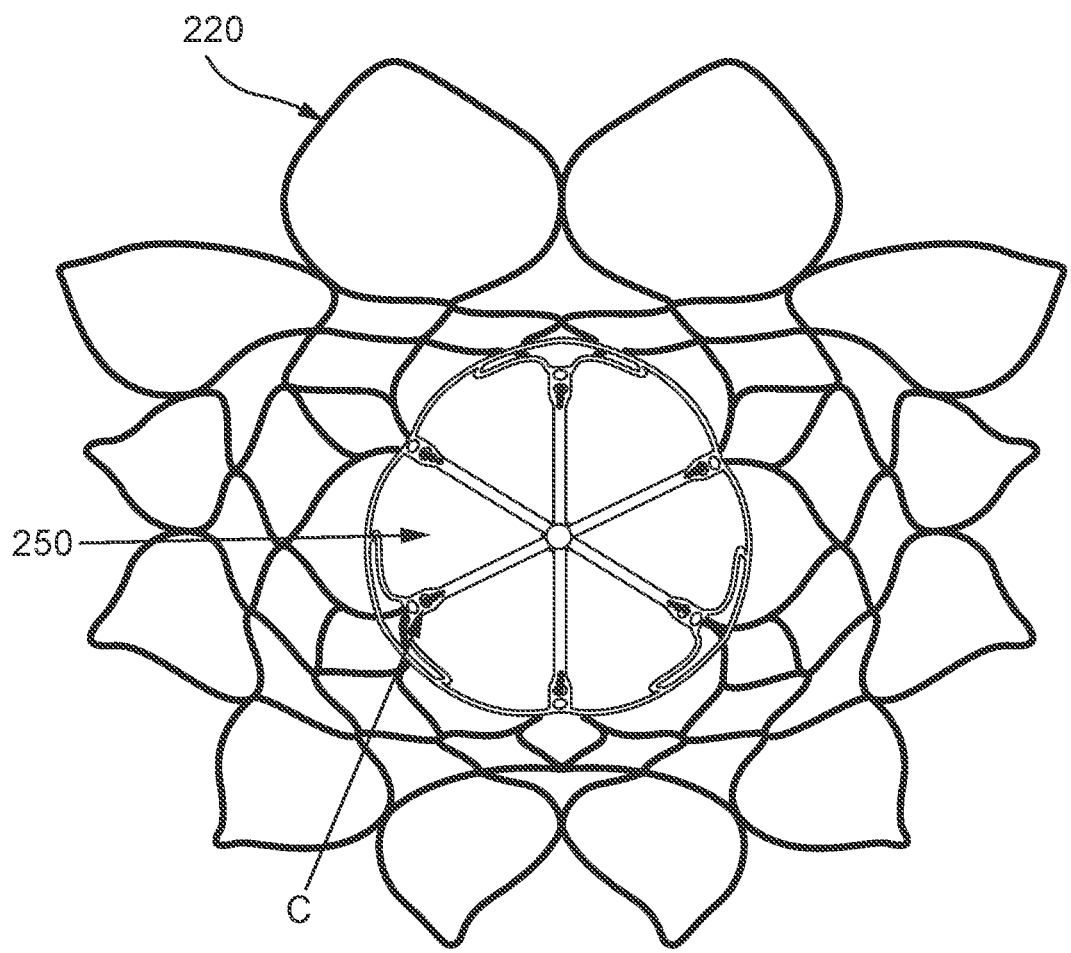

Outer frame 220 and inner frame 250 are shown coupled together in FIGS. 12-14, in front, side, and top views, respectively. The two frames collectively form a structural support for a prosthetic valve such as valve 200. The frames support the valve leaflet structure (e.g., leaflets 270) in the desired relationship to the native valve annulus, support the coverings (e.g., outer covering 230, inner covering 232, outer covering of inner valve assembly 240) for the two frames to provide a barrier to blood leakage between the atrium and ventricle, and couple to the tether (e.g., tether assembly 290) (by the inner frame 250) to aid in holding the prosthetic valve 200 in place in the native valve annulus by the tether connection to the ventricle wall. The outer frame 220 and the inner frame 250 are connected at six coupling points (representative points are identified as "C"). In this embodiment, the coupling points are implemented with a mechanical fastener, such as a short length of wire, passed through an aperture (such as aperture 271A) in outer frame coupling portion 271 and corresponding openings in inner frame coupling portion 245 (e.g., longitudinal posts, such as post 242A) in body portion 242 of inner frame 250. Inner frame 250 is thus disposed within the outer frame 220 and securely coupled to it.

FIGS. 15-21 illustrate a method of reconfiguring a prosthetic heart valve 300 (e.g., prosthetic mitral valve) prior to inserting the prosthetic heart valve 300 into a delivery sheath 326 (see, e.g., FIGS. 17-21) for delivery into the atrium of the heart. The prosthetic heart valve 300 (also referred to herein as "valve") can be constructed the same as or similar to, and function the same as or similar to the valves 100 and 200 described above. Thus, some details regarding the valve 300 are not described below. It should be understood that for features and functions not specifically discussed, those features and functions can be the same as or similar to the valve 200.

Figure 15:
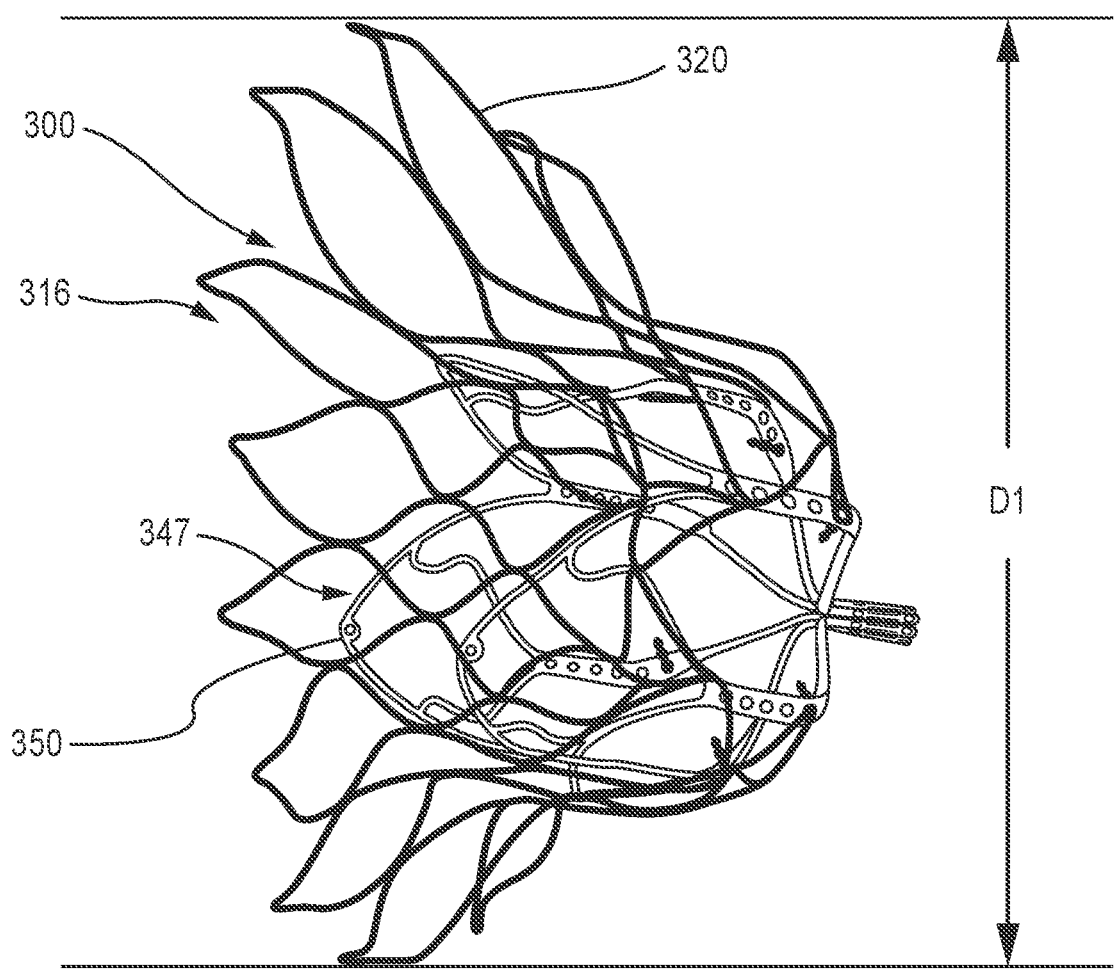
FIG. 15 is a side perspective view of an assembly of an inner frame and an outer frame shown in a biased expanded configuration, according to an embodiment.
Figure 16:
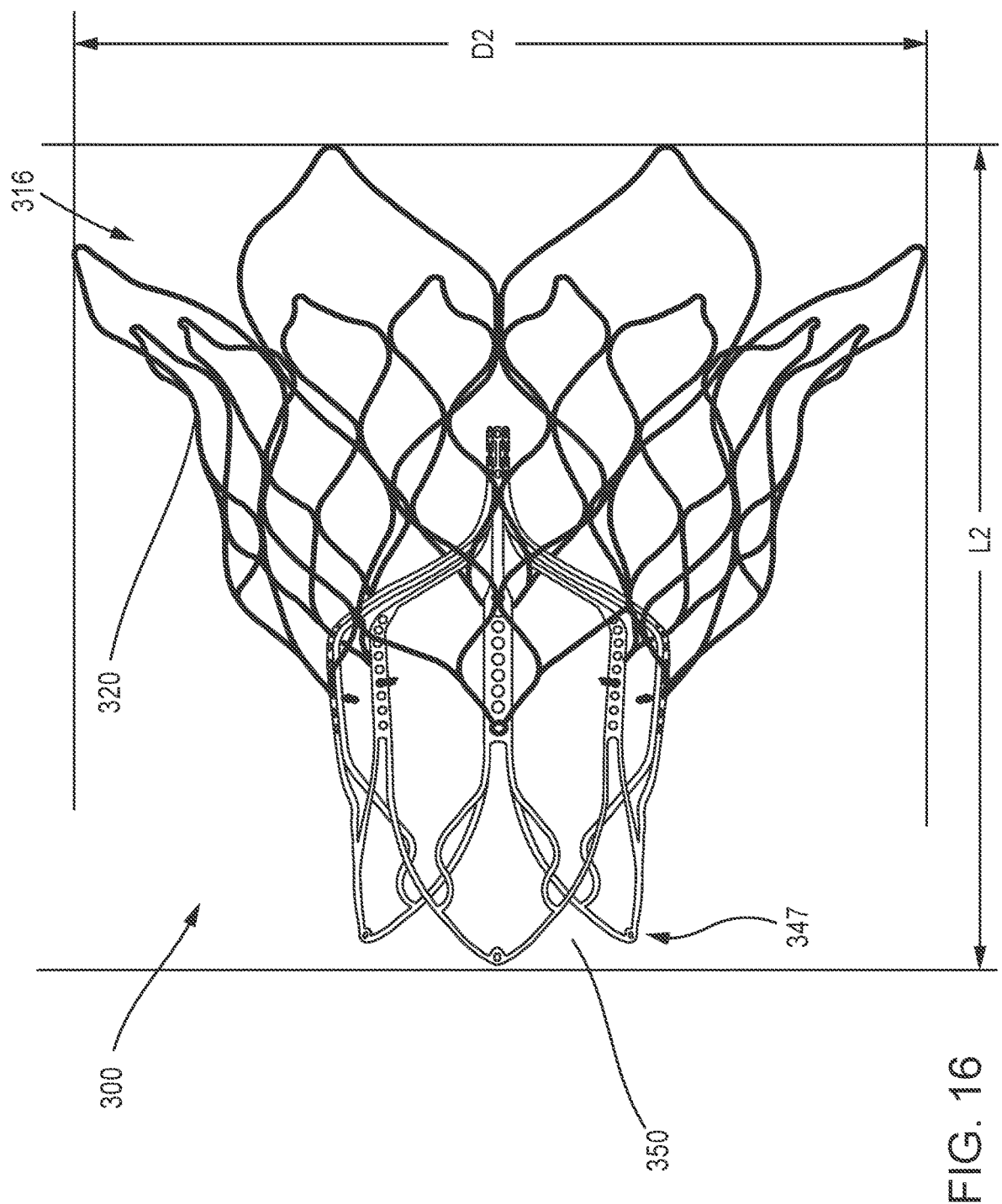
FIG. 16 is a side perspective view of the assembly of FIG. 15 with the outer frame shown inverted.
Figure 17:
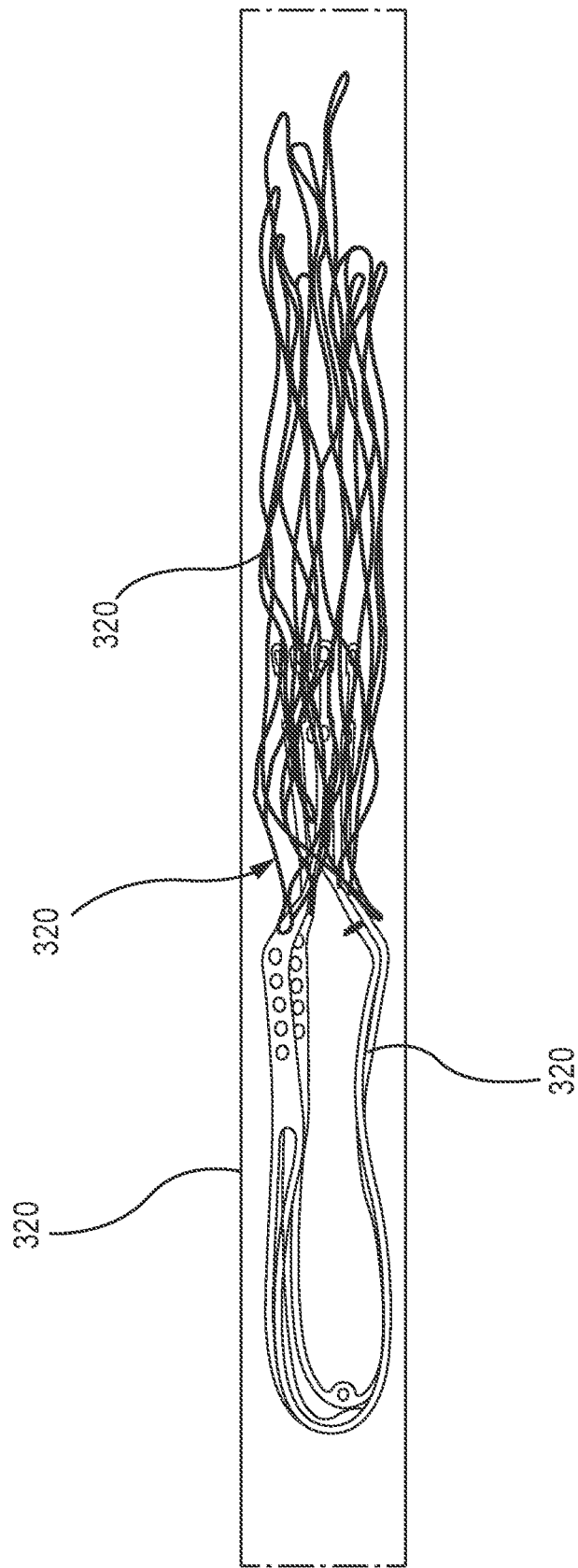
FIG. 17 is side view of the assembly of FIG. 16 shown in a collapsed configuration within a lumen of a delivery sheath.

As shown in FIG. 15, the valve 300 has an outer frame 320 and an inner frame 350. As discussed above for valves 100 and 200, the outer frame 320 and the inner frame 350 of valve 300 can each be formed with a shape-memory material and have a biased expanded configuration. The outer frame 320 and the inner frame 350 can be moved to a collapsed configuration for delivery of the valve 300 to the heart. In this example method of preparing the valve 300 for delivery to the heart, the outer frame 320 of the valve 300 is first disposed in a prolapsed or inverted configuration as shown in FIG. 16. Specifically, the elastic or superelastic structure of outer frame 320 of valve 300 allows the outer frame 320 to be disposed in the prolapsed or inverted configuration prior to the valve 300 being inserted into the lumen of the delivery sheath 326. As shown in FIG. 16, to dispose the outer frame 320 in the inverted configuration, the outer frame 320 is folded or inverted distally (to the right in FIG. 16) such that an open free end 316 of the outer frame 320 is pointed away from an open free end 347 of the inner frame 350. As described above for valve 100, in this inverted configuration, the overall outer perimeter or outer diameter of the valve 300 is reduced and the overall length is increased. For example, the diameter D1 shown in FIG. 15 is greater than the diameter D2 shown in FIG. 16, and the length L1 (shown in FIG. 12 for valve 200) is less than the length L2 shown in FIG. 16 for valve 300. With the outer frame 320 in the inverted configuration relative to the inner frame 350, the valve 300 can be placed within a lumen of a delivery sheath 326 as shown in FIG. 17 for delivery of the valve 300 to the left atrium of the heart. By disposing the outer frame 320 in the inverted configuration relative to the inner frame 350, the valve 300 can be collapsed into a smaller overall diameter, i.e. when placed in a smaller diameter delivery sheath, than would be possible if the valve 300 in the configuration shown in FIG. 15 were collapsed radially without being inverted. This is because in the configuration shown in FIG. 15, the two frames are concentric or nested, and thus the outer frame 320 must be collapsed around the inner frame 350, whereas in the configuration shown in FIG. 16, the two frames are substantially coaxial but not concentric or nested. Thus, in the configuration shown in FIG. 16 the outer frame 320 can be collapsed without the need to accommodate the inner frame 350 inside of it. In other words, with the inner frame 350 disposed mostly inside or nested within the outer frame 320, the layers or bulk of the frame structures cannot be compressed to as small a diameter. In addition, if the frames are nested, the structure is less flexible, and therefore, more force is needed to bend the valve, e.g. to pass through tortuous vasculature or to make tight turn in the left atrium after passing through the atrial septum to be properly oriented for insertion into the mitral valve annulus.

Figure 22:
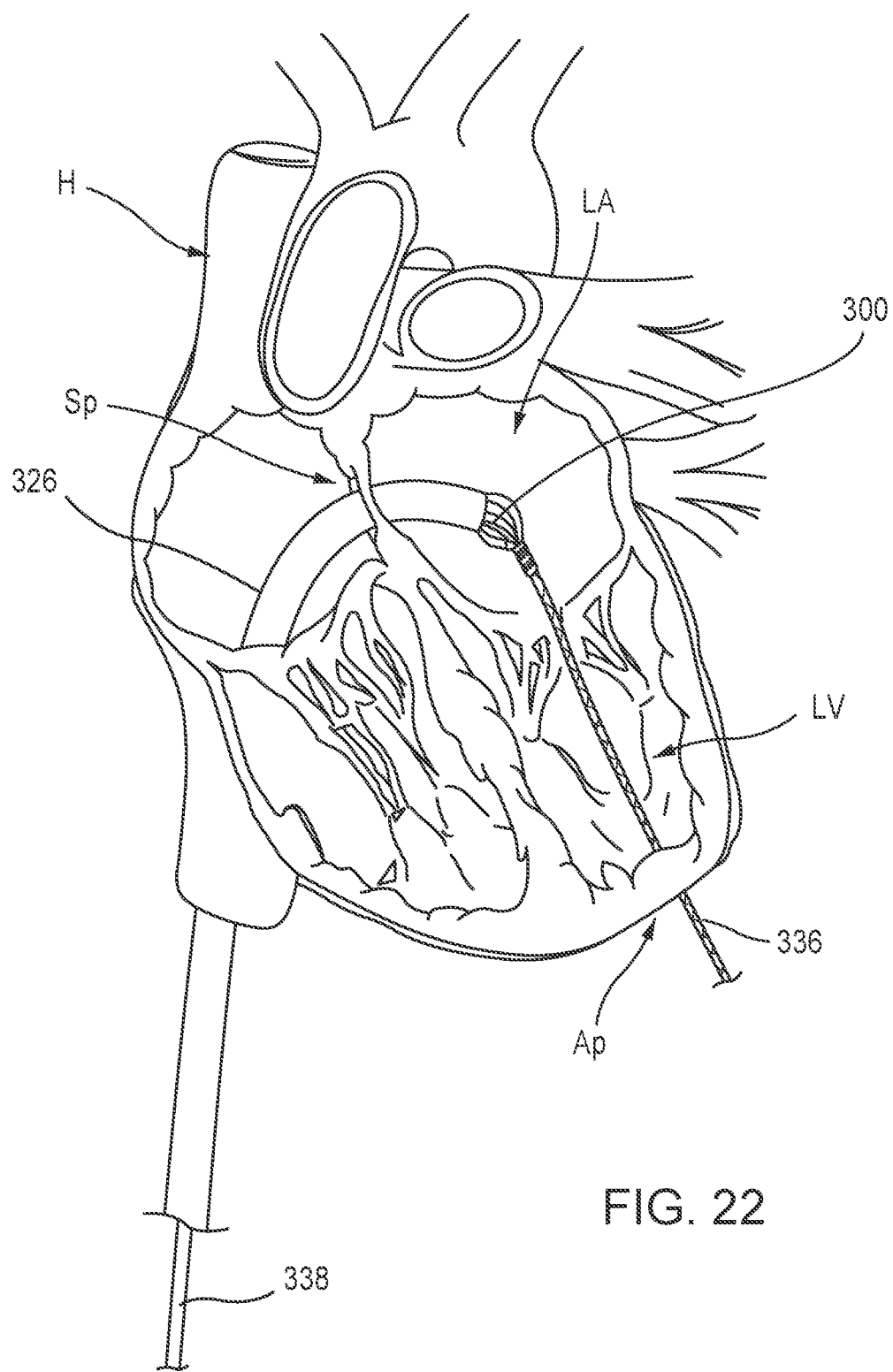
FIGS. 22-24 illustrate steps of a portion of a method to deliver the prosthetic valve of FIGS. 15-21 to an atrium of a heart and within the native mitral annulus.
Figure 23:
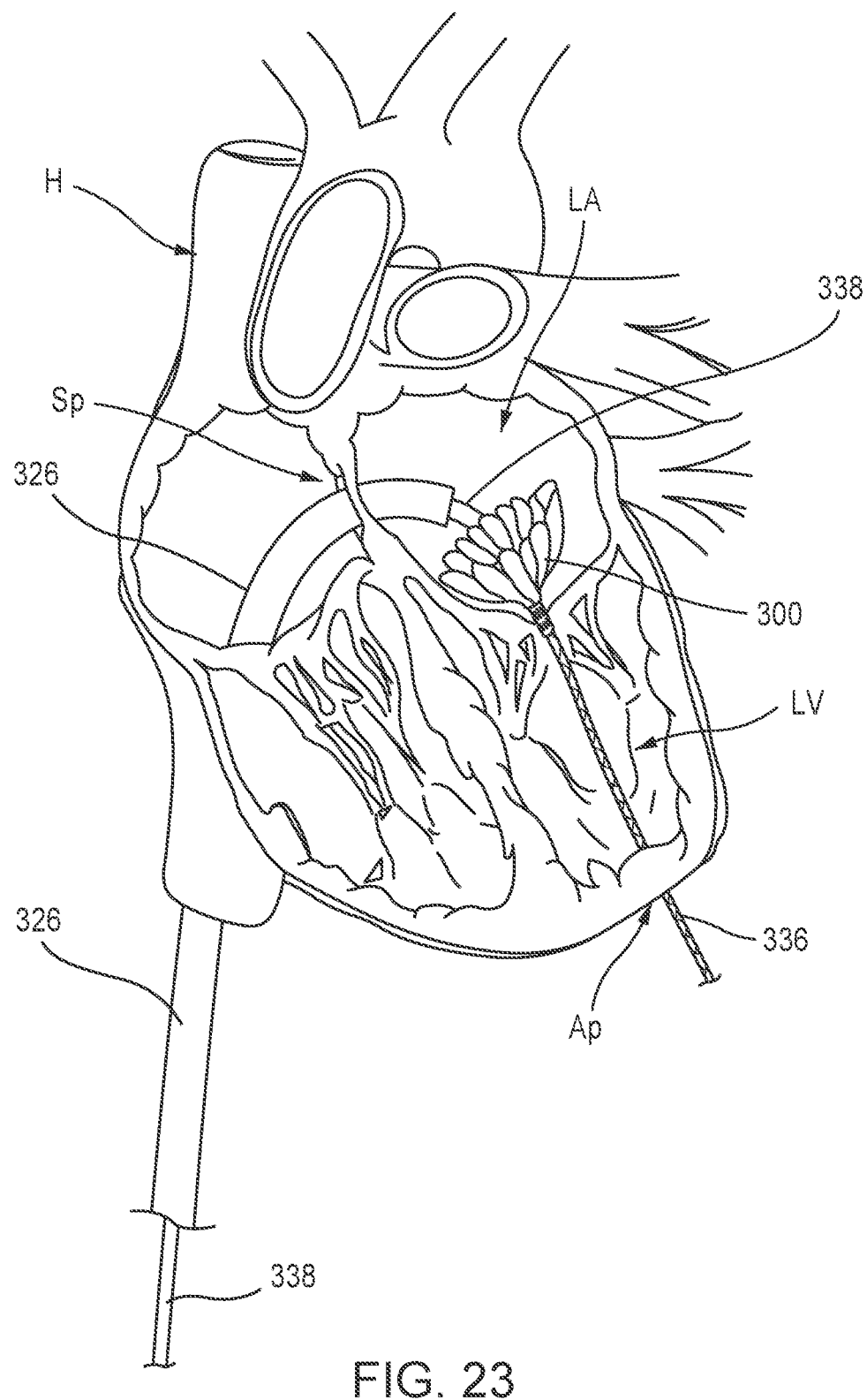
Figure 24:
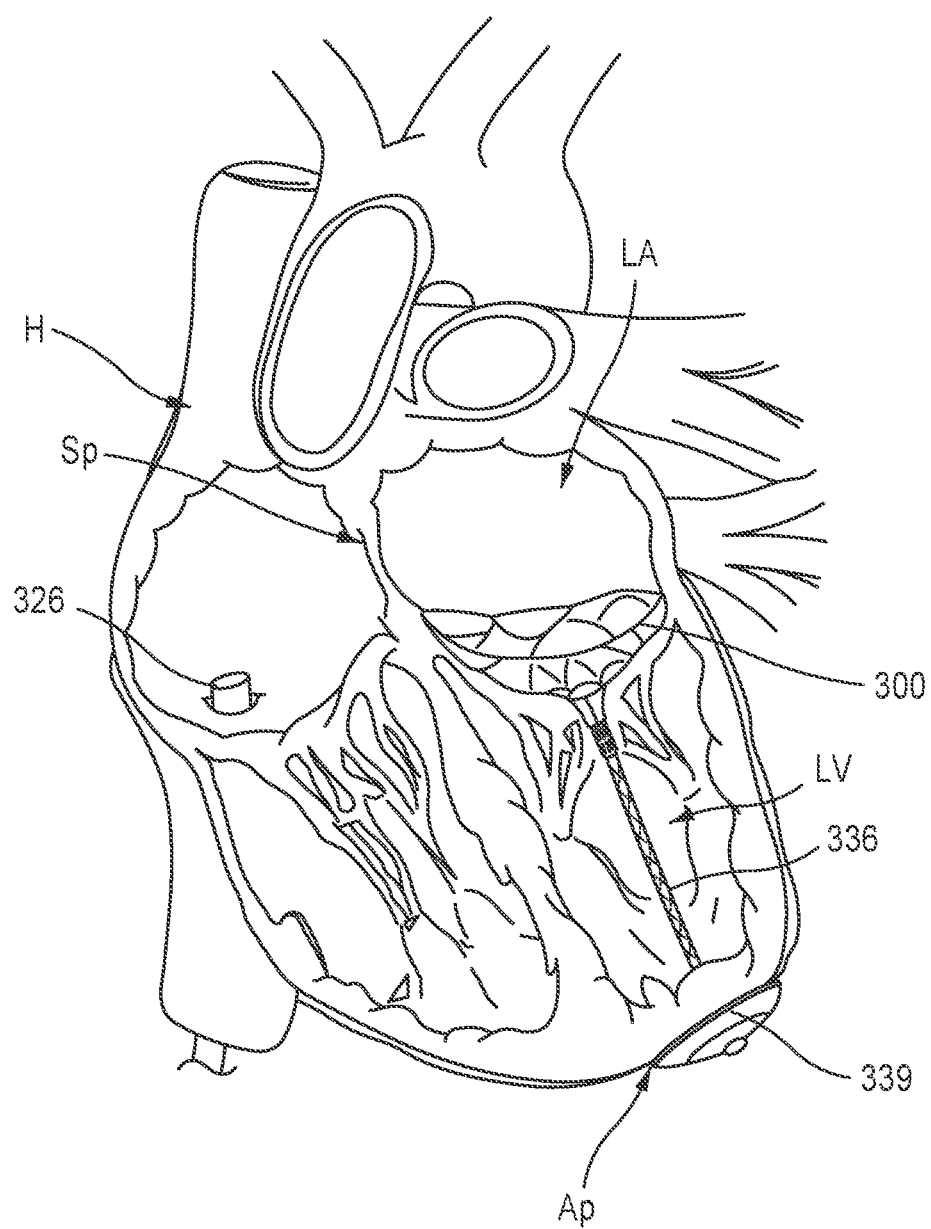

FIGS. 22-24 illustrate a portion of a procedure to deliver the valve 300 to the heart. In this embodiment, the valve 300 is shown being delivered via a transfemoral delivery approach as described, for example, in the '572 PCT application and/or in the '305 PCT Application incorporated by reference above. The delivery sheath 326, with the valve 300 disposed within a lumen of the delivery sheath 326 and in an inverted configuration as shown in FIG. 17, can be inserted into a femoral puncture, through the femoral vein, through the inferior vena cava, into the right atrium, through the septum Sp and into the left atrium LA of the heart. With the distal end portion of the delivery sheath 326 disposed within the left atrium of the heart, the valve 300 can be deployed outside a distal end of the delivery sheath 326. For example, in some embodiments, a pusher device 338 can be used to move or push the valve 300 out the distal end of the delivery sheath 326. As shown in FIGS. 22-24, a tether 336 can be attached to the valve 300, and extend though the mitral annulus, through the left ventricle LV, and out a puncture site at the apex Ap. In some embodiments, the valve 300 can be moved out of the delivery sheath 326 by pulling proximally on the tether 336. In some embodiments, the valve 300 can be deployed by pushing with the pusher device and pulling with the tether.

Figure 18:
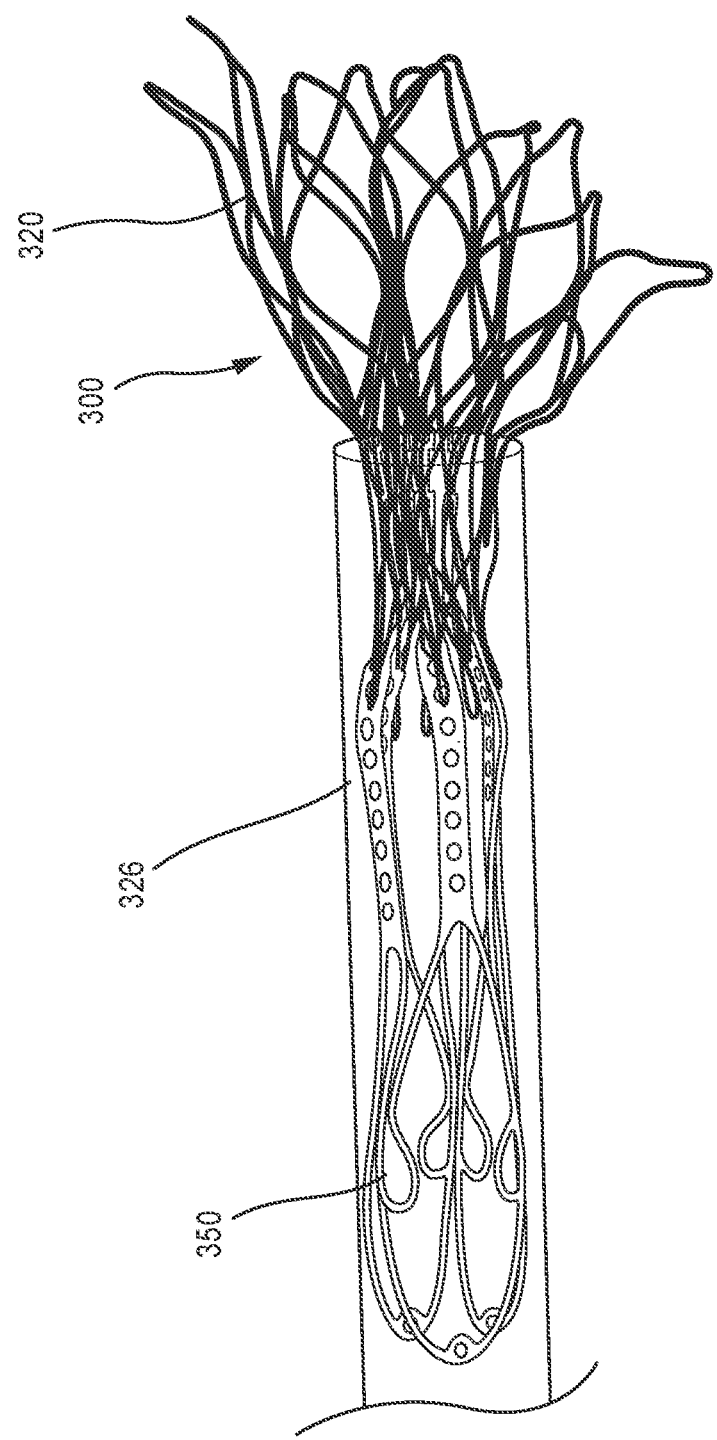
FIG. 18 is a side view of the assembly of FIG. 17 shown in a first partially deployed configuration.
Figure 19:
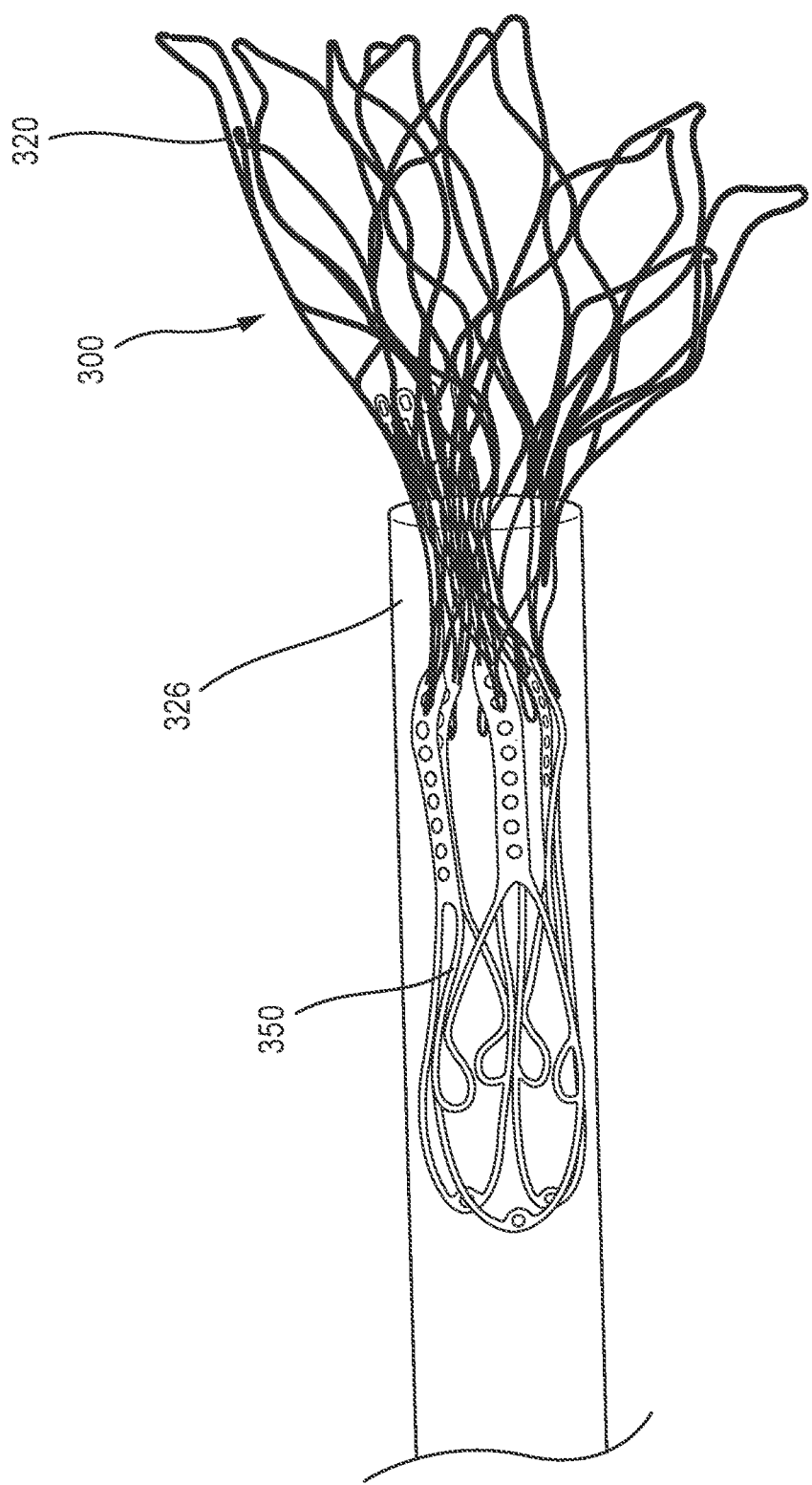
FIG. 19 is a side view of the assembly of FIG. 17 shown in a second partially deployed configuration.
Figure 20:
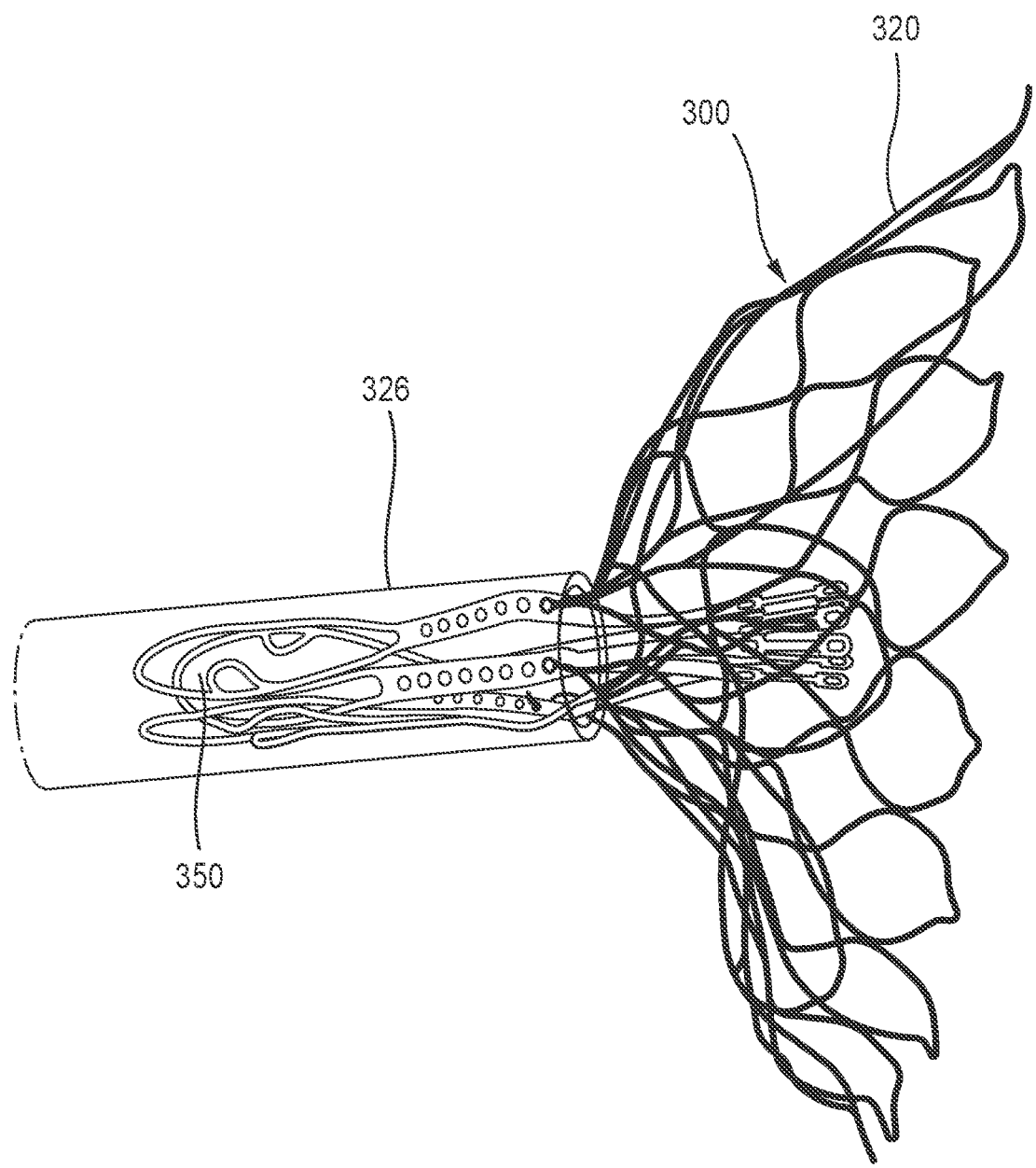
FIG. 20 is a side view of the assembly of FIG. 17 shown in a third partially deployed configuration in which the inverted outer frame is substantially deployed outside of the delivery sheath.
Figure 21:
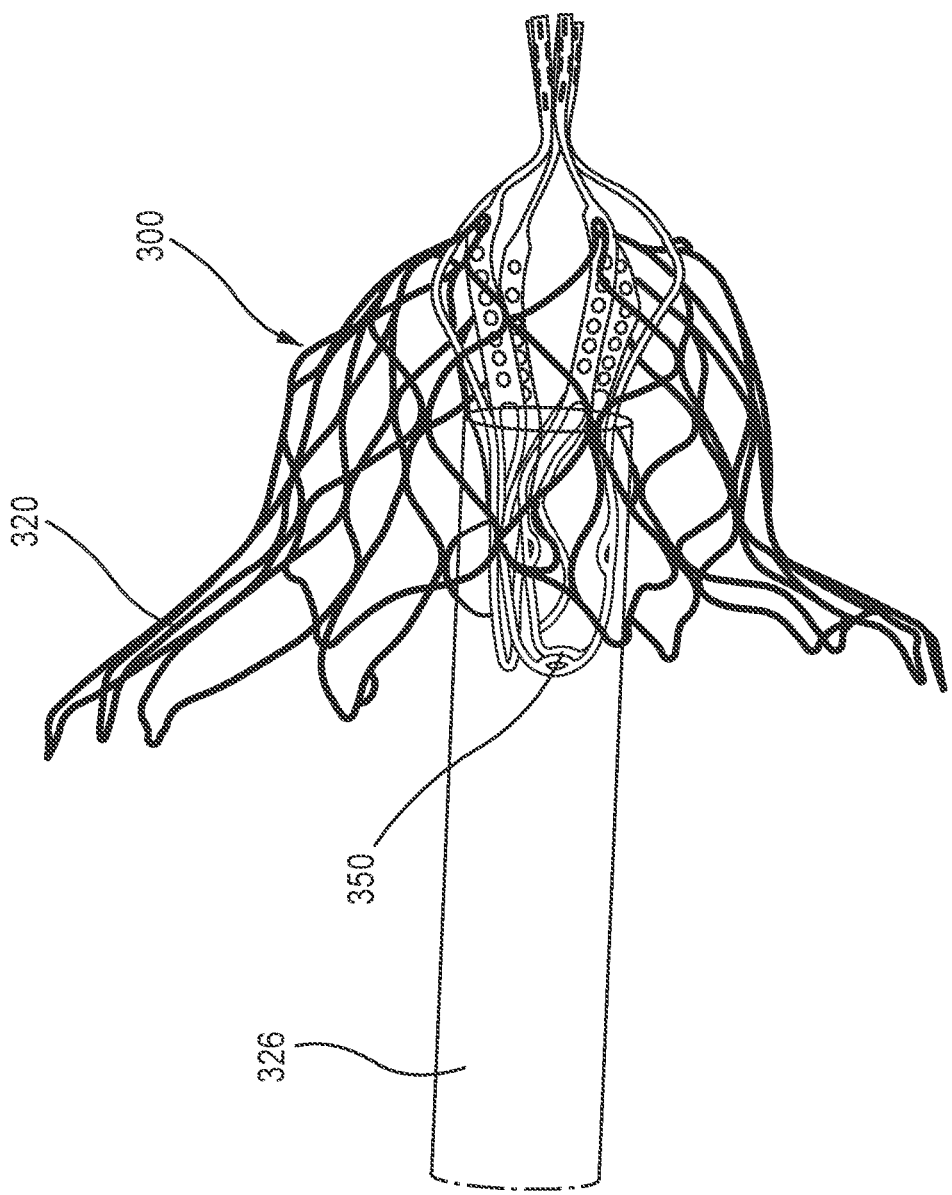
FIG. 21 is a side view of the assembly of FIG. 17 shown in a fourth partially deployed configuration in which the outer frame has reverted and assumed a biased expanded configuration.

As the valve 300 exits the lumen of the delivery sheath 326, the outer frame assembly 310 exits first in its inverted configuration as shown in the progression of FIGS. 18-20 (see also FIG. 22). After the outer frame assembly 310 is fully outside of the lumen of the delivery sheath 326, the outer frame 320 can revert to its expanded or deployed configuration as shown in FIGS. 21, 23 and 24. In some embodiments, the outer frame 320 can revert automatically after fully exiting the lumen of the delivery sheath due to its shape-memory properties. In some embodiments, a component of the delivery sheath or another device can be used to aid in the reversion of the outer frame assembly 310. In some embodiments, the pusher device and/or the tether can be used to aid in the reversion of the outer frame assembly 310. The valve 300 can continue to be deployed until the inner frame 350 is fully deployed with the left atrium and the valve 300 is in the expanded or deployed configuration (as shown, e.g., in FIGS. 15 and 24). The valve 300 and the tether 336 can then be secured to the apex of the heart with an epicardial pad device 339 as shown in FIG. 24 and as described in more detail in the '572 PCT application and the '305 PCT application.

Figure 25:
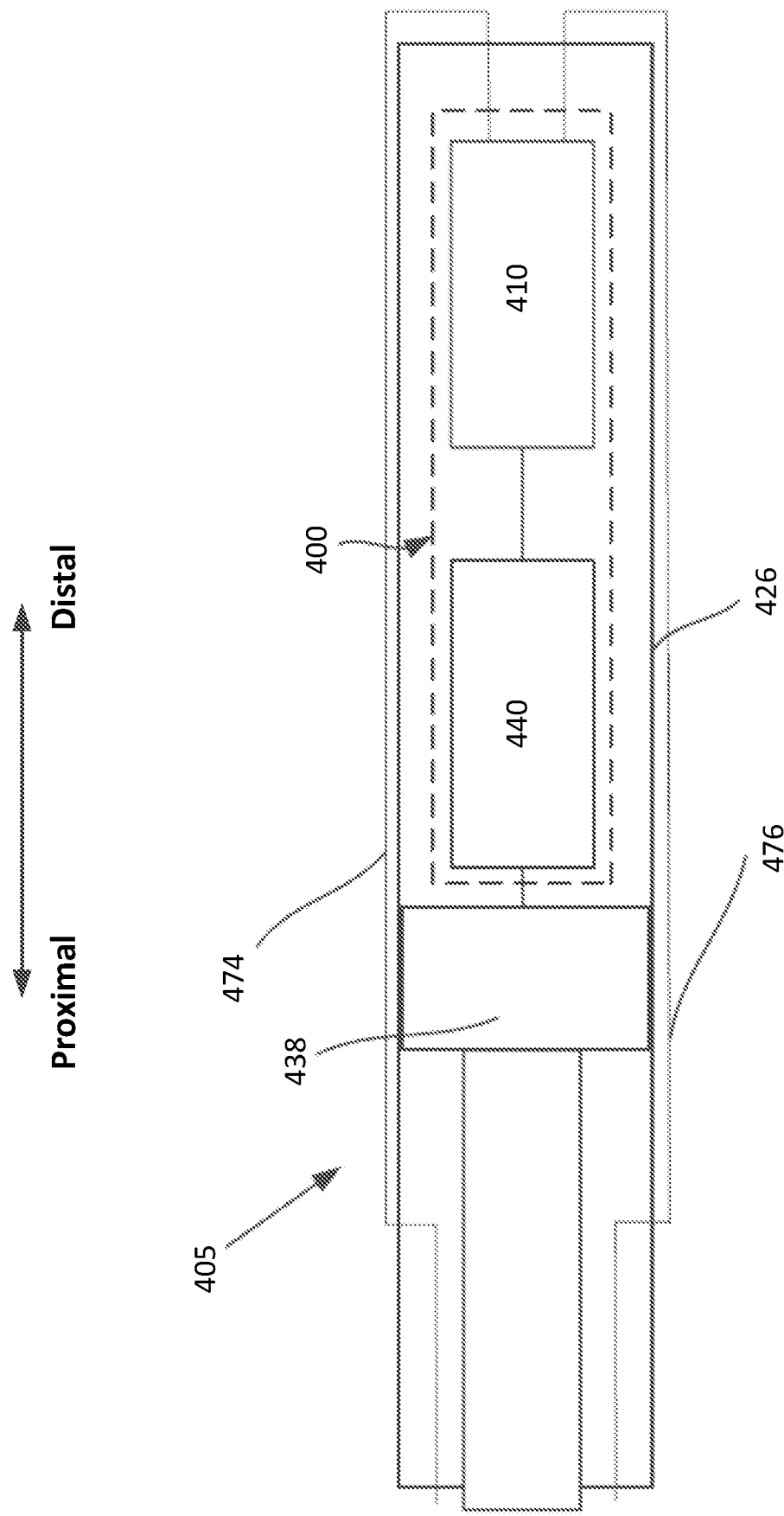
FIG. 25 is a schematic illustration of a delivery device and prosthetic heart valve, according to an embodiment.

FIG. 25 illustrates schematically another embodiment of a delivery system that can be used to delivery and deploy a prosthetic heart valve within a heart of a patient with, for example, a transvascular approach. In this embodiment, a delivery system 405 includes a delivery sheath 426, a valve holder 438 (also referred to as a "pusher"), and one or more actuation wires 474 and 476. In this schematic illustration, only two actuation wires are illustrated, but in other embodiments, only one actuation wire or more than two actuation wires can be used.

Figure 26B:
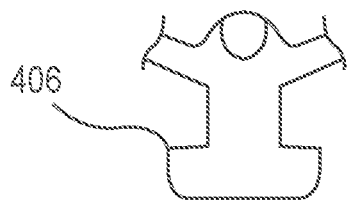
FIG. 26B is a side view of an attachment member of the prosthetic valve of FIG. 26A.
Figure 26A:
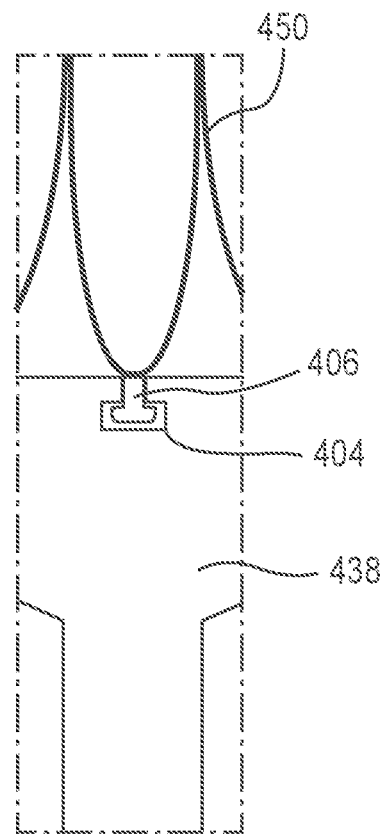
FIG. 26A is a side view of a portion of the prosthetic heart valve of FIG. 25 shown within a delivery sheath and coupled to a valve holder.
Figure 26C:
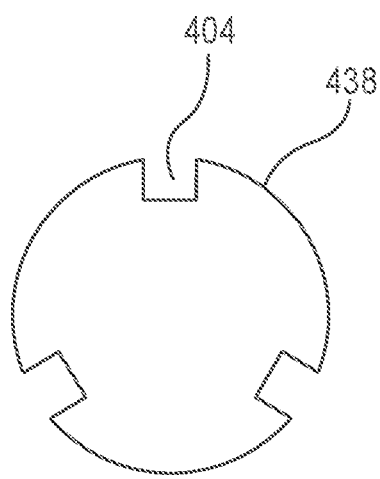
FIG. 26C is an end view of the valve holder of FIG. 26A.

The delivery sheath 426 can be used to deliver a valve 400 that includes an inner valve assembly 440 including an inner frame (not labeled in FIG. 25) and an outer frame assembly 410 including an outer frame (not labeled in FIG. 25). The valve 400 can be constructed the same as or similar to, and function the same as or similar to, for example, any of the prosthetic valves described herein and/or in the '305 PCT Application, and can be moved between a deployed or expanded configuration and a delivery configuration in which the outer frame is disposed in an inverted positon relative to the inner frame as described herein and/or in the '305 PCT Application. As shown in FIG. 25, the valve 400 can be disposed within a lumen of the delivery sheath 426 when the valve is in the delivery configuration (i.e., the outer frame is inverted relative to the inner frame). In this embodiment, when in the delivery configuration and placed within a delivery sheath, the outer frame assembly 410 is disposed distal of the inner valve assembly 440. The valve holder 438 is coupled to the inner valve assembly 440 and the actuation wires are coupled to the outer fame assembly 410. The valve holder 438 can be releasably coupled to the inner valve assembly 440 via couplers 406 that are attached to the inner valve assembly 440 as shown in FIGS. 26A-26C. In this embodiment, the couplers 406 are in the form of a T-bar or hammer shape. It should be understood that couplers with other configurations and shapes can be used.

As shown in FIG. 26A, the couplers 406 are received within the recesses 404 and the valve 400 and the valve holder 438 can be disposed within the lumen of the delivery sheath 426. The inner diameter of the delivery sheath 426 can be sized such that when the valve holder 438 and valve 400 are disposed therein, the couplers 406 are unable to exit the recesses 404. In other words, the inner walls of the delivery sheath 426 maintain the couplers 406 within the recesses 404. When the valve 400 is moved outside of the delivery sheath 426, the couplers 406 will be able to freely exit the recesses 404 releasing the inner frame 450 from the valve holder 438.

In alternative embodiments, the valve holder 438 can be removably coupled to the valve 400 (e.g., the inner frame 450 of the valve 400) via wires or sutures that can be cut after delivery of the valve 400 to the heart. In some cases, the valve holder 438 can be decoupled from the valve 400 when the valve is still disposed within the delivery sheath 426, while in other instances the valve holder 438 can be decoupled from the valve 400 after the valve 400 exits the delivery sheath 426 within the heart.

The actuation wires 474 and 476 can be coupled to the outer frame of the outer frame assembly 410 with a variety of different coupling methods. For example, the outer frame 410 can include loops (as described herein with respect to outer frame 510, outer frame 1010, and in the '305 PCT Application) through which the actuation wires 474 and 476 can be received or threaded. The number of loops on the outer frame can vary and the number of loops through which each actuation wire is connected can vary. For example, in some embodiments, the outer frame includes 12 loops and a first actuation wire is threaded through 6 of the loops and a second actuation wire is threaded through 6 of the loops. In other embodiments, the outer frame can include 12 loops and there can be 4 actuation wires, each coupled to 3 of the loops. In some embodiments, a single actuation wire is coupled through all of the loops of the outer frame.

In this embodiment, the delivery sheath 426 can be used to deliver the valve 400 to the left atrium of the heart using a transvascular approach (e.g., transfemoral, transatrial, transjugular). When the distal end of the delivery sheath 426 is disposed within the left atrium, the valve 400 is moved out of the lumen of the delivery sheath 426 using the actuation wires 474, 476 to assist in pulling the valve 400 out of the delivery sheath 426. In some cases, the valve holder 438 can also be used to push the valve 400 out of the delivery sheath 426. More specifically, the actuation wires 474 and 476 can extend from the outer frame assembly 410 out a distal end of the delivery sheath and extend proximally. In some embodiments, the actuation wires 474, 476 extend proximally outside the delivery sheath 426, then pass back into the lumen of the delivery sheath 426 through side apertures or holes (not shown) and then out a proximal end of the delivery sheath 426. Thus, a user (e.g., physician) can pull the proximal end portions of the actuation wires 474 and 476 to in turn pull the outer frame assembly 410 out of the distal end of the delivery sheath 426. In some embodiments, the actuation wires 474, 476 extend proximally from the outer frame assembly 410, back through the distal end of the delivery sheath 426 (e.g., rather than through side apertures or holes of the delivery sheath) and within the lumen of the delivery sheath, and then out a proximal end of the delivery sheath 426. Various different embodiments and configurations are described in more detail below.

As the outer frame assembly 410 exits the delivery sheath 426 it will still be in an inverted configuration relative to the inner valve assembly 440. After the outer frame assembly 410 is at least partially outside of the lumen of the delivery sheath 426, the outer frame assembly 410 can begin to revert to its expanded or deployed configuration (not shown in FIG. 25). In this embodiment, however, the actuation wires 474 and 476 can function to selectively (e.g., by an operator) assist and/or control the expansion, deployment and/or articulation of the valve 400 as the valve 400 is delivered to the heart. In this manner, in use, the proximal end portions of the actuation wires 474, 476 can be pulled distally to manipulate the outer frame assembly 410 to assist and control the transition of the outer frame assembly 410 from its inverted configuration relative to the inner valve assembly 440 to its expanded or deployed configuration (not shown). In some embodiments, the actuation wires 474, 476 can be manually grasped by a user to pull the actuation wires proximally. In some embodiments, the actuation wires 474, 476 can be operatively coupled to the delivery system 405 such that the user does not have to manually handle the actuation wires. For example, the actuation wires can be coupled to a delivery sheath and/or to a handle assembly (not shown) of the delivery system 405. Various embodiments of a delivery system are described in more detail below and in the '305 PCT Application.

Figure 27:
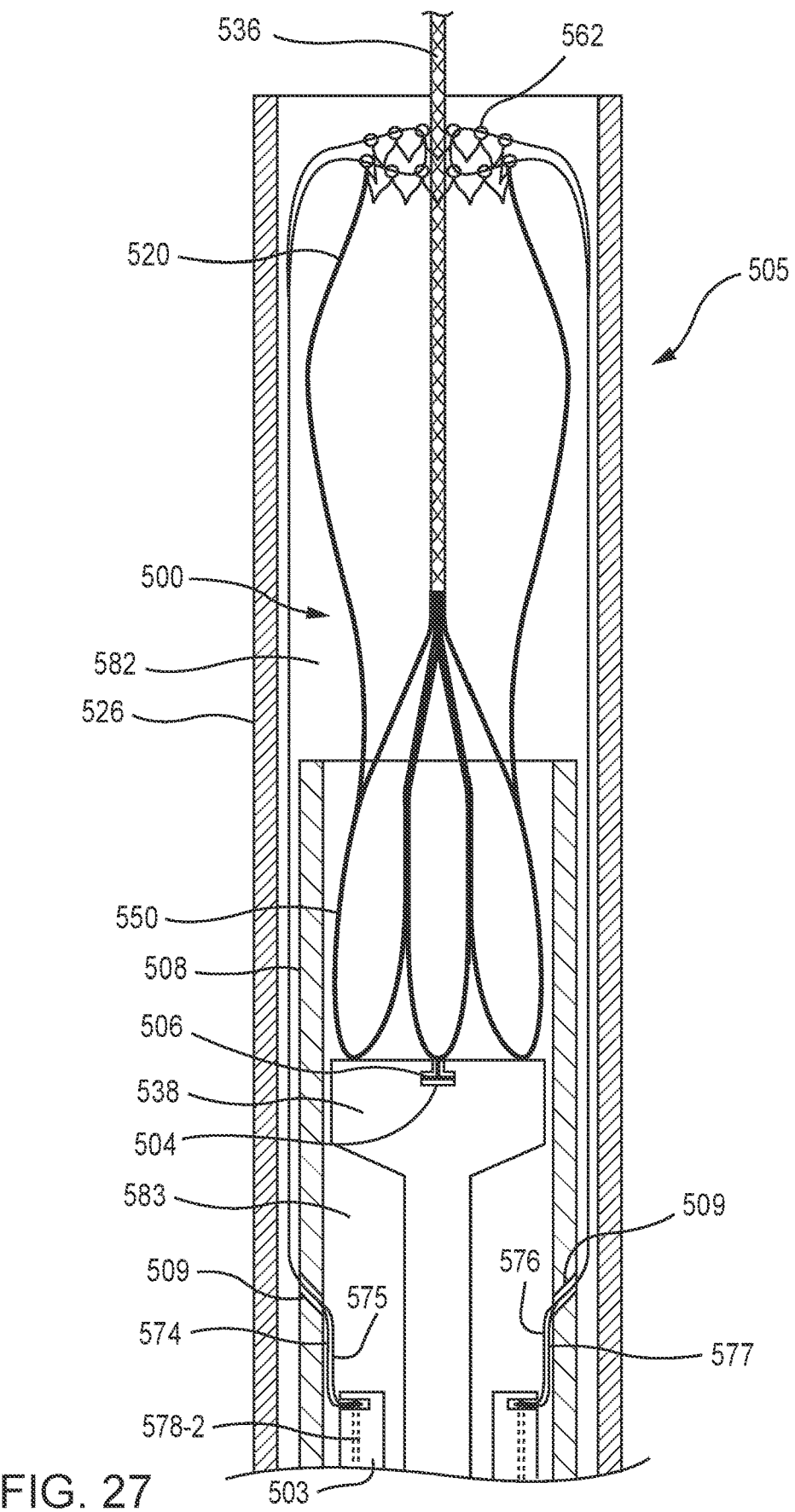
FIG. 27 is a cross-sectional side view of a prosthetic valve in an inverted configuration inside of a delivery sheath, according to an embodiment.

FIG. 27 illustrates an embodiment of a delivery system 505 that can be used to deliver and deploy a prosthetic heart valve 500 (also referred to herein as "valve") within a heart in a procedure similar to or the same as the procedures described with respect to other embodiments described herein (e.g., the embodiments illustrated in and described with respect to FIGS. 34-42) and embodiments described in the '305 PCT Application. Thus, some details regarding the valve 500 and procedures performed therewith are not described herein. It should be understood that for features and functions not specifically discussed, those features and functions can be the same as or similar to the valves described herein (e.g., the valve 1000) and/or in the '305 PCT Application. The valve 500 can be constructed the same as or similar to, and function the same as or similar to any of the valves described herein and/or in the '305 PCT Application. For example, the valve 500 includes an outer frame assembly that has an outer frame 520, an inner valve assembly 540 that has an inner frame 550, and a tether 536 coupled to the inner valve assembly. The delivery system 505 includes an outer delivery sheath 526, an inner sheath 508, a valve holder 538 (also referred to as a "pusher") and a multi-lumen elongate tube member 503 (also referred to as "tube" or "tube member" or "multi-lumen elongate member"). As shown in FIG. 27, the inner sheath 508 is movably disposed within the lumen 582 defined by the outer delivery sheath 526, and the tube member 503 is movably disposed within a lumen 583 defined by the inner sheath 508. The valve holder 538 is movably disposed the lumen 583 defined by the inner sheath 508.

As with other embodiments described herein and embodiments of the '305 PCT Application, the valve 500 can be moved from a biased expanded configuration to an inverted configuration for delivery of the valve 500 to the heart. More specifically, to place the valve 500 in the inverted configuration, the outer frame 520 can be moved to an inverted configuration relative to the inner frame 550. In this embodiment, the valve 500 is placed at least partially within the lumen of the inner sheath 508 when the valve 500 is in the inverted configuration, and disposed near a distal end of the inner sheath 508. The valve holder 538 is also disposed within the lumen 583 of the inner sheath 508. The inner frame 550 can be releasably coupled to the valve holder 538 with couplers 506 in the same or similar manner as described above with respect to couplers 406, couplers 1006, and/or any of the couplers described in the '305 PCT Application. Similarly, the outer frame 520 includes loops 562 through which actuation wires 574-577 can be threaded through in the same or similar manner as described herein (e.g., with respect to valve 1000) and/or in the '305 PCT Application. The inner sheath 508 is movably disposed within the outer delivery sheath 526. As shown in FIG. 6, a portion of the valve 500 is disposed outside of the inner sheath 508 and within the lumen 582 of the outer delivery sheath 526. In some cases, the entire valve 500 can be disposed within the lumen 583 of the inner sheath 508 prior to performing the procedure to deploy the valve.

In this embodiment, the inner sheath 508 defines side apertures 509 through which the actuation wires 574-577 can pass through. More specifically, as shown in FIG. 27, when the valve 500 is disposed within the lumen 583 of the inner sheath 508, the actuation wires 574-577 extend proximally from the outer frame 520, along the outside of the inner sheath 508 and within the lumen 582 of the outer delivery sheath 526, back through side apertures 509 defined by the inner sheath 508, within the lumen 583 of the inner sheath 508, and are pinned by an elongate pinning member 578-1, 578-2, 578-3, 578-4 (collectively referred to as pinning member 578; pinning members 578-3 and 578-4 are not shown in FIG. 27; for illustrative purposes, refer to pinning members 1078-3 and 1078-4 shown in and described with respect to FIGS. 35-37A) to the tube member 503. As shown, a first end of the actuation wire 574 and a first end of the actuation wire 575 are pinned by a pinning member 578-2, and a first end of the actuation wire 576 and a first end of the actuation wire 577 are pinned by a pinning member 578-1. A second end of the actuation wire 574 and a second end of the actuation wire 576 are pinned by a pinning member 578-4 (not shown), and a second end of the actuation wire 575 and a second end of the actuation wire 577 are pinned by a pinning member 578-3 (not shown).

The actuation wires 574-577 can be pinned to the tube member 503 by the pinning members 578-1, 578-2, 578-3, 578-4 in the same or similar manner as described below with respect to the delivery system 1005. Thus, some details regarding, for example, the tube member 503, the pinning member 578-1, 578-2, 578-3, 578-4 and the actuation wires 574-577, and procedures performed therewith, are not described with respect to this embodiment. It should be understood that for features and functions not specifically discussed with respect to this embodiment, those features and functions can be the same as or similar to the delivery systems described in herein (e.g., the delivery system 1005) and/or in the '305 PCT Application.

A user (e.g., physician) can use the tube member 503, to which the actuation wires 574-577 are coupled, to control and/or manipulate movement and/or deployment of the valve 500 as described, for example, with respect to the delivery system 1005. In this embodiment, as shown, at least a portion of the actuation wires 574-577 can be disposed within the interior of the delivery sheath 526, thus limiting the exposure of the actuation wires 574-577 to areas external to the delivery sheath 526 for at least a portion of the delivery and/or deployment of the valve 500. Although the side apertures 509 defined by the inner sheath 508 are shown as disposed at or near the distal end portion of the inner sheath 508, in other embodiments, side apertures 509 can be disposed at any suitable location along the length of the inner sheath 508 (e.g., towards a middle portion or a proximal portion of the management sheath).

In this embodiment, to deliver the valve 500 to the heart, the distal end of the outer delivery sheath 526, with the valve 500, inner sheath 508, valve holder 538, and tube member 503 disposed therein, is disposed within the left atrium of the heart. With the distal end portion of the delivery sheath 526 disposed within the left atrium of the heart, the valve 500 can be deployed outside of the delivery sheath 526. For example, the inner sheath 508, valve holder 538, and tube member 503 can be moved distally relative to the outer sheath 526, moving or pushing the valve 500 outside the lumen 582 of the outer sheath 526. In addition, or alternatively, the outer sheath 526 can be moved or pulled proximally, leaving at least a portion of the valve 500 disposed within the heart. In some instances, the tether 536 coupled to the valve 500 can be used to help pull the valve 500 out of the lumen 582 of the outer sheath 526.

Figure 40:
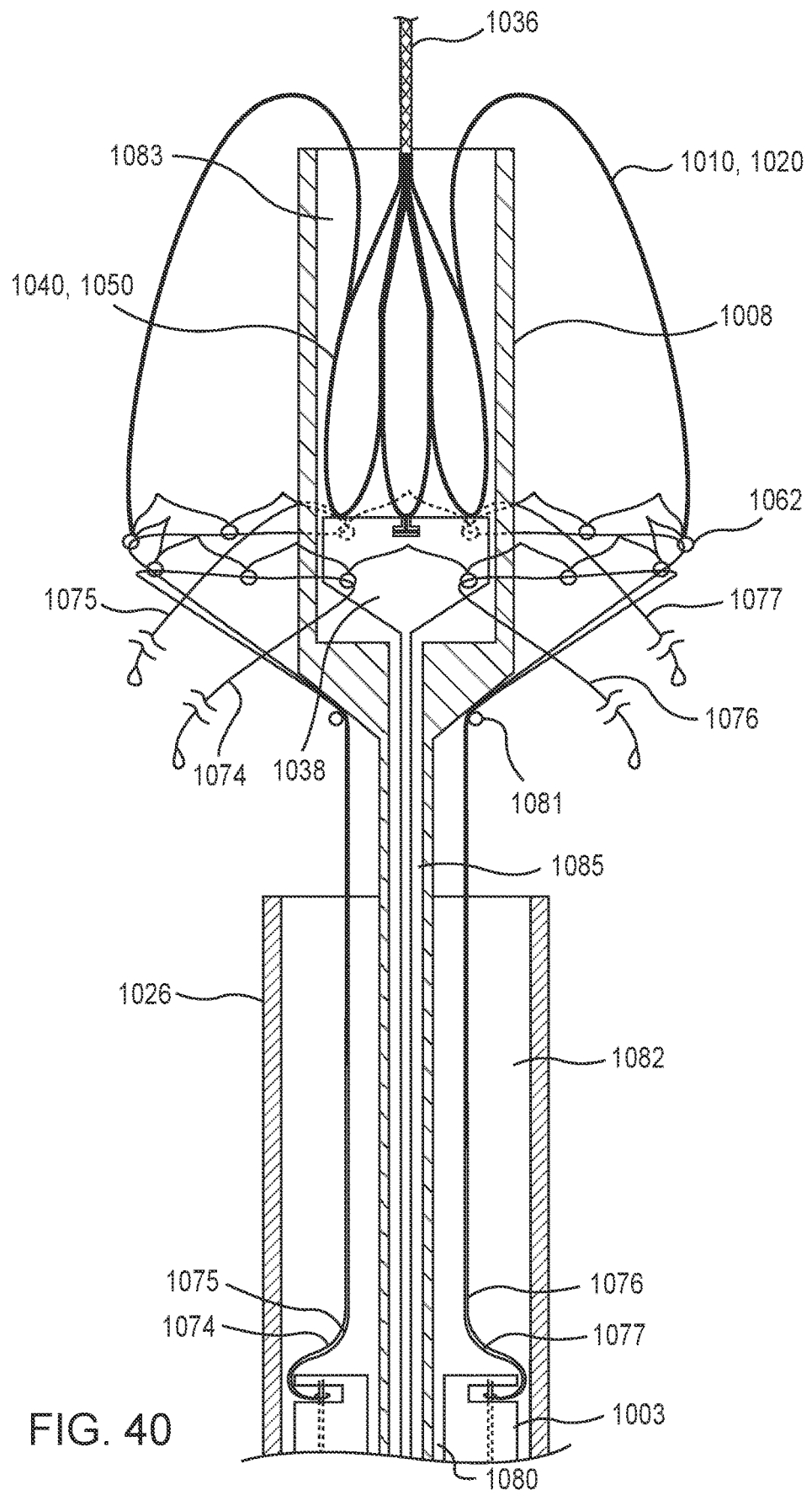
FIG. 40 is a partial cross-sectional side view of the delivery system and prosthetic heart valve of FIG. 34, shown in a second partially deployed configuration.

As described in other embodiments herein and embodiments of the '305 PCT Application, as the outer frame 520 becomes unconstrained by the outer sheath 526, the outer frame 520 can begin to revert to its expanded or uninverted configuration. The actuation wires 575-577 can be used to control the reversion of the outer frame 520. More specifically, after the outer frame 520 is disposed at least partially outside the distal end of the outer sheath 526, the tube member 503 can be pulled proximally such that the actuation wires (pinned to the tube member 503) pull the distally disposed portion of the outer frame 520 proximally (the same as or similar to as shown in FIG. 40) in a controlled manner and such that the reversion of the outer frame 520 from its inverted configuration relative to the inner frame 550 can be controlled.

Figure 41:
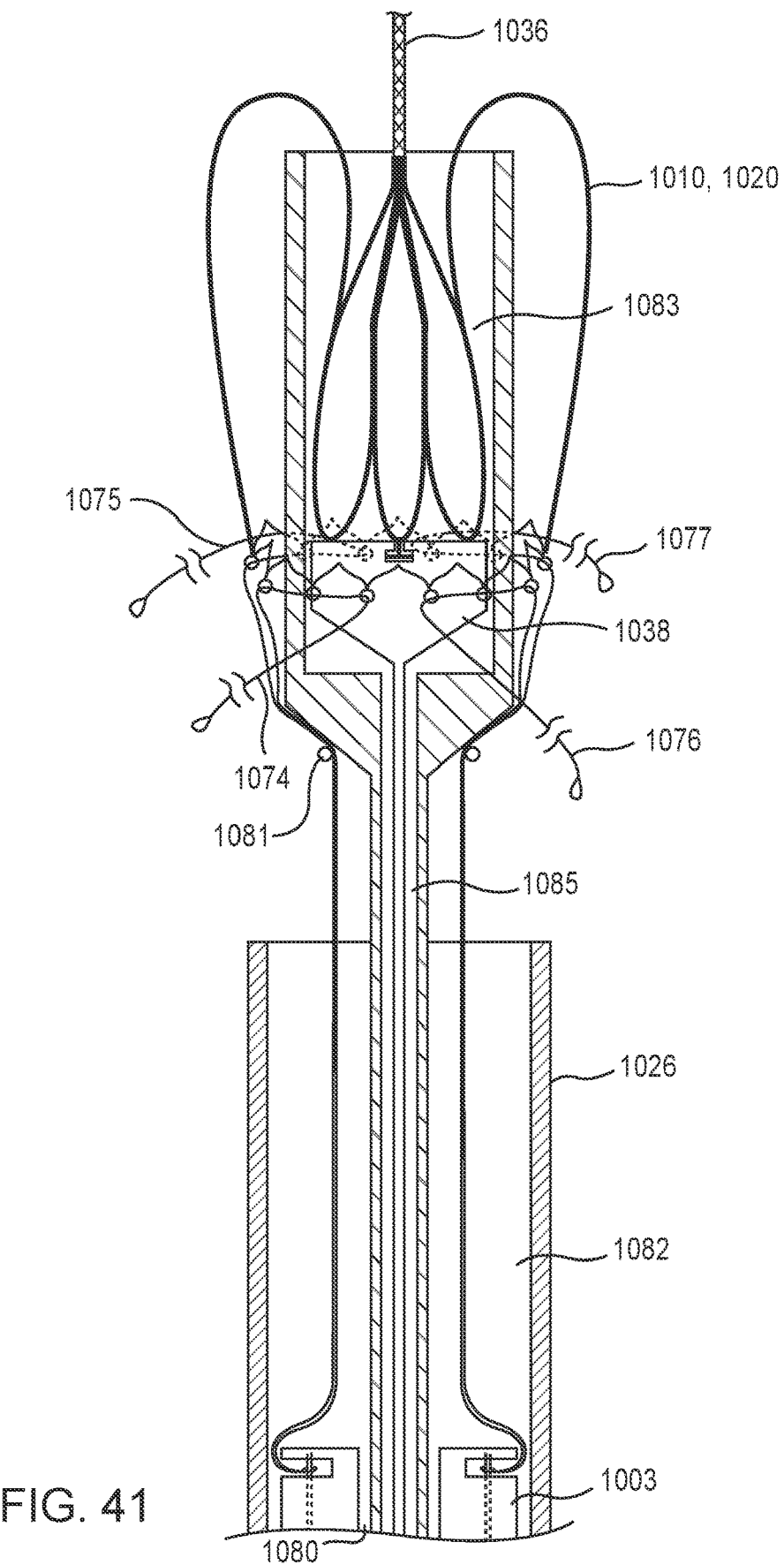
FIG. 41 is a partial cross-sectional side view of the delivery system and prosthetic heart valve of FIG. 34, shown in a third partially deployed configuration.

In addition, in some instances, the actuation wires 574-577 can assist in the articulation and placement of the valve 500 into its destination (e.g., a native annulus of an atrio-ventricular valve of a heart). For example, the actuation wires 574-577 can also be used to constrain, collapse, or otherwise move the valve 500 (e.g., radially compress the outer frame 520 of the valve 500) after the valve 500 exits the outer sheath 526 and is in its reverted, expanded or partially expanded configuration. More specifically, in this embodiment, the tube member 503 with the actuation wires 574-577 pinned thereto, can be manipulated by a user to move or urge the outer frame 520 to a more compressed configuration (similar to or the same as shown in FIG. 41) by pulling or moving the tube member 503 proximally. This may be desirable, for example, to reposition the valve 500 within the heart before fully deploying the valve 500.

With the outer frame 520 of the valve 500 disposed in its non-inverted and at least partially expanded configuration, and in a desired positon within the heart, the inner frame 550 can be deployed. As described in the '305 PCT Application with respect to valve 2100, to decouple the inner frame 550 from the valve holder 538, the valve holder 538 can be moved distally and/or the inner sheath 508 can be moved proximally such that the valve holder 538 is disposed outside of the lumen 583 of the inner sheath 508. As such, the couplers 506 can be released from the recesses 504, releasing or decoupling the inner frame 550 from the valve holder 538. In some embodiments, the tether 536 can be pulled to help move the inner frame 550 outside of the inner sheath 508. When the inner frame 550 is released from the valve holder 538 and disposed outside the inner sheath 508, the inner frame 550 can assume its biased expanded configuration.

The actuation wires 574-577 can also be released or decoupled from the outer frame 520 before or after the inner frame 550 is released form the valve holder 538. To decouple the actuation wires 574-577 from the outer frame 520, one end of each of the actuation wires 574-577 can be unpinned or decoupled from the tube member 503. For example, the pinning member 578-3 can be withdrawn proximally from a groove of the tube member 503 (the same as or similar to the groove 1084 shown in and described with respect to the delivery system 1005) such that the second end of the actuation wire 577 and the second end of the actuation wire 575 are each released or unpinned from the tube member 503, but remain pinned by pinning members 578-2 and 578-1, respectively. Similarly, the pinning member 578-4 can be withdrawn proximally from the groove such that the second end of the actuation wire 574 and the second end of actuation wire 576 can each be released or unpinned from the tube member 503, but remain pinned by pinning members 578-2 and 578-1, respectively. With one end of each of the actuation wires 575-577 coupled to the tube member 503 (via pinning members 578-1 and 578-2 in this example), the tube member 503 can be pulled proximally, which in turn will pull the opposite ends of the actuation wires 574-577 out of the loops 562 of outer frame 520. Thus with the actuation wires 574-577 detached from the outer frame 520, the outer frame can assume a biased expanded or partially expanded configuration.

Although in the above example, the pinning members 578-3 and 578-4 are described as being withdrawn to release the ends of the actuation wires 574-577, alternatively, the pinning members 578-1 and 578-2 can be withdrawn leaving the actuation wires 574-577 pinned by pinning members 578-3 and 578-4. Further, the actuation wires 574-577 can be decoupled from the outer frame 520 at any suitable sequence or time period within the procedure. For example, in some instances it may be desirable for the actuation wires 574-577 to be released after the valve 500 has at least partially exited the delivery sheath 526 but before the valve 500 is seated within the native annulus of the atrioventricular valve. In other instances, for example, the actuation wires 574-577 can be released after the valve 500 has at least partially exited the outer delivery sheath 526 and after the valve 500 is seated within the native annulus of the atrioventricular valve.

Figure 28:
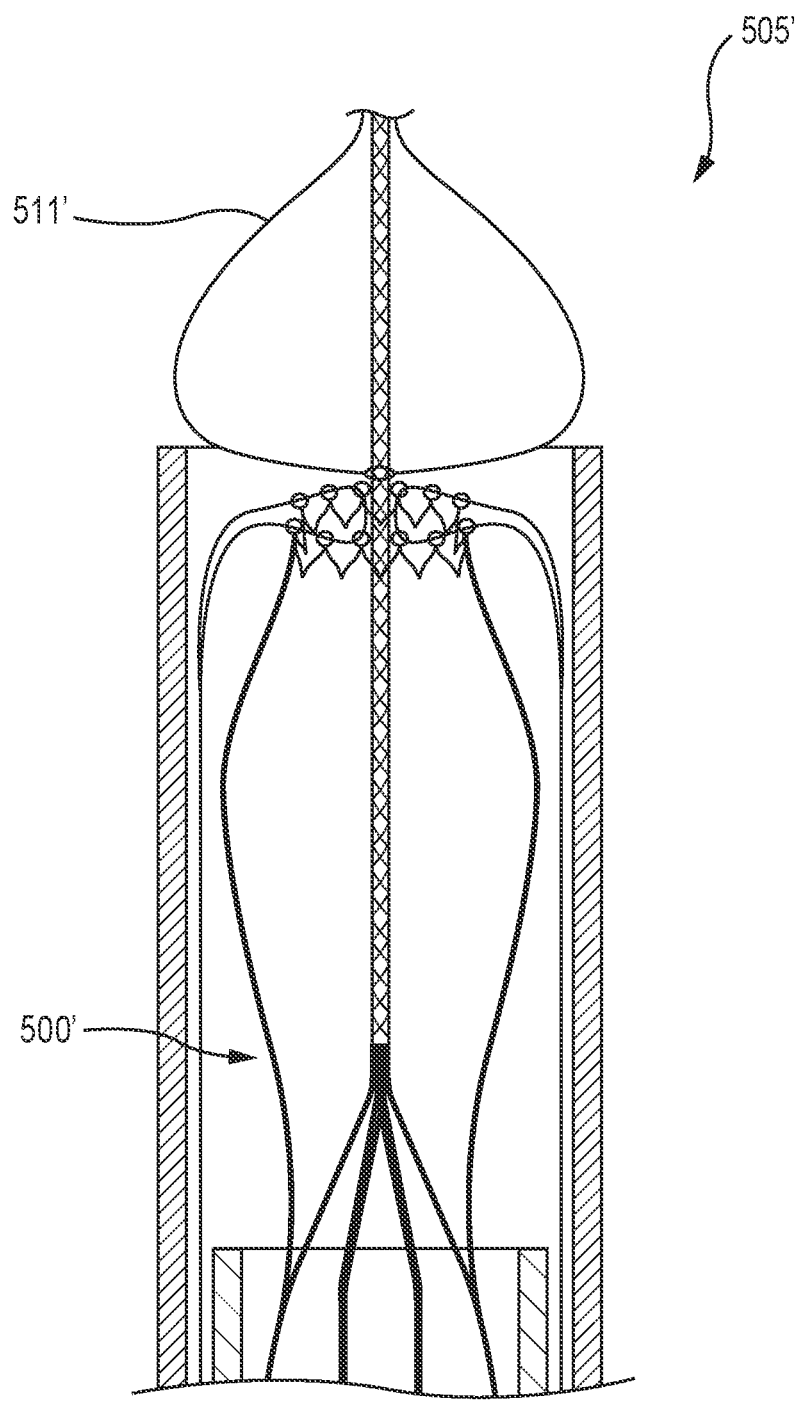
FIG. 28 is a portion of a cross-sectional side view of a prosthetic valve in an inverted configuration inside of a delivery sheath, including a dilator, according to an embodiment.

In some instances, for example as shown in FIG. 28, a delivery system 505' can include a dilator device or member 511'. The dilator 511' can be, for example, a balloon dilator and can be configured to expand an opening or passage, for example, during delivery of the prosthetic valve 500'. The dilator device 511' can be the same as or similar to the dilator device 1711 and used in the same or similar manner as described in the '305 application with respect to FIGS. 43-48 and the method of delivery of FIG. 72. Delivery system 505' can include the same as or similar features, and function the same as or similar to, for example, the delivery system 505 and/or the delivery system 1005 described herein and/or delivery systems described in the '305 PCT Application.

In some embodiments, a prosthetic heart valve (e.g., any prosthetic heart valve described herein and/or in the '305 PCT Application) can include an outer frame having multiple rows of loops through which any suitable number of actuator wires can be routed and/or slidably disposed (e.g., to control the reversion profile and timing of the outer frame as it is deployed and delivered from a delivery sheath). FIGS. 29A and 29B illustrate such an embodiment of a prosthetic heart valve 600 and a delivery system 605 that can be used to deliver and deploy the prosthetic heart valve 600 (also referred to herein as "valve") within a heart in a procedure similar to or the same as the procedures described herein with respect to other embodiments and embodiments described in the '305 PCT Application. Thus, some details regarding the valve 600 and procedures performed therewith are not described herein. It should be understood that for features and functions not specifically discussed, those features and functions can be the same as or similar to the valves and/or delivery system components described herein and/or in the '305 PCT Application. For example, the valve 600 can be constructed the same as or similar to, and function the same as or similar to any of the valves described herein and/or in the '305 PCT Application. For example, the valve 600 includes an outer frame assembly that has an outer frame 620, and an inner valve assembly that has an inner frame 650. As shown in FIGS. 29A and 29B, the delivery system 605 includes an outer delivery sheath 626. The delivery system 605 can also include other components and features not shown in FIGS. 29A and 29B, such as, for example, an inner sheath similar to inner sheath 508, a valve holder similar to valve holder 538 described herein, and/or any other suitable components and/or features described with respect to other embodiments herein and in the '305 PCT Application.

As with other embodiments described herein and embodiments of the '305 PCT Application, the valve 600 can be moved from a biased expanded configuration to an inverted configuration for delivery of the valve 600 to the heart, as shown in FIG. 29A. In this embodiment, the valve 600 is positioned for transvascular delivery similar to as described for valve 500 above. Thus, when disposed in the inverted configuration within the sheath 626, the outer frame is disposed distal of the inner frame. In this embodiment, the outer frame 620 includes a first row of loops 662 and a second row of loops 664, through which actuation wires 674-679 can be threaded through in the same or similar manner as described herein with respect to valve 400 and/or valve 1000 and/or in the '305 PCT Application with respect to valve 2100.

In this embodiment, the actuation wires 674-679 extend proximally from the outer frame 620, within the lumen 682 of the outer delivery sheath 626, and out the proximal end of the outer delivery sheath 626. In alternative embodiments, the actuator wires 674-679 can be pinned to a tube member by pinning members (not shown in FIGS. 29A and 29B) in the same or similar manner as described herein with respect to the delivery system 505 and/or the delivery system 1005.

In this embodiment, to deliver the valve 600 to the heart, the distal end of the outer delivery sheath 626, with the valve 600 disposed therein, is disposed within the left atrium of the heart. With the distal end portion of the outer delivery sheath 626 disposed within the left atrium of the heart, the valve 600 can be deployed outside of the outer sheath 626. For example, the valve 600 can be moved distally relative to the outer sheath 626 outside the lumen 682 of the outer sheath 626. In addition, or alternatively, the outer sheath 626 can be moved or pulled proximally, leaving at least a portion of the valve 600 disposed within the heart. In some embodiments, a tether (not shown) coupled to the valve 600 can be used to help pull the valve 600 out of the lumen 682 of the outer sheath 626.

As described in previous embodiments and embodiments of the '305 PCT Application, as the outer frame 620 becomes unconstrained by the outer sheath 626, the outer frame 620 can begin to revert to its expanded or uninverted configuration. The actuation wires 674-679 can be used to control the reversion of the outer frame 620. More specifically, after the outer frame 620 is disposed at least partially outside the distal end of the outer sheath 626, the proximal ends of the actuator wires 674-679 can be pulled proximally, which will in turn pull the open end of the outer frame 620 (to which the actuation wires 674-679 are coupled) distally to help revert the outer frame 620. For example, as described with respect to other embodiments herein and in the '305 PCT Application, a user (e.g., a physician) can pull the end portions of the actuator wires 674-679 to in turn move the outer frame 620 to its reverted configuration, as shown in FIG. 29B. Similarly stated, the actuation wires (coupled to the outer frame 620) pull the distally disposed portion of the outer frame 620 proximally (the same as or similar to as shown in FIG. 40) in a controlled manner and such that the reversion of the outer frame 620 from its inverted configuration relative to the inner frame 650 can be controlled. Having multiple rows of loops (e.g., the first row of loops 662 and the second row of loops 664), as shown and described with respect to this embodiment, provides increased control of the reversion of the outer frame 620 from its inverted configuration.

In this embodiment, the outer frame 620 has two rows of loops, each row having 12 loops. In alternative embodiments, however, an outer frame can have any suitable number of loops and/or rows of loops such that the outer frame 620 can be reverted in a controlled manner. For example, in some alternative embodiments, an outer frame can have 3 or more rows of loops. Further, in some embodiments, the loops can be integrally or monolithically formed with the outer frame, while in other embodiments, one or more of the loops can be formed separately from and coupled to the outer frame (e.g., sewn onto the outer frame).

In addition, in some instances, the actuation wires 674-679 can assist in the articulation and placement of the valve 600 into its destination (e.g., a native annulus of an atrioventricular valve of a heart). For example, the actuation wires 674-679 can also be used to constrain, collapse, or otherwise move the valve 600 (e.g., radially compress the outer frame 620 of the valve 600) after the valve 600 exits the outer sheath 626 and is in its reverted, expanded or partially expanded configuration.

With the outer frame 620 of the valve 600 disposed in its non-inverted and at least partially expanded configuration (see e.g., FIG. 29B), and in a desired positon within the heart, the inner frame 650 can be deployed and allowed to assume its biased expanded configuration. The actuation wires 674-679 can also be released or decoupled from the outer frame 620 before or after the inner frame 650 is deployed. To decouple the actuation wires 674-679 from the outer frame 620, one end of each of the actuation wires 674-679 can be pulled proximally, which in turn will pull the opposite ends of the actuation wires 674-679 out of the loops 674-679 of the outer frame 620. With the actuation wires 674-679 detached from the outer frame 620, the outer frame can assume a biased expanded or partially expanded configuration.

In some instances, the actuation wires 674-679 can be decoupled from the outer frame 620 at any suitable sequence or time period within the procedure. For example, in some instances it may be desirable for the actuation wires 674-677 to be released after the valve 600 has at least partially exited the delivery sheath 626 but before the valve 600 is seated within the native annulus of the atrioventricular valve. In other instances, for example, the actuation wires 674-679 can be released after the valve 600 has at least partially exited the outer delivery sheath 626 and after the valve 600 is seated within the native annulus of the atrioventricular valve.

The embodiments described above and in the '305 PCT Application are described for use in transfemoral delivery. In other embodiments, similar delivery devices and methods can be used for transapical delivery of a prosthetic heart valve. The following apparatus and methods are described herein for use in transapical delivery and deployment of prosthetic heart valves, such as prosthetic mitral valves, that can be configured to be moved to an inverted configuration for delivery of the prosthetic valve to within a heart of a patient. As described herein, in some embodiments, a prosthetic valve includes an outer frame that can be inverted relative to an inner frame when the prosthetic valve is in a biased expanded configuration. The prosthetic mitral valve can be formed with, for example, a shape-memory material. After inverting the outer frame, the prosthetic valve can be inserted into a lumen of a delivery sheath such that the prosthetic valve is moved to a collapsed configuration.

The delivery sheath can be used to deliver the prosthetic valve to within a patient's heart using a variety of different delivery approaches for delivering a prosthetic heart valve (e.g., a prosthetic mitral valve) where the inverted prosthetic valve would enter the heart through the ventricle of the heart and into the atrium of the heart. For example, as described in further detail herein with respect to FIGS. 30A-30D and FIGS. 31A and 31B, an inverted prosthetic valve can be delivered using an apical approach, i.e., delivered through the apex of the left ventricle of a heart.

After the delivery sheath has been disposed within the left atrium of the heart (e.g., via an apical approach), the prosthetic mitral valve is moved distally out of the delivery sheath such that the inverted outer frame reverts and the prosthetic valve assumes its biased expanded configuration. The prosthetic mitral valve can then be positioned within a mitral annulus of the heart.

FIGS. 30A and 30B are schematic illustrations of a portion of a prosthetic heart valve 700, according to an embodiment, shown in a first configuration and a second configuration respectively, and FIGS. 30C and 30D illustrate the portions of the prosthetic heart valve 700 of FIGS. 30A and 30B, respectively, shown disposed within a lumen of a delivery sheath 726' and 726, respectively. FIGS. 31A and 31B illustrate a portion of the prosthetic heart valve 700 in the first configuration and second configuration of FIGS. 30A and 30B, respectively, and show length dimensions for the prosthetic heart valve in each of the first configuration and the second configuration. The prosthetic heart valve 700 (also referred to herein as "prosthetic valve" or "valve") can be, for example, a prosthetic mitral valve. The valve 700 includes an outer frame 720 and an inner frame 750. The outer frame 720 and the inner frame 750 are each formed as a tubular structure similar to as described in more detail above with respect to previous embodiments and/or with reference to the prosthetic valves in the '305 PCT Application. The outer frame 720 and the inner frame 750 can be coupled together at multiple coupling joints 746 disposed about a perimeter of the inner frame 750 and a perimeter of the outer frame 720. The valve 700 can also include other features, such as any of those described herein and/or in the '305 PCT Application. For illustration purposes, only the inner frame 750 and the outer frame 720 are discussed with respect to FIGS. 30A-31B. The various characteristics and features of valve 700 described with respect to FIGS. 30A-31B can apply to any of the prosthetic valves described herein.

The outer frame 720 is configured to have a biased expanded or undeformed shape and can be manipulated and/or deformed (e.g., compressed or constrained) and, when released, return to its original (expanded or undeformed) shape. For example, the outer frame 720 can be formed of materials, such as metals or plastics, that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used. The inner frame 750 can be formed from a laser-cut tube of Nitinol®. The inner frame 750 can also have a biased expanded or undeformed shape and can be manipulated and/or deformed (e.g., compressed and/or constrained) and, when released, return to its original (expanded or undeformed) shape.

The valve 700 can be delivered and deployed within a left atrium of a heart using a variety of different delivery approaches including, for example, a transapical delivery approach, as described in more detail below, or, for example, a transatrial, transjugular or transfemoral approach. As described above, in some situations, such as when delivering a prosthetic valve to the heart via a transapical approach, it may be desirable to use a delivery sheath with a relatively small lumen, and therefore, the size of the prosthetic valve during delivery should be sized accordingly. Thus, it is desirable to have a prosthetic valve that can be reconfigured between a biased expanded configuration for implantation in the heart (e.g., within a native mitral annulus) and a delivery configuration that has a smaller outer perimeter or profile to allow for delivery within the lumen of the delivery sheath. The prosthetic valve 700 and the embodiments of a prosthetic valve described herein can be constructed and formed to achieve these desired functions and characteristics.

More specifically, the valve 700 can have a biased expanded configuration (as shown in FIGS. 30A and 31A), an inverted configuration (as shown in FIGS. 30B and 31B), and a compressed or collapsed configuration (as shown in FIGS. 30C and 30D). The expanded configuration allows the valve 700 to function when implanted within the heart. The valve 700 can be moved to the inverted configuration and the compressed or collapsed configuration for delivery of the valve 700 to the heart of a patient.

To enable the valve 700 to be moved to the inverted configuration, the outer frame 720 can be coupled to the inner frame 750 in such a manner to allow the outer frame 720 to move relative to the inner frame 750. More specifically, the coupling joints 746 can couple the outer frame 720 to the inner frame 750 in such a manner to allow the outer frame 720 to be moved relative to the inner frame 750. For example, in some embodiments, the coupling joints 746 can be configured to allow the outer frame 720 to rotate about the coupling joint 746 relative to the inner frame 750. In some embodiments, coupling joints can provide a pivotal coupling between the outer frame 720 and the inner frame 750. In some embodiments, the coupling joints can provide a flexible attachment between the outer frame 720 and the inner frame 750. The coupling joints 746 can be a variety of different types and configurations as described in the '305 application incorporated herein with reference to the various embodiments of a prosthetic valve. For example, the coupling joints 746 can include a living hinge, a flexible member, sutures, a suture wrapped through an opening, a pin or tab inserted through an opening or any combinations thereof.

To move the valve 700 from the expanded configuration (FIG. 30A) to the inverted configuration (FIG. 30B), the outer frame 720 is moved to a prolapsed or inverted configuration relative to the inner frame 750, as shown in FIGS. 30B, 30D and 31B, by moving (e.g., rotating, pivoting, flexing) the outer frame 720 about the coupling joints 746. The elastic or superelastic structure of outer frame 720 of valve 700 also allows the outer frame 720 to be moved to, and disposed in, the prolapsed or inverted configuration relative to the inner frame 750. To move the outer frame 720 to the inverted configuration relative to the inner frame 750, the outer frame 720 is folded or inverted proximally (to the right in FIG. 30B) relative to the inner frame 750 via the coupling joints 746. As shown in FIGS. 30A and 31A, the outer frame 720 is in a first position relative to the inner frame 750 prior to being inverted in which an open or free end portion 716 (also referred to the atrium portion 716 of the outer frame 720) is disposed distally or to the left of the coupling joints 746 and in the same direction as a free end portion 747 (also referred to as a second end portion of the inner frame) of the inner frame 750. When the outer frame 720 is moved to an inverted configuration (i.e., second positon relative to the inner frame 750), the free end portion 716 is disposed proximally of the coupling joints 746 (or to the right in FIGS. 30B and 31B) and in an opposite direction as the free end portion 747 of the inner frame 750. Said another way, when the valve 700 is in a biased expanded configuration (e.g., FIG. 30A), the coupling joints 746 are disposed between a first end portion 744 (also referred to as a tether coupling portion) of the inner frame 750 and the free end portion 716 of the outer frame 720. When the valve 700 is in the inverted configuration (e.g., FIG. 30B) (i.e., the outer frame 720 has been moved to an inverted configuration or position), the coupling joints 746 are disposed between the free end portion or second end portion 747 of the inner frame 750 and the free end portion 716 of the outer frame 720.

When in the inverted configuration, an overall length of the valve 700 is increased, but a length of the inner frame 750 and a length of the outer frame 720 remains the same (or substantially the same). For example, as shown in FIGS. 31A and 31B an overall length L1 of the valve 700 in the biased expanded configuration (prior to being inverted as shown in FIG. 31A) is less than the overall length L2 of the valve 700 when in the inverted configuration (FIG. 31B). A length Li of the inner frame 750 and a length Lo of the outer frame 720 is substantially the same (or the same) when the valve 700 is in both the biased expanded configuration and the inverted configuration. In addition, in some instances, depending on the specific configuration of the outer frame, an overall outer perimeter or outer diameter of the valve 700 can be smaller when the valve 700 is in the inverted configuration.

With the valve 700 in the inverted configuration, the valve 700 can be placed within a lumen of the delivery sheath 726 for delivery of the valve 700 to the left ventricle and left atrium of the heart, as shown in FIG. 30D. When placed within the lumen of the delivery sheath 726, the valve 700 is moved to the collapsed or compressed configuration in which the outer diameter or outer perimeter of the valve 700 is reduced. Because the valve 700 is in the inverted configuration, the valve 700 is able to be placed within a smaller delivery sheath 726 than would otherwise be possible. For example, for comparison purposes, FIG. 30C illustrates the valve 700 placed within a lumen of a delivery sheath 726' where the valve 700 has not been moved to an inverted configuration prior to being disposed within the delivery sheath 726'. As shown in FIG. 30C, an outer diameter of the valve 700 is reduced, but not to as small of a diameter as for the valve 700 when placed in a delivery sheath 726 when in the inverted configuration. Thus, in FIG. 30C, the valve 700 has an overall outer perimeter or outer diameter D1 and in FIG. 30D, the valve 700 has an overall outer perimeter or outer diameter D2, which is less than D1.

Thus, by disposing the outer frame 720 in the inverted configuration, the valve 700 can be collapsed into a smaller overall diameter, i.e. placed in a smaller diameter delivery sheath 726, than would be possible if the valve 700 were merely collapsed radially. This is because when the valve is in the biased expanded configuration, the inner frame 750 is nested within an interior of the outer frame 720, and thus the outer frame 720 must be collapsed around the inner frame 750. In some embodiments, the inner frame 750 and the outer frame are disposed concentrically. Whereas in the inverted configuration, the inner frame 750 and the outer frame 720 are arranged axially with respect to each other (i.e., the inner frame is not nested within the outer frame 750), such that the outer frame 720 can be collapsed without needing to accommodate all of the structure of the inner frame 750 inside it. In other words, with the inner frame 750 disposed mostly inside or nested within the outer frame 720, the layers or bulk of the frame structures cannot be compressed to as small a diameter. In addition, if the frames are nested, the structure is less flexible, and therefore, more force is needed to bend the valve, e.g. to pass through tortuous anatomy or to make turns through a patient to be properly oriented for insertion into the mitral valve annulus.

Figure 32A:
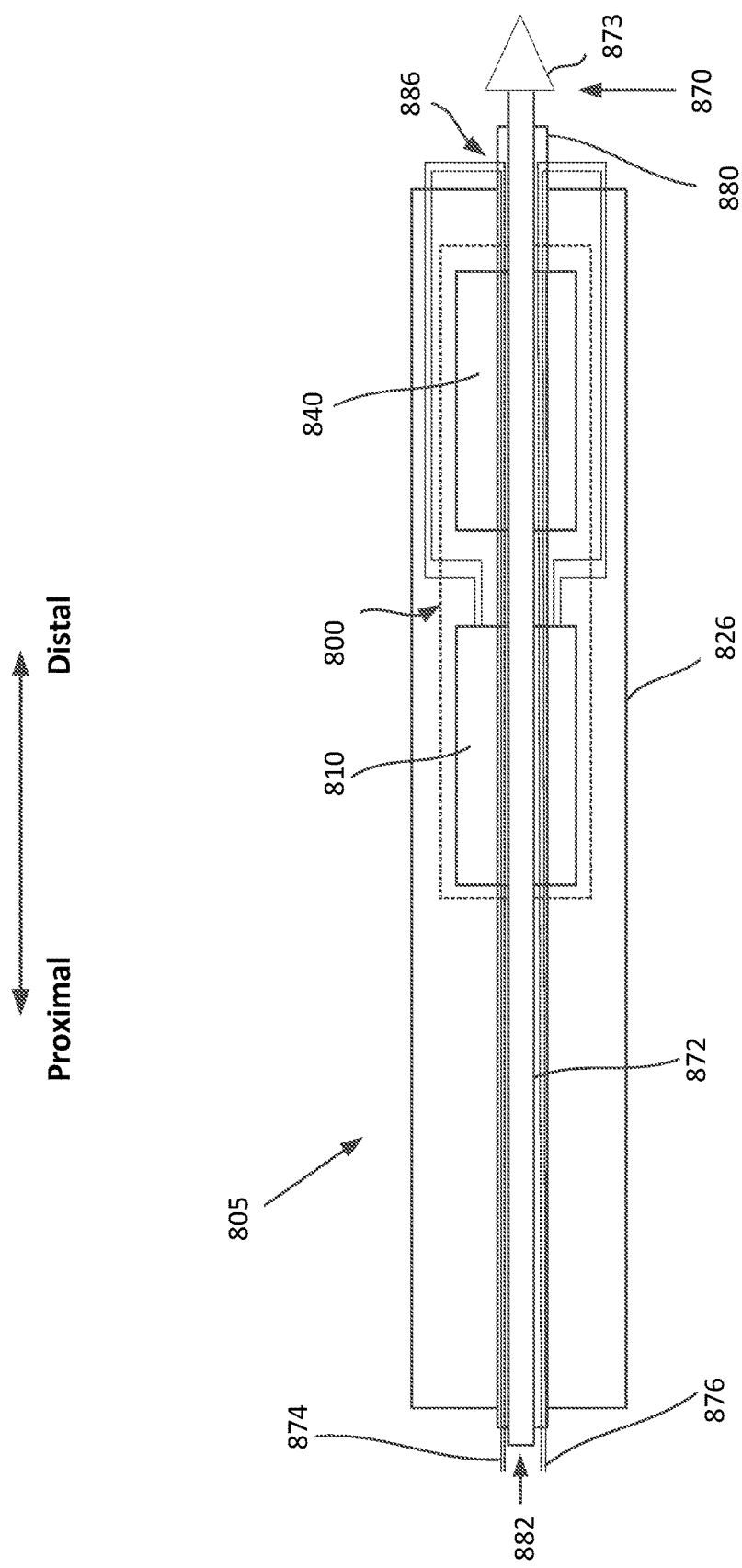
FIG. 32A is schematic illustration in side view of a delivery device and prosthetic heart valve, according to an embodiment.
Figure 32B:
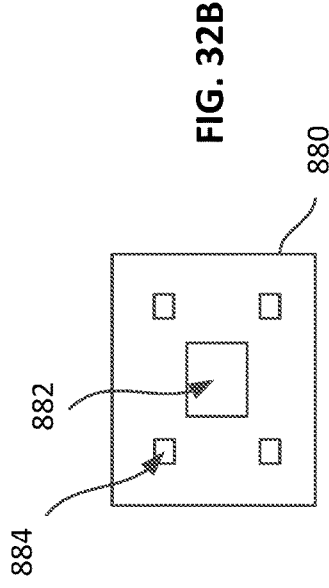
FIG. 32B is a schematic illustration of an end view of an elongate member of the delivery device of FIG. 32A.

FIG. 32A is a schematic illustration in side view of a delivery system that can be used to deliver and deploy a prosthetic heart valve within a heart of patient with, for example, a transapical approach. In this embodiment, a delivery system 805 includes a delivery sheath 826, a dilator 870, an elongate member 880, and two actuation wires 874 and 876. FIG. 32B is a schematic illustration in front view of the elongate member 880. In this schematic illustration, only two actuation wires are illustrated, but in other embodiments, only one actuation wire or more than two actuation wires can be used.

The delivery sheath 826 can be used to deliver a valve 800 that includes an inner valve assembly 840 including an inner frame (not labeled in FIG. 32A and FIG. 32B) and an outer frame assembly 810 including an outer frame (not labeled in FIG. 32A and FIG. 32B). The valve 800 can be constructed the same as or similar to, and function the same as or similar to, for example, the prosthetic valves described herein and/or in the '305 PCT Application, and can be moved between a deployed or expanded configuration and a delivery configuration in which the outer frame is disposed in an inverted positon relative to the inner frame as described above. As shown in FIG. 32A, the valve 800 can be disposed within a lumen of the delivery sheath 826 when the valve is in the delivery configuration (i.e., the outer frame is inverted relative to the inner frame and positioned proximal of the inner frame when in the delivery sheath). The actuation wires 874, 876 are releasably coupled to the outer frame assembly 810. In this manner, after delivery to and seating within the native annulus of the patient's heart, the actuation wires 874, 876 can be released from the outer frame assembly 810 and removed from the patient, leaving the prosthetic heart valve implanted within the patient's heart, as described in more detail herein.

The dilator 870 has a fluid delivery portion 872 and a collapsible dilation portion 873 (also referred to herein as "dilation portion"). The fluid delivery portion 872 is configured to receive a fluid and deliver the fluid to the dilation portion 873 to inflate the dilation portion 873. The dilation portion 873 is configured to be inflated such that when inflated it can dilate (e.g., expand an opening or passage) to one or more portions of the heart as the delivery system 805 is introduced into the heart of the patient. For example, in use during a transapical delivery approach, the dilation portion 873, when inflated, can extend outside a distal end of the delivery sheath 826 and provide a lead-in for the delivery sheath 826 and help open or enlarge the entry opening at the epicardial surface and ease entry through the mitral annulus without entangling the valve's chordae tendinae. With the delivery sheath 826 placed at a desired position within the heart, the dilator portion 873 can be deflated and removed leaving the delivery sheath 826 within the heart.

The dilation portion 873 can have any suitable shape or size to dilate a portion of the heart (e.g., an incision in an apical portion of the heart) and thereby assist delivery of the valve 800 to the atrium of the heart. For example, in some embodiments, a dilation portion can have a conical and/or tapered shape with a rounded or blunt distal tip. In other embodiments, a dilation portion can have a round shape, an oval shape, triangular, or other suitable shape. Although not shown, in some embodiments, a dilator can define a guide wire lumen therethrough. During delivery of a prosthetic valve, for example, a guidewire can be extended through an apical portion of the heart, through the left ventricle and into the left atrium of the heart. In such an embodiment, the dilator can be threaded over the guidewire to be inserted into the heart. The guidewire can be any suitable size. For example, in some embodiments, the guidewire can be from about a 0.03" guidewire to a 0.04" guidewire (e.g., a 0.035" guidewire). An example dilator device is described in U.S. patent application No. 14/527,382, filed Oct. 29, 2014 ("the '382 application"), the entire disclosure of which is incorporated herein by reference. As described in more detail herein, with the delivery sheath 826 placed at the desired position within the heart, the dilator portion 873 can be deflated (by removing the fluid therefrom) and removed along the guidewire leaving the delivery sheath 826 within the heart.

The elongate member 880 can be used to flip the outer frame assembly 810 and deliver to and retract from the heart at least a portion of the dilator 870. The elongate member 880 defines a dilator lumen 882 configured to slidably receive the dilator 870. More specifically, the dilator lumen 882 is configured to slidably receive the delivery portion 872, and the dilation portion 873 when deflated, as described in more detail herein. The elongate member 880 further defines four actuator wire lumens 884 (as shown in FIG. 32B) spaced radially apart from the dilator lumen 882 and configured to slidably receive the actuator wires 874, 876. The elongate member 880 is slidably disposed within the delivery catheter 826 and through a center portion of both the inner valve assembly 840 and the outer frame assembly 810. Although not shown, in some embodiments, the elongate member 880 can vary in size, e.g., its outer diameter or perimeter can increase and/or decrease at various portions of the elongate member 880. For example, in some embodiments, a portion of the elongate member 880 proximal to the valve 800, when the elongate member 880 is disposed within the delivery sheath 826 and extends through the center portions of the valve 800, can have a first diameter; and a portion of the elongate member 880 extending through the center portions (e.g., between the leaflets of the inner valve assembly 840) of the valve 800 can have a second diameter smaller than the first diameter. In this manner, the reduced diameter of the portion of the elongate member 880 configured to be disposed through a portion of the valve 800 can prevent or reduce potential undesirable interference with the valve 800 by the elongate member 880. Similarly, portions of the dilator 870, e.g., the fluid delivery portion 872, can vary in size (e.g., diameter) corresponding to the size variations of the elongate member 880.

The actuation wires 874, 876 can be coupled to the outer frame of the outer frame assembly 810 with a variety of different coupling methods. For example, the outer frame of the outer frame assembly 810 can include loops (not shown in FIGS. 32A and 32B) through which the actuation wires 874, 876 can be received or threaded. Such an outer frame is described in the '305 PCT Application incorporated herein (see, e.g., FIG. 57) and with respect to FIG. 27 herein. The number of loops on the outer frame can vary and the number of loops through which each actuation wire is connected can vary. For example, in some embodiments, the outer frame includes 12 loops and a first actuation wire (e.g., actuation wire 874) is threaded through 6 of the loops and a second actuation wire (e.g., actuation wire 876) is threaded through 6 of the loops. In other embodiments, the outer frame can include 12 loops and there can be 4 actuation wires, each coupled to 3 of the loops. In some embodiments, a single actuation wire is coupled through all of the loops of the outer frame.

To deliver and deploy the prosthetic valve 800 within a heart, the delivery sheath 826 can be inserted through the epicardial surface of the patient's heart (e.g., at or near an apex region of the heart) and extended through the left ventricle and to the left atrium of the heart. Prior to inserting the delivery sheath 826 into the heart, with the dilation portion 873 of the dilator 870 extending outside a distal end of the delivery sheath 826, a fluid can be injected to the fluid delivery portion 872 thereby inflating the dilation portion 873 of the dilator 870. The distal end portion (e.g., tapered distal end) of the dilation portion 873 can provide a lead-in for the delivery sheath 826 and help open or enlarge the entry opening at the epicardial surface and through the mitral annulus. When the delivery sheath 826 is placed at the desired position within the heart, the fluid can be at least partially withdrawn or removed from the dilation portion 873 thereby deflating the dilation portion 873, and the deflated dilation portion 873 can be removed through the delivery catheter 826, leaving the delivery sheath 826, the inner valve assembly 840 and the outer frame assembly 810 within the heart.

With the distal end of the delivery sheath 826 disposed within the left atrium, the valve 800 can be moved out of the lumen of the delivery sheath 826 by withdrawing the delivery sheath 826 proximally and/or using a pusher device to push the valve 800 out the distal end of the delivery sheath 826 and/or using the elongate member 880 and actuation wires 874, 876 to assist in pulling the valve 800 out of the distal end of the delivery sheath 826. More specifically, with the actuation wires 874, 876 coupled to the outer frame assembly 810, the ends of the actuation wires 874, 876 can extend distally from the outer frame assembly 810 out the distal end of the delivery sheath 826 and then pass into the actuation wire lumens 884 of the elongate member 880 via side apertures or holes 886 (labeled in FIG. 32A) defined by the elongate member 880. In some embodiments, rather than side openings, the actuation wires lumens extend out openings in a distal end of the elongate member 880. In other words, the lumens 884 can extend to the distal end of the elongate member 880. The ends of the actuation wires 874, 876 can then extend proximally through the actuation wire lumens 884 of the elongate member 880 and out the proximal end of the elongate member 880 and the proximal end of the delivery sheath 826. More specifically, each wire 874, 876 has two ends. A first end is held at the proximal end of the elongate member 880, and the second end extends distally through a first actuation wire lumen 884, through the loops (not shown) of the outer frame assembly 810, back through a second actuation wire lumen 884 and extends proximally out the proximal end of the elongate member 880. Thus, for an embodiment with two actuation wires and four actuation wire lumens, four ends of the actuation wires will extend proximal of a distal end of the delivery system 305 or coupled to a portion of the delivery system (e.g., a catheter or handle). Thus, a user (e.g., physician) can pull the end portions of the actuation wires 874, 876 to in turn pull the outer frame assembly 810 out of the distal end of the delivery sheath 826 as described in more detail below.

In some embodiments, the end portions of the actuation wires 874, 876 extend proximally from the proximal end of the elongate member 880 and are operably coupled to a handle (not shown). The handle can be manipulated by a user to selectively pull and/or release the actuation wires 874, 876. In some embodiments, the handle can include one or more toggle switches or similar mechanisms to help control the transition of the valve 800. In this manner, a user can use the handle to selectively pull the valve 800 distally and out from the delivery sheath 826, and selectively control the flipping or transition between configurations of the outer frame assembly 810. In some embodiments, the end portions of actuation wires extend proximally through actuation wire lumens of a delivery sheath and out the proximal end of an elongate member, but remain within the delivery sheath. In such embodiments, a handle or functionally similar actuation wire manipulator is operably coupled to the actuation wires, and can be actuated and/or manipulated to selectively pull or release the actuation wires for delivery and/or deployment of the valve 800, as described above.

During delivery of the valve 800, as the inner valve assembly 840 exits the distal end of the delivery sheath 826, the outer frame assembly 810 will be in an inverted configuration relative to the inner valve assembly 840 (similar to as shown and described with respect to FIG. 30B). After the inner valve assembly 840 is outside of the lumen of the delivery sheath 826, the outer frame assembly 810 can begin to exit the lumen of the delivery sheath 826 and to revert to its expanded or deployed configuration (similar to as shown, for example, with respect to FIG. 30A). In this embodiment, the actuation wires 874, 876 can function to selectively (e.g., by an operator) assist and/or control the expansion and reversion profile of the valve 800 as the valve 800 is delivered to the heart. For example, a distal end of the elongate member 880 can be moved distally out of the delivery sheath 826, and the end portions (extending proximally out of the delivery sheath 826) of the actuation wires 874, 876 can be pulled proximally (or a handle coupled thereto can be manipulated), which in turn pulls the open end of the outer frame distally relative to the inner frame to help move the outer frame to its reverted expanded configuration. Thus the actuation wires and elongate member 880 can be used to help manipulate the outer frame assembly 810 to assist and control the transition of the outer frame assembly 810 from its inverted configuration relative to the inner valve assembly 840 to its expanded or deployed configuration. In this manner, the profile of the valve 800 as the outer frame assembly 810 transitions from its inverted configuration to its reverted, expanded or deployed configuration can be selectively minimized and/or otherwise manipulated as desired by a user. Such control of the profile of the valve 800 throughout its transition between configurations and during delivery and deployment of the valve 800 can promote a safer, more repeatable and efficient valve delivery and deployment procedure. In some embodiments, the actuation wires 874, 876 can be manually grasped by a user to pull the actuation wires proximally. In some embodiments, the actuation wires 874, 876 can be operatively coupled to the delivery system 805 such that the user does not have to manually handle the actuation wires. For example, the actuation wires can be coupled to a delivery sheath and/or to a handle assembly (not shown) of the delivery system 805.

With the outer frame assembly 810 reverted relative to the inner valve assembly 840 such that the valve 800 is disposed in its deployed configuration within the annulus of the heart, the delivery system 805 can be removed from the heart. For example, the actuation wires 874, 876 can be decoupled from the outer frame assembly 810 and removed from the heart via the elongate member 880, and the elongate member 880 and the delivery sheath 826 can be withdrawn from the heart, leaving the valve 800 implanted within the annulus of the heart. More specifically, to decouple the actuation wires 874, 876 from the outer frame assembly 810 and remove the actuation wires 874, 876 from the patient, a single proximal end of the actuation wires 874, 876 can be pulled proximally such that the other proximal end of the actuation wires 874, 876 gets pulled distally through the actuator wire lumens 884, out the apertures or holes 886 in the elongate member 880, through the loops of the outer frame 820, and back out through the actuator wire lumens 884. In this manner, the actuation wires 874, 876 can be removed from the elongate member 880, the delivery sheath 826, and the patient after the actuation wires 874, 876 are used to facilitate delivery and deployment of the valve 800 within the heart.

Figure 33B:
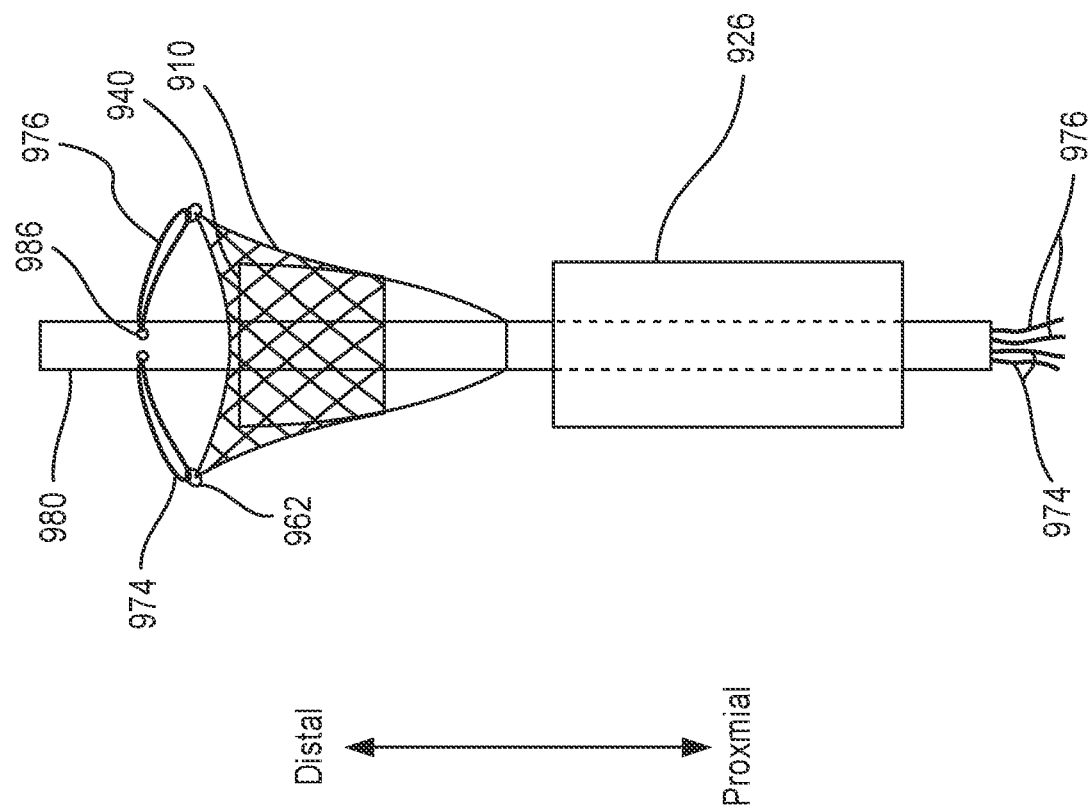
FIG. 33B is an illustration in side view of the prosthetic heart valve of FIG. 33A in a reverted configuration and outside the delivery sheath.
Figure 33A:
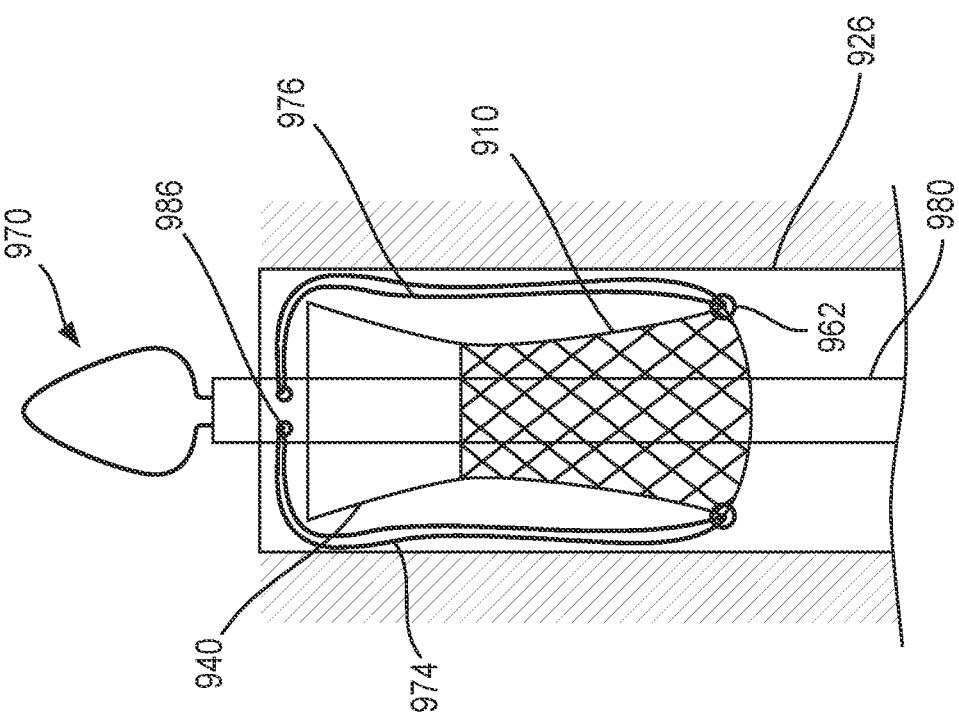
FIG. 33A is a cross-sectional side-view of a delivery sheath, with a prosthetic valve in an inverted configuration and disposed therein, according to an embodiment.

FIG. 33A is an illustration in side view of a delivery system 905 that can be used to delivery and deploy a prosthetic heart valve 900 within a heart of a patient with, for example, a transapical approach. The delivery system 905 can be constructed the same as or similar to, and function the same as or similar to, for example, the delivery system 805. Further, the valve 900 can be constructed the same as or similar to, and function the same as or similar to, for example, any of the prosthetic valves described herein or any of the prosthetic valves described in the '305 PCT Application, and can be moved between a deployed or expanded configuration and a delivery configuration in which the outer frame is disposed in an inverted position relative to the inner frame as described herein with respect to the valve 800. As shown in FIG. 33A, the valve 900 is disposed in its inverted configuration and radially constrained within the delivery sheath prior to being deployed and implanted within a heart as described in more detail below. Further, as shown in FIG. 33B, the valve 900 is disposed in its reverted, deployed configuration after being delivered to the heart and before the actuation wires and delivery sheath have been removed. It should be understood that for features and functions not specifically discussed with respect to the delivery system 905, those features and functions can be the same as or similar to the delivery system 805 or any of the delivery systems described herein. Similarly, it should be understood that for features and functions not specifically discussed with respect to the prosthetic valve 900, those features and functions can be the same as or similar to the valve 800 or any of the valves described in the '305 PCT Application.

Figure 33C:
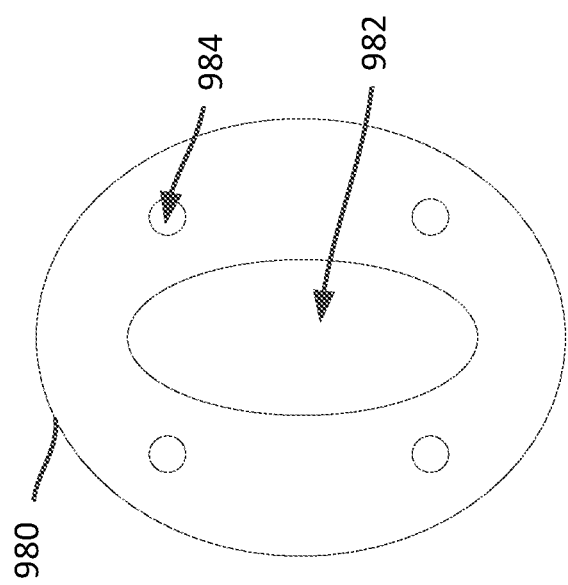
FIG. 33C is an illustration of an end view of the elongate member of the delivery device of FIG. 33A.

The delivery system 905 includes a delivery sheath 926, a dilator 970, an elongate member 980, and two actuation wires 974 and 976. FIG. 33C is a distal end view of the elongate member 980. The delivery sheath 926 can be used to deliver a valve 900 that includes an inner valve assembly 940 including an inner frame (not labeled in FIG. 33A) and an outer frame assembly 910 including an outer frame (not labeled in FIG. 33A).

Figure 33D:
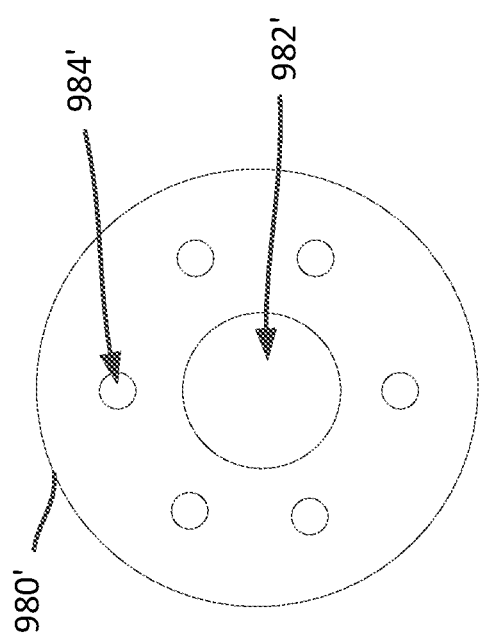
FIG. 33D is an illustration of an end view of an elongate member of a delivery device, according to an embodiment.

The elongate member 980 can be used to assist in the flipping of the outer frame assembly 910 and deliver to and retract from the heart at least a portion of the dilator. As shown in FIG. 33C, the elongate member 980 defines a dilator lumen 982 configured to slidably receive the dilator 970. More specifically, the dilator lumen 982 is configured to slidably receive the dilator 970 therethrough when the dilator portion 973 is deflated. The elongate member 980 further defines four actuator wire lumens 984 (as shown in FIG. 33C) spaced radially apart from the dilator lumen 982 and configured to receive the actuation wires 974, 976. The elongate member 980 is slidably disposed within the delivery catheter 926 and through a center portion of both the inner valve assembly 940 and the outer frame assembly 910. In alternative embodiments, an elongate member can define any suitable number of actuator wire lumens. For example, as shown in FIG. 33D, an elongate member 980' can define six actuator wire lumens 984' spaced radially apart from the dilator lumen 982'. Similar to the actuator wire lumens 984 discussed above, the six actuator wire lumens 984' can be configured to receive actuator wires (e.g., actuator wires 974 and 976). In yet alternative embodiments, actuator wire lumens can be configured to receive any suitable number of actuator wires. For example, in some embodiments in which a delivery system includes an elongate member defining six actuator wire lumens (e.g., actuator wire lumens 984'), the delivery system can include three actuator wires. In such embodiments, in some instances, each actuator wire can be routed through two actuator wire lumens. Said another way, a first actuator wire can be routed through a first set of two actuator wire lumens; a second actuator wire can be routed through a second set of two actuator wire lumens; and a third actuator wire can be routed through a third set of two actuator wire lumens. Further, an elongate member can have any suitable shape (e.g., circular, oval, triangular, or the like). For example, as shown in FIG. 33D, the elongate member 980' is circular.

In this embodiment, as shown, the actuation wires 974, 976 can be releasably coupled to the outer frame of the outer frame assembly 910. For example, as shown in FIGS. 33A and 33B, the actuation wires 974, 976 can be passed through loops 962 disposed around an open end portion of the outer frame assembly 910. More specifically, as described above, a first end of each actuation wire 974, 976 is held at the proximal end of the elongate member 980, and the second end extends distally through a first actuation wire lumen 984, through the loops 962 of the outer frame assembly 910, back through a second actuation wire lumen 984 and extends proximally out the proximal end of the elongate member 980 (see e.g., FIG. 33B).

To deliver and deploy the prosthetic valve 900 within a heart, the delivery sheath 926 can be inserted through the epicardial surface of the patient's heart (e.g., at or near an apex region of the heart) and extended through the left ventricle and to the left atrium of the heart. Prior to inserting the delivery sheath 926 into the heart, with the dilation portion of the dilator extending outside a distal end of the delivery sheath 926, a fluid can be injected to the fluid delivery portion 972 thereby inflating the dilation portion 973 of the dilator 970. The distal end portion (e.g., tapered distal end) of the dilation portion 973 can provide a lead-in for the delivery sheath 926 and help open or enlarge the entry opening at the epicardial surface and through the mitral annulus. When the delivery sheath 926 is placed at the desired position within the heart, the fluid can be at least partially withdrawn or removed from the dilation portion 973 thereby deflating the dilation portion 973, and the deflated dilation portion 973 can be removed through the delivery catheter 926, leaving the delivery sheath 926, the inner valve assembly 940 and the outer frame assembly 910 within the heart.

With the distal end of the delivery sheath 926 disposed within the left atrium, the valve 900 can be moved out of the lumen of the delivery sheath 926 by, for example, withdrawing the delivery sheath 926 proximally and/or moving the elongate member 980 distally and using the actuation wires 974, 976 to assist in pulling the valve 900 out of the distal end of the delivery sheath 926. As described above for the previous embodiment, the inner valve assembly 940 will exit the delivery sheath 926 first and then the outer frame assembly 910. Unconstrained by the delivery sheath 926, the inner valve assembly 940 and outer frame assembly 910 can assume their biased expanded configurations.

To flip or revert the outer frame assembly 910, the elongate member 980 can be moved distally out of the delivery sheath 926 as shown in FIG. 33B. With the elongate member 980 moved distally, the proximal ends of the actuation wires 974, 976 can be pulled proximally, which will in turn pull the open end of the outer frame assembly 910 (to which the actuation wires 974, 976 are coupled) distally to help revert the outer frame. For example, as described above, a user (e.g., physician) can pull the end portions of the actuation wires 974, 976 to in turn move the outer frame assembly 910 to its reverted configuration. In some embodiments, the end portions of the actuation wires 974, 976 extend proximally from the proximal end of the elongate member 980 and are operably coupled to a handle (not shown). The handle can be manipulated by a user to selectively pull and/or release the actuation wires 974, 976. In some embodiments, the handle can include one or more toggle switches or similar mechanisms to help control the transition of the valve 900. In this manner, a user can use the handle to selectively pull the valve 900 distally and out from the delivery sheath 926, and selectively control the flipping or transition between configurations of the outer frame assembly 910. In some embodiments, the end portions of actuation wires extend proximally through actuation wire lumens of a delivery sheath and out the proximal end of an elongate member, but remain within the delivery sheath. In such embodiments, a handle or functionally similar actuation wire manipulator is operably coupled to the actuation wires, and can be actuated and/or manipulated to selectively pull or release the actuation wires for delivery and/or deployment of the valve 900, as described above.

As described above, as the valve 900 exits the distal end of the delivery sheath 926, the outer frame assembly 910 will be in an inverted configuration relative to the inner valve assembly 940 (similar to as shown and described with respect to FIG. 30B). After the inner valve assembly 940 is outside of the lumen of the delivery sheath 926, the outer frame assembly 910 can begin to exit the lumen of the delivery sheath 926 and to revert to its expanded or deployed configuration (as shown in FIG. 33B). In this embodiment, the actuation wires 974, 976 can function to selectively (e.g., by an operator) assist and/or control the expansion and reversion profile of the valve 900 as the valve 900 is delivered to the heart. For example, a distal end of the elongate member 980 can be moved distally out of the delivery sheath 926, and the end portions (extending proximally out of the delivery sheath 926) of the actuation wires 974, 976 can be pulled proximally (or a handle coupled thereto can be manipulated), which in turn pulls the open end of the outer frame distally relative to the inner frame to help move the outer frame to its reverted expanded configuration. Thus the actuation wires 974, 976 and the elongate member 980 can be used to help manipulate the outer frame assembly 910 to assist and control the transition of the outer frame assembly 910 from its inverted configuration relative to the inner valve assembly 940 to its expanded or deployed configuration. In this manner, the profile of the valve 900 as the outer frame assembly 910 transitions from its inverted configuration to its reverted, expanded or deployed configuration can be selectively minimized and/or otherwise manipulated as desired by a user. Such control of the profile of the valve 900 throughout its transition between configurations and during delivery and deployment of the valve 900 can promote a safer, more repeatable and efficient valve delivery and deployment procedure. In some embodiments, the actuation wires 974, 976 can be manually grasped by a user to pull the actuation wires proximally. In some embodiments, the actuation wires 974, 976 can be operatively coupled to the delivery system 905 such that the user does not have to manually handle the actuation wires. For example, the actuation wires can be coupled to a delivery sheath and/or to a handle assembly (not shown) of the delivery system 905.

With the outer frame assembly 910 reverted relative to the inner valve assembly 940 such that the valve 900 is disposed in its deployed configuration (as shown in FIG. 33B) within the annulus of the heart, the delivery system 905 can be removed from the heart. For example, the actuation wires 974, 976 can be decoupled from the outer frame assembly 910 and removed from the heart via the elongate member 980, and the elongate member 980 and the delivery sheath 926 can be withdrawn from the heart, leaving the valve 900 implanted within the annulus of the heart. More specifically, to decouple the actuation wires 974, 976 from the outer frame assembly 910 and remove the actuation wires 974, 976 from the patient, a single proximal end of the actuation wires 974, 976 can be pulled proximally such that the other proximal end of the actuation wires 974, 976 gets pulled distally through the actuator wire lumens 984, out the side apertures or holes 986 in the elongate member 980 (each side aperture or hole 986 being in communication with a corresponding actuator wire lumen 984), through the loops 962 of the outer frame 920, and back out through the actuator wire lumens 984. In this manner, the actuation wires 974, 976 can be removed from the elongate member 980, the delivery sheath 926, and the patient after the actuation wires 974, 976 are used to facilitate delivery and deployment of the valve 900 within the heart.

In some embodiments, after the valve 900 has been delivered and deployed within the heart, the delivery sheath 926 can be moved distally (before and/or after the actuation wires 974, 976 have been removed from the elongate member 980, the delivery sheath 926, and/or the patient) to capture or otherwise engage with at least a proximal portion of the valve 900 and at least partially collapse the proximal portion of the valve. The delivery sheath 926 can then be used to move and/or reorient (e.g., rotate, clock, angle) the valve 900 within the heart. For example, a user can rotate the delivery sheath 926 about its longitudinal axis to in turn rotate the valve 900 about its longitudinal axis. In this manner, a user can ensure proper implantation of the valve 900 within the heart without having to remove the valve 900 from the heart, for example, when the valve 900 is not first implanted in a proper manner.

Figure 34:
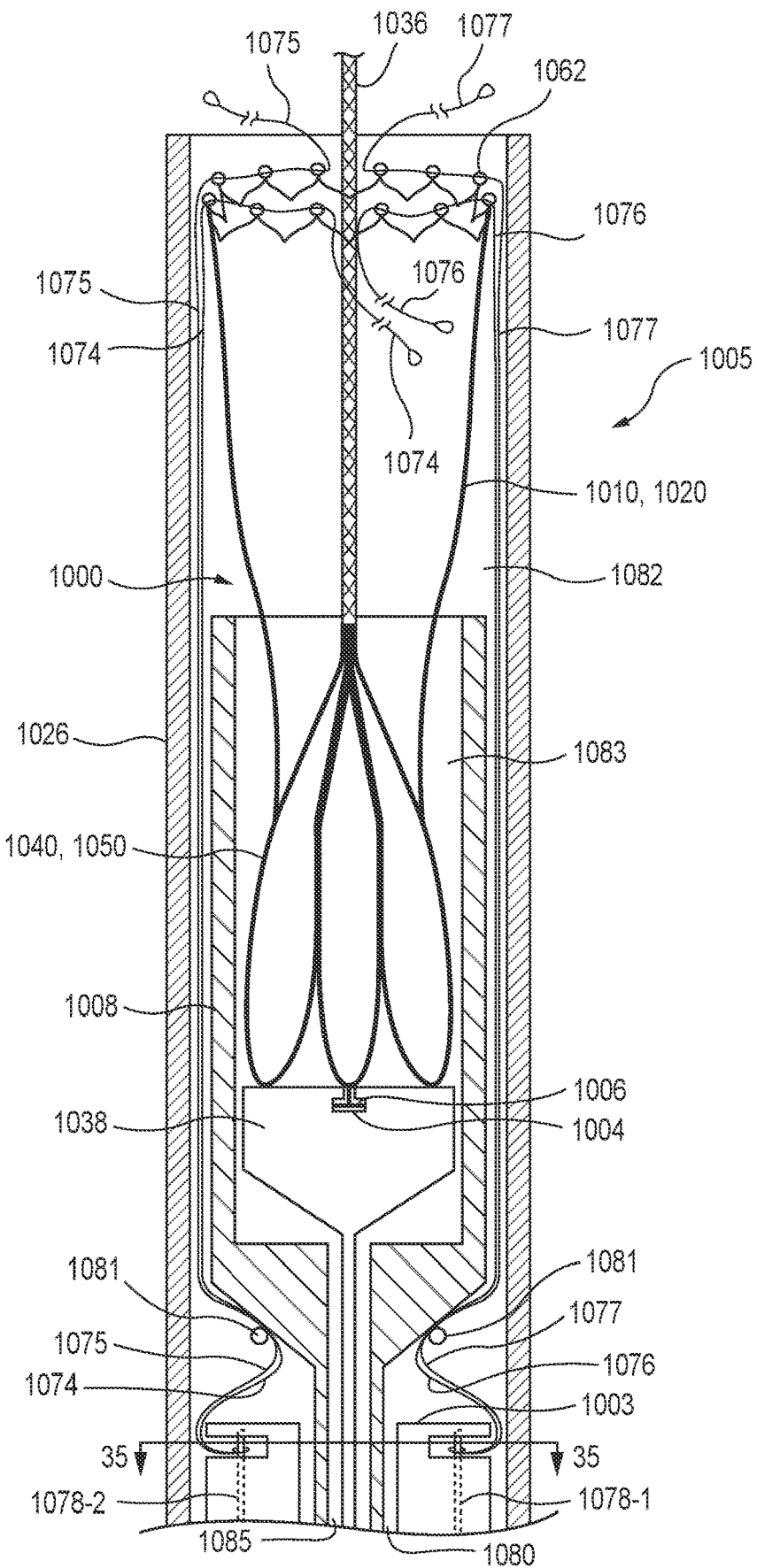
FIG. 34 is a partial cross-sectional side view of a delivery system and prosthetic heart valve, according to an embodiment.

FIGS. 34-42 illustrate a delivery system 1005 for delivering and deploying a prosthetic heart valve, such as, prosthetic heart valve 1000, within a heart, according to another embodiment. The prosthetic heart valve 1000 (also referred to herein as "valve") can be constructed the same as or similar to, and function the same as or similar to any of the valves described herein. Thus, some details regarding the valve 1000 are not described herein. As shown in FIG. 34, the valve 1000 has an outer frame assembly 1010 with an outer frame 1020 and an inner valve assembly 1040 with an inner frame 1050, and a tether 1036 coupled to the inner frame 1050. As described above for previous embodiments (e.g., valve 100, 200, 300 etc.), the outer frame 1020 and the inner frame 1050 of valve the 1000 can each be formed with a shape-memory material and have a biased, expanded or deployed configuration. The outer frame 1020 and the inner frame 1050 can be moved to a collapsed or undeployed configuration for delivery of the valve 1000 to the heart in which the outer frame 1020 is inverted relative to the inner frame 1050. To prepare the valve 1000 for delivery to the heart, the outer frame 1020 of the valve 1000 is first disposed in a prolapsed or inverted configuration as shown in FIG. 34. Specifically, the elastic or superelastic structure of outer frame 1020 of valve 1000 allows the outer frame 1020 to be disposed in the prolapsed or inverted configuration relative to the inner frame 1050 as described above, for example with respect to valve 100.

For example, to dispose the outer frame 1020 in its inverted configuration relative to the inner frame 1050, the outer frame 1020 is folded or inverted distally such that the outer frame 1020 is pointed away from the inner frame 1050. With the outer frame 1020 in the inverted configuration, the valve 1000 can be placed within a lumen of the delivery system 1005 as shown in FIG. 34 for delivery of the valve 1000 to the left atrium of the heart. As discussed above, by disposing the outer frame 1020 of the valve 1000 in the inverted configuration, the valve 1000 can be collapsed into a smaller overall diameter, i.e., placed in a smaller diameter delivery sheath, than would be possible if the valve 1000 were collapsed radially when the inner frame 1050 and the outer frame 1020 are disposed concentric to one another.

In this embodiment, the delivery system 1005 includes an outer delivery sheath 1026, an inner sheath 1008, a valve holder 1038 (also referred to as a "pusher") and a multi-lumen elongate tube member 1003 (also referred to as "tube" or "tube member" or "multi-lumen elongate member"). As shown in FIGS. 34 and 39-41, the tube member 1003 is movably disposed within a lumen 1082 defined by the outer delivery sheath 1026. The inner sheath 1008 is movably disposed within the lumen 1082 and within a lumen 1080 defined by the tube member 1003. The valve holder 1038 is movably disposed within a first lumen 1083 and a second lumen 1085 defined by the inner sheath 1008 that are in fluid communication with each other.

To deploy the valve 1000 within a heart, the outer frame 1020 of the valve 1000 is first moved or placed in its inverted configuration relative to the inner frame 1050. As shown in FIG. 34, a portion of the valve 1000 is placed within the lumen 1082 of the outer sheath and a portion of the valve 1000 is placed within the lumen 1083 of the inner sheath 1008. As described above for previous embodiments, when the valve 1000 is placed within the delivery system (e.g., outer sheath 1026 and inner sheath 1008) the valve 1000 can be compressed or collapsed to a smaller configuration (e.g., a smaller outer perimeter).

The inner frame 1050 can be releasably coupled to the valve holder 1038 via couplers 1006 that are received within corresponding recesses 1004 defined by the valve holder 1038 in the same manner as described above for delivery system 405 (see, e.g., FIGS. 26A-26C). In this manner, the valve holder 1038 can be used to hold the valve 1000 to aid in the control and manipulation of the valve 1000 as it is being deployed within a heart. In addition, the valve holder 1038 can limit radial expansion of the inner frame 1050 as the valve 1000 is moved within the lumen of the delivery sheath 1026 and during deployment outside of the delivery sheath 1026. As described above for valve 400, an inner diameter 1082 of the inner sheath 1008 can be sized such that when the valve holder 1038 and valve 1000 are disposed therein, the couplers 1006 are unable to exit the recesses 1004. In other words, the inner walls of the inner sheath 1008 maintain the couplers 1006 within the recesses 1004. When the valve 1000 is moved outside of the inner sheath 1008, the couplers 1006 will be able to freely exit the recesses 1004, releasing the inner frame 1050 from the valve holder 1038.

In alternative embodiments, the valve holder 1038 can be removably coupled to the valve 1000 (e.g., the inner frame 1050 of the valve 1000) via wires or sutures that can be cut after delivery of the valve 1000 to the heart. In some cases, the valve holder 1038 can be decoupled from the valve 1000 when the valve is still disposed within the outer delivery sheath 1026, while in other instances the valve holder 1038 can be decoupled from the valve 1000 after the valve 1000 exits the delivery sheath 1026 within the heart.

Although not shown, in other embodiments, the valve holder 1038 can merely contact and push the valve 1000 during deployment, as described for previous embodiments, without securing the inner frame 1050 to the valve holder 1038. In such embodiments, in some instances, radial expansion of the inner frame 1050 can be restricted by the inner sheath 1008 when the inner frame 1050 is disposed therein.

In this embodiment a first actuation wire 1076, a second actuation wire 1074, a third actuation wire 1076 and a fourth actuation wire 1077 are each coupled to the outer frame assembly 1010. More specifically, the outer frame 1020 of the outer frame assembly 1010 includes loops 1062 through which the actuation wires 1074-1077 can be threaded or received therethrough. In this embodiment, the outer frame 1020 includes 12 loops 1062 and each actuation wire 1074-1077 is threaded through 3 of the loops 1062. In other embodiments, there can be a different number of loops disposed on the outer frame 1020 and there can be a different number of actuators. Further, each actuation wire can be threaded or received through a different number of loops than shown for this embodiment.

When the valve 1000 is disposed within the delivery system 1005 as shown, for example, in FIG. 34, the actuation wires 1074-1077 each extend from the outer frame 1020 proximally within the lumen 1082 of the outer sheath and along an outside wall of the inner sheath 1008, are tucked or placed behind one or more seals 1081 or other holding device, and pinned by an elongate pinning member 1078-1, 1078-2, 1078-3, 1078-4 (collectively referred to as pinning members 1078) to the tube member 1003. The seal 1081 can be configured such that the actuation wires 1074-1077 can slide relative to the seal 1081 during actuation and deployment of the valve 1000 as described in more detail below.

As shown in FIGS. 34 and 39-41, a first end of the actuation wire 1074 and a first end of the actuation wire 1075 are pinned by a pinning member 1078-2, and a first end of the actuation wire 1076 and a first end of the actuation wire 1077 are pinned by a pinning member 1078-1. A second end of the actuation wire 1074 and a second end of the actuation wire 1076 are pinned by a pinning member 1078-4 (not shown in the partial cross-sectional views of FIGS. 34 and 39-41), and a second end of the actuation wire 1075 and a second end of the actuation wire 1077 are pinned by a pinning member 1078-3 (not shown in the partial cross-sectional views of FIGS. 34 and 39-41). The second ends of the actuation wires are shown detached in FIGS. 34 and 39-41 for ease of illustration.

Figure 35:
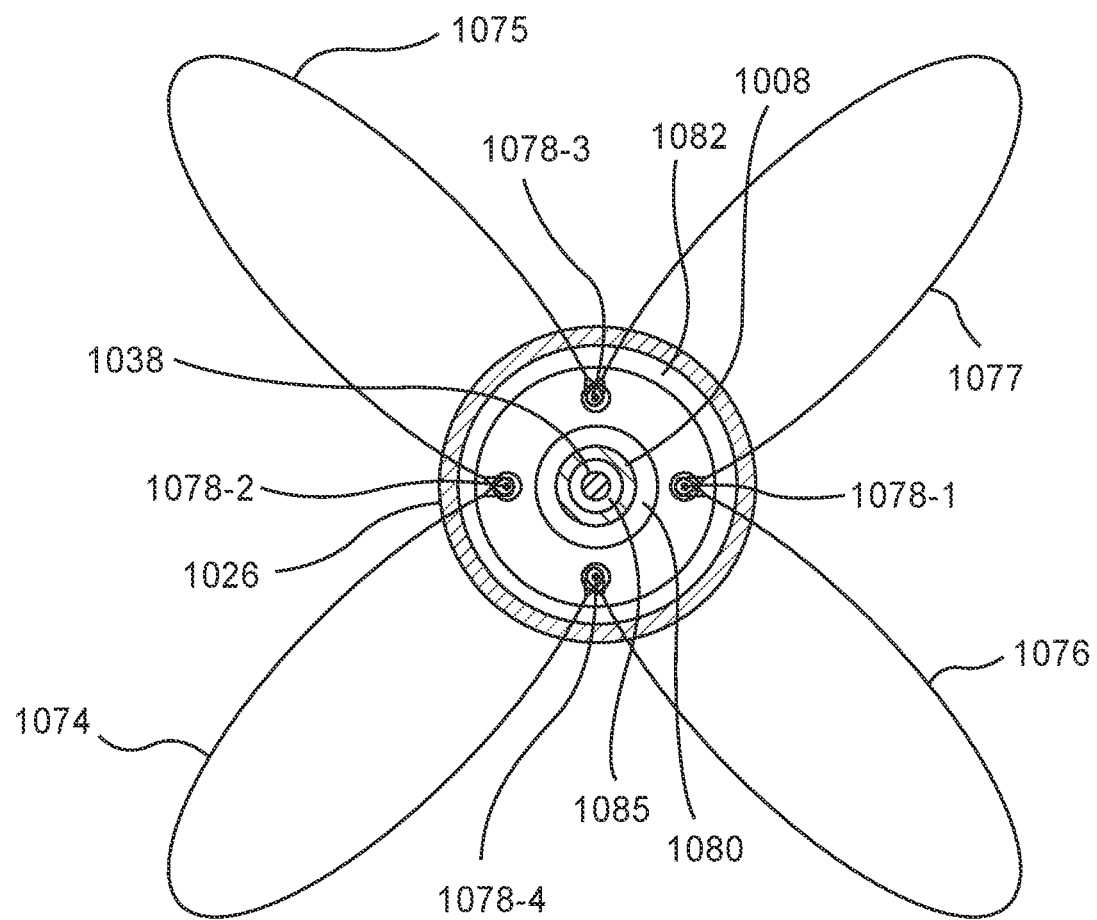
FIG. 35 is a cross-sectional view taken along line 35-35 in FIG. 34 showing the actuation wires coupled to a tube member of the delivery system.
Figure 38A:
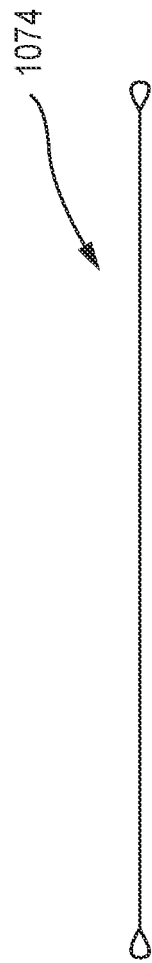
FIGS. 38A-38D are each a side view of a different embodiment of an actuation wire.
Figure 38B:
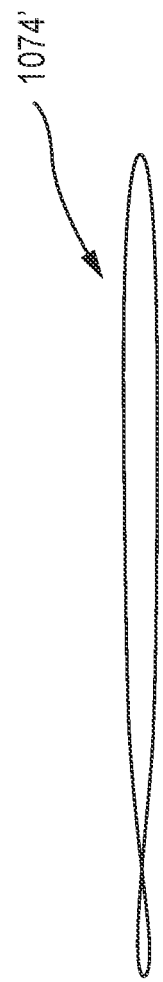
Figure 38C:
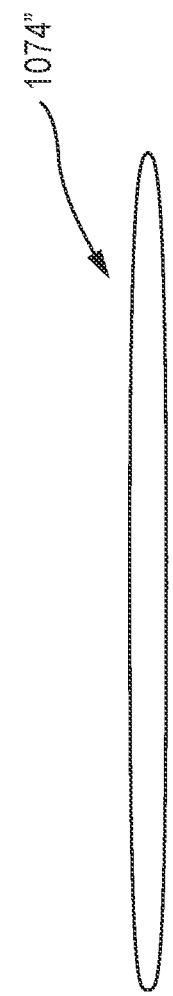
Figure 38D:
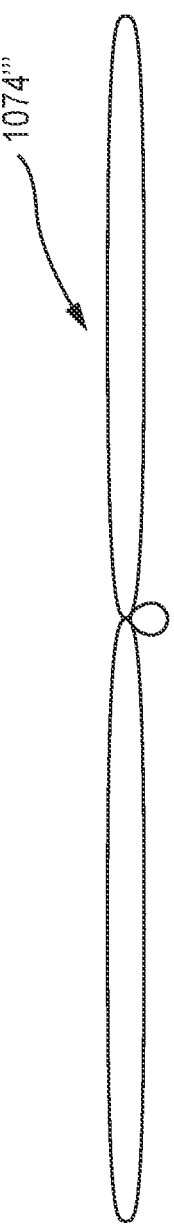

FIG. 35 is a cross-sectional view taken along line 35-35 in FIG. 34 and illustrates the pinning of the actuation wires 1074-1077. The actuation wires 1074-1077 are shown unattached to the outer frame for illustration purposes. FIG. 38A illustrates the actuation wire 1074 and is representative of the other actuation wires 1075-1077. FIGS. 38B, 67B and 67C illustrate alternative embodiments for the actuation wires labeled 1074', 1074" and 1074"'. As shown in FIG. 38A, the actuation wires 1074-1077 each include a loop on both ends of the actuation wire, which is pinned by the pinning members 1078. In FIG. 38B, the pinning members can pin the smaller loop on one end of the actuation wire 1074' and the end of the larger loop on the opposite end of the actuation wire 1074'. In FIG. 38C, the actuation wire 2475" is in the form of a closed loop and each end of the loop can be pinned by a pinning member. In FIG. 38D, the actuation wire 1074''' includes two elongate loops and a center smaller loop. In this embodiment, the actuation wire 1074''' can be pinned by three pinning members, a first pinning member can pin an end of one of the larger loops, a second pinning member can pin an end of the other larger loop, and the small loop can be pinned by a third pinning member. In each of the embodiments of FIGS. 38B-38D, a double layer of the actuation wire would be passed or threaded through the loops of the outer frame of the valve. Other alternative configurations can also be used.

As shown in FIGS. 36 and 37A, the multi-lumen tube member 1003 defines four pinning member lumens 1079-1, 1079-2, 1079-3, 1079-4 (collectively referred to as pinning member lumens 1079). The end portions of the actuation wires 1074-1077 are placed within the circumferential recess or groove 1084 defined by the tube member 1003, where the pinning members 1078 are received through the loops on the ends of the actuation wires 1074-1077, pinning the actuation wires 1074-1077 to the tube member 1003. Thus, during deployment of the valve 1000 within a heart, a user (e.g., physician) can use the tube member 1003, to which the actuation wires 1074-1077 are coupled, to control and/or manipulate movement of the valve 1000 as described in more detail below.

Figure 37B:
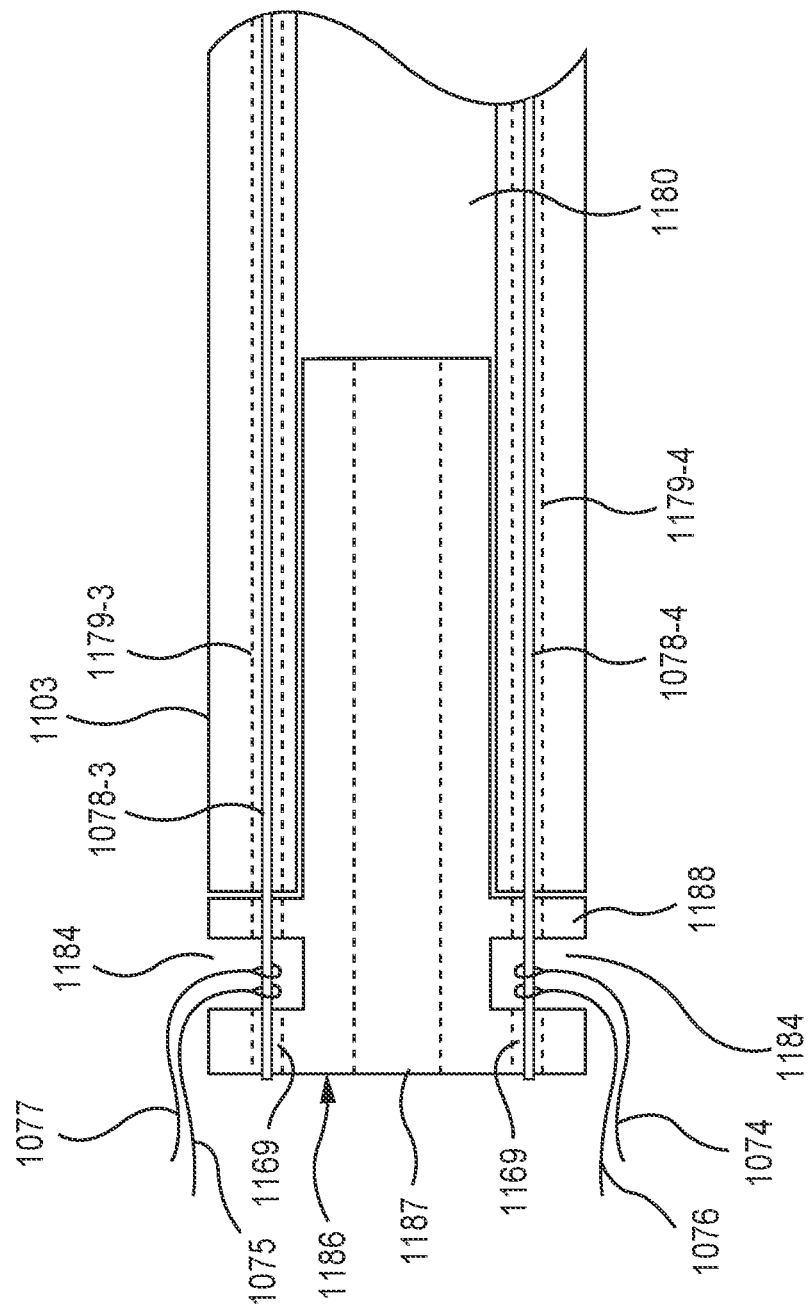
FIG. 37B is a side view of a portion of a multi-lumen tube member according to another embodiment and a distal retention element according to an embodiment.
Figure 37C:
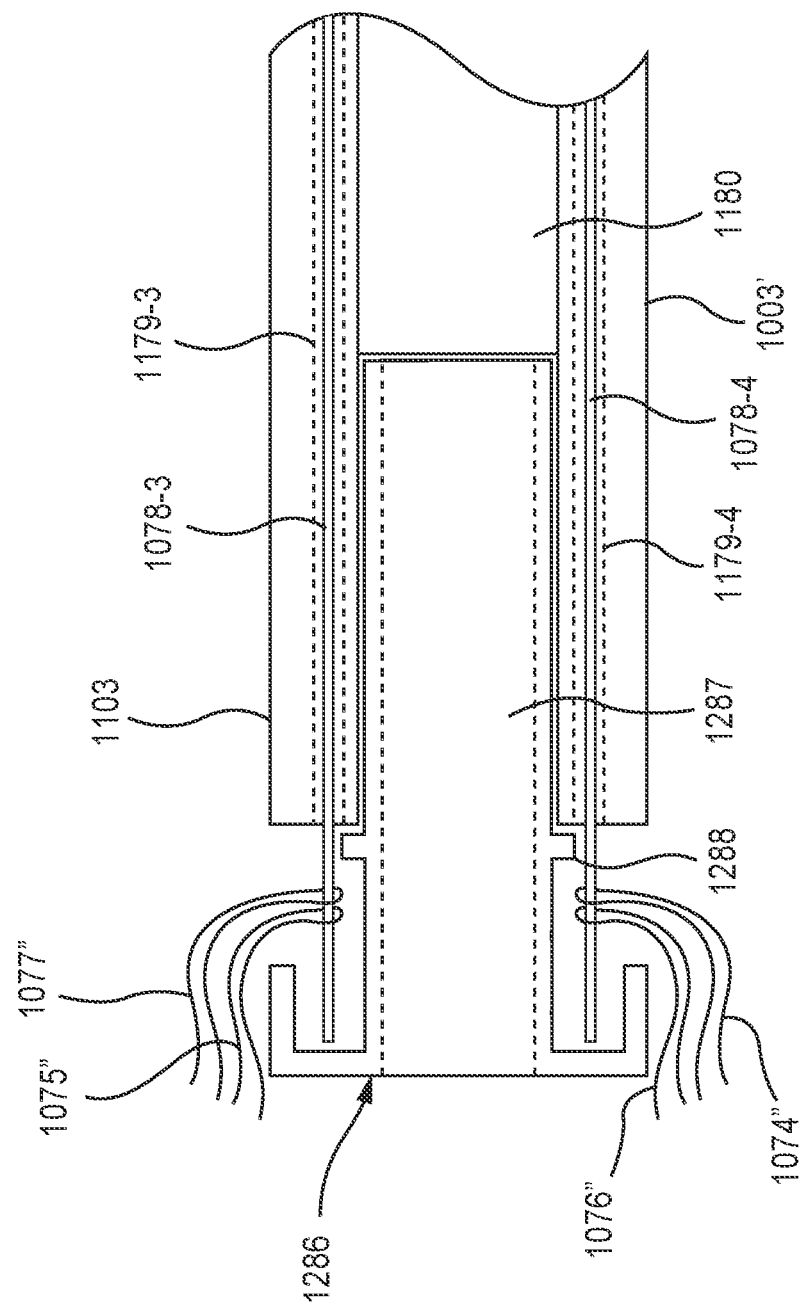
FIG. 37C view of a portion of the multi-lumen tube member of FIG. 37B and a distal retention element, according to another embodiment.

FIGS. 37B and 37C, illustrate an alternative embodiment of a multi-lumen tube member 1103 that can be used with a distal retention element 1186 as shown in FIG. 37B, or a distal retention element 1286 as shown in FIG. 37C. The distal retention elements 1186 and 1286 can be disposed abutting a distal end of the multi-lumen tube member 1103 and can define at least in part a recess area to receive the loop ends of the actuation wires, and can provide increased overall strength and durability to the multi-lumen tube member 1103 during delivery and deployment of the prosthetic valve. The distal retention element 1186, 1286 can be formed with the same or a different material as the multi-lumen tube member 1103. In some embodiments, in may be desirable for the distal retention element 1186, 1286 to be formed of a material having greater strength characteristics than the multi-lumen tube member 1103. For example, the distal retention element 1186, 1286 can be formed with a metal or rigid plastic.

As shown in FIGS. 37B and 37C, the multi-lumen tube member 1103 (also referred to herein as "tube member") can define a center lumen 1180 and multiple pinning member lumens, including pinning member lumens 1179-3 and 1179-4 (collectively referred to as 1179) shown in FIGS. 37B and 37C that can receive therein pinning members, such as pinning members 1078-3 and 1078-4, respectively. Although not show, the tube member 1103 can also define pinning member lumens that can receive pinning members 1078-1 and 1078-2 as shown for tube member 1003 in FIG. 36.

As shown in FIG. 37B, the distal retention element 1186 can be received within the lumen 1180 and can define a lumen 1187 through which the valve holder 1038 can be slidably received. Although not shown, the distal retention element 1186 can be coupled to the tube member 1103 using various different coupling methods. For example, in some embodiments, the distal retention element 1186 can be bonded to the tube member 1103. In some embodiments the distal retention element 1186 can include a feature(s), such as barbs, that allow it to be inserted into the tube member 1103, but not removed. In some embodiments the distal retention element 1186 can include notches that interlock with a corresponding feature o the tube member 1103 and/or the tube member 1103 can be reflowed or molded over the retention element 1186. Various other coupling methods and/or combinations of securement strategies could be used to couple the distal retention element 1186 to the tube member 1103. In some embodiments, the distal retention element 1186 can extend proximally within the lumen 1180 of the tube member 1103 and be coupled at a proximal end portion of the tube member 1103.

The distal retention element 1186 also defines pinning member lumens 1169 that align with the pinning member lumens 1179 of the multi-lumen tube member 1103 such that the pinning members 1078 can be received therein. A proximal shoulder 1188 can be disposed abutting a distal end of the multi-lumen tube member 1103. The distal retention element 1186 also defines a circumferential recess area 1184 defined between the proximal shoulder 1188 and a distal end portion of the distal retention element 1186. As shown in FIG. 37B, the loop ends of the actuation wires 1074-1077 can be received within the recess area 1184 and pinned by the pinning members 1078 as described above for multi-lumen tube member 1003.

FIG. 37C illustrates a distal retention element 1286 disposed abutting the distal end of the multi-lumen tube member 1103. As with the previous embodiment, the distal retention element 1286 can be received within the lumen 1180 and can define a lumen 1287 through which the valve holder 1038 can be slidably received. The distal retention element 1286 can be coupled to the tube member 1103 in the same manner as described above for distal retention element 1186. The distal retention element 1286 also includes a proximal shoulder 1288 configured to abut the distal end of the multi-lumen tube member 1103. The distal retention element 1286 also defines a circumferential recess area 1284 that can receive the loop ends of actuation wires 1074"-1077", which can be pinned by the pinning members 1078 (1078-3 and 1078-4 shown in FIG. 37C). In this example, the actuation wires are configured as a closed loop as shown for actuation wire 1074" in FIG. 38C.

Figure 39:
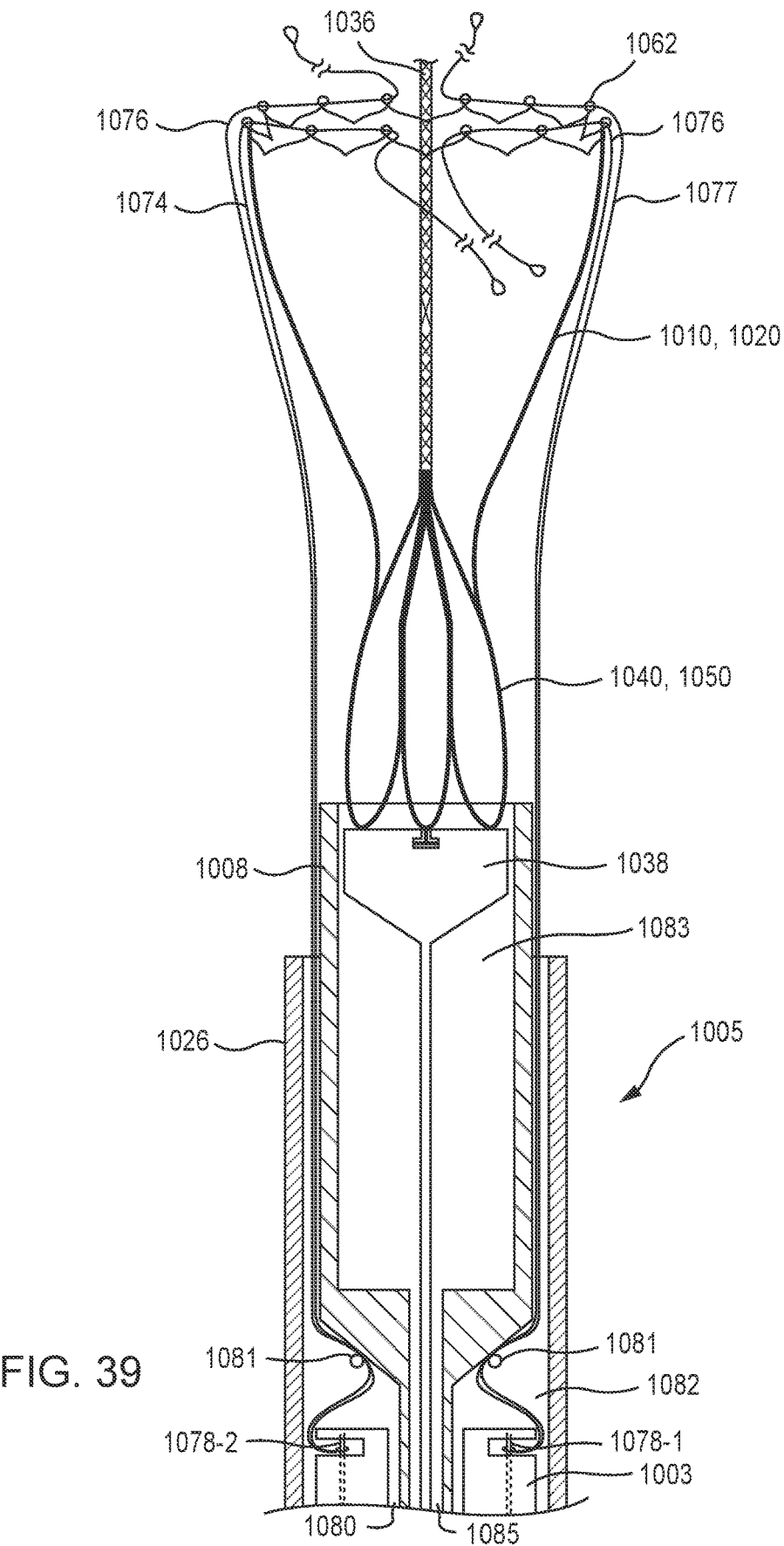
FIG. 39 is a partial cross-sectional side view of the delivery system and prosthetic heart valve of FIG. 34, shown in a first partially deployed configuration.

The procedure to deliver the valve 1000 to the heart can be the same as or similar to any of the procedures described herein, in '572 PCT Application and/or the '305 PCT Application incorporated by reference above. For example, the valve 1000, disposed within the delivery system 1005 in an inverted configuration, can be delivered to the left atrium of the heart in the same or similar manner as described herein with respect to other embodiments and/or with reference to FIGS. 43-48 of the '305 PCT Application. With the distal end portion of the delivery sheath 1026 disposed within the left atrium of the heart, the valve 1000 can be deployed outside of the delivery sheath 1026. For example, as shown in FIG. 39, the inner sheath 1008, valve holder 1038 and tube member 1003 can be moved distally relative to the outer sheath 1026, moving or pushing the valve 1000 outside the lumen 1082 of the outer sheath 1026. In addition, or alternatively, the outer sheath 1026 can be moved or pulled proximally, leaving at least a portion of the valve 1000 disposed within the heart. In some cases, the tether 1036 coupled to the valve 1000 can be used to help pull the valve 1000 out of the lumen of the outer sheath 1026.

As described above for previous embodiments, as the outer frame 1020 becomes unconstrained by the outer sheath 1026, the outer frame 1020 can begin to revert to its expanded or uninverted configuration. The actuation wires 1075-1077 can be used to control the reversion of the outer frame 1020. More specifically, the tube member 1003 can be pulled proximally such that the actuation wires (pinned to the tube member 1003) pull the distally disposed portion of the outer frame 1020 proximally (as shown in FIG. 40) in a controlled manner and such that the reversion of the outer frame 1020 from its inverted configuration relative to the inner frame 1050 can be controlled.

In addition, in some instances, the actuation wires 1074-1077 can assist in the articulation and placement of the valve 1000 into its destination (e.g., a native annulus of an atrioventricular valve of a heart). For example, as shown in FIG. 41, the actuation wires 1074-1077 can also be used to constrain, collapse, or otherwise move the valve 1000 (e.g., radially compress the outer frame 1020 of the valve 1000) after the valve 1000 exits the outer sheath 1026 and is in its reverted, expanded or partially expanded configuration. More specifically, in this embodiment, the tube member 1003 with the actuation wires 1074-1077 pinned thereto, can be manipulated by a user to move or urge the outer frame to a more compressed configuration (as shown in FIG. 41) by pulling or moving the tube member 1003 proximally. This may be desirable, for example, to reposition the valve 1000 within the heart before fully deploying the valve 1000.

Referring back to FIG. 40, when the outer frame 1020 of the valve 1000 is disposed in its non-inverted and at least partially expanded configuration, and is in a desired positon within the heart, the inner frame 1050 can be deployed. As described above for valve 400, to decouple the inner frame 1050 from the valve holder 1038, the valve holder 1038 can be moved distally and/or the inner sheath 1008 can be moved proximally such that the valve holder 1038 is disposed outside of the lumen 1083 of the inner sheath 1008. As such, the couplers 1006 can be released from the recesses 1004 releasing or decoupling the inner frame 1050 from the valve holder 1038. In some embodiments, the tether 1036 can be pulled to help move the inner frame 1050 outside of the inner sheath 1008. When the inner frame 1050 is released from the valve holder 1038 and disposed outside the inner sheath 1008, the inner frame 1050 can assume its biased expanded configuration.

Figure 42:
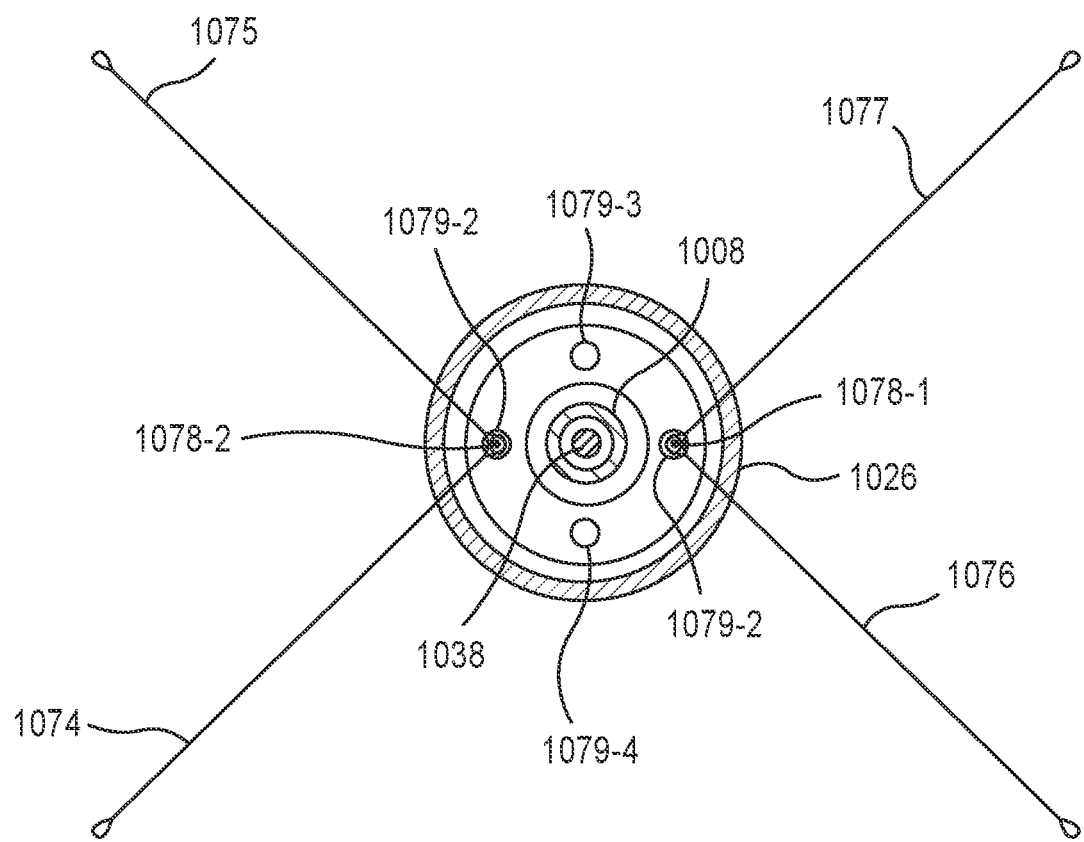
FIG. 42 is a cross-sectional view taken along line A-A in FIG. 34 showing the actuation wires in a partially released position.

The actuation wires 1074-1077 can also be released or decoupled from the outer frame 1020 before or after the inner frame 1050 is released form the valve holder 1038. To decouple the actuation wires 1074-1077 from the outer frame 1020, one end of each of the actuation wires 1074-1077 can be unpinned or decoupled from the tubular member 1003. For example, as shown in FIG. 42, the pinning member 1078-3 (See FIG. 35) can be withdrawn proximally from groove 1084 such that the second end of the actuation wire 1077 and the second end of the actuation wire 1075 are each released or unpinned from the tube member 1003, but remain pinned by pinning members 1078-2 and 1078-1, respectively. Similarly, the pinning member 1078-4 (see FIG. 35) can be withdrawn proximally from groove 1084 such that the second end of the actuation wire 1074 and the second end of actuation wire 1076 can each be released or unpinned from the tube member 1003, but remain pinned by pinning members 1078-2 and 1078-1, respectively. With one end of each of the actuation wires 1075-1077 coupled to the tube member 1003 (via pinning members 1078-1 and 1078-2 in this example), the tube member 1003 can be pulled proximally, which in turn will pull the opposite ends of the actuation wires 1074-1077 out of the loops 1062 of outer frame 1020. Thus with the actuation wires 1074-1077 detached from the outer frame 1020, the outer frame can assume a biased expanded or partially expanded configuration.

Although in the above example, the pinning members 1078-3 and 1078-4 are shown withdrawn to release the ends of the actuation wires 1074-1077, alternatively, the pinning members 1078-1 and 1078-2 can be withdrawn leaving the actuation wires 1074-1077 pinned by pinning members 1078-3 and 1078-4. Further, the actuation wires 1074-1077 can be decoupled from the outer frame 1020 at any suitable sequence or time period within the procedure. For example, in some instances it may be desirable for the actuation wires 1074-1077 to be released after the valve 1000 has at least partially exited the delivery sheath 1026 but before the valve 1000 is seated within the native annulus of the atrioventricular valve. In other instances, for example, the actuation wires 1074-1077 can be released after the valve 1000 has at least partially exited the outer delivery sheath 1026 and after the valve 1000 is seated within the native annulus of the atrioventricular valve.

Figure 43:
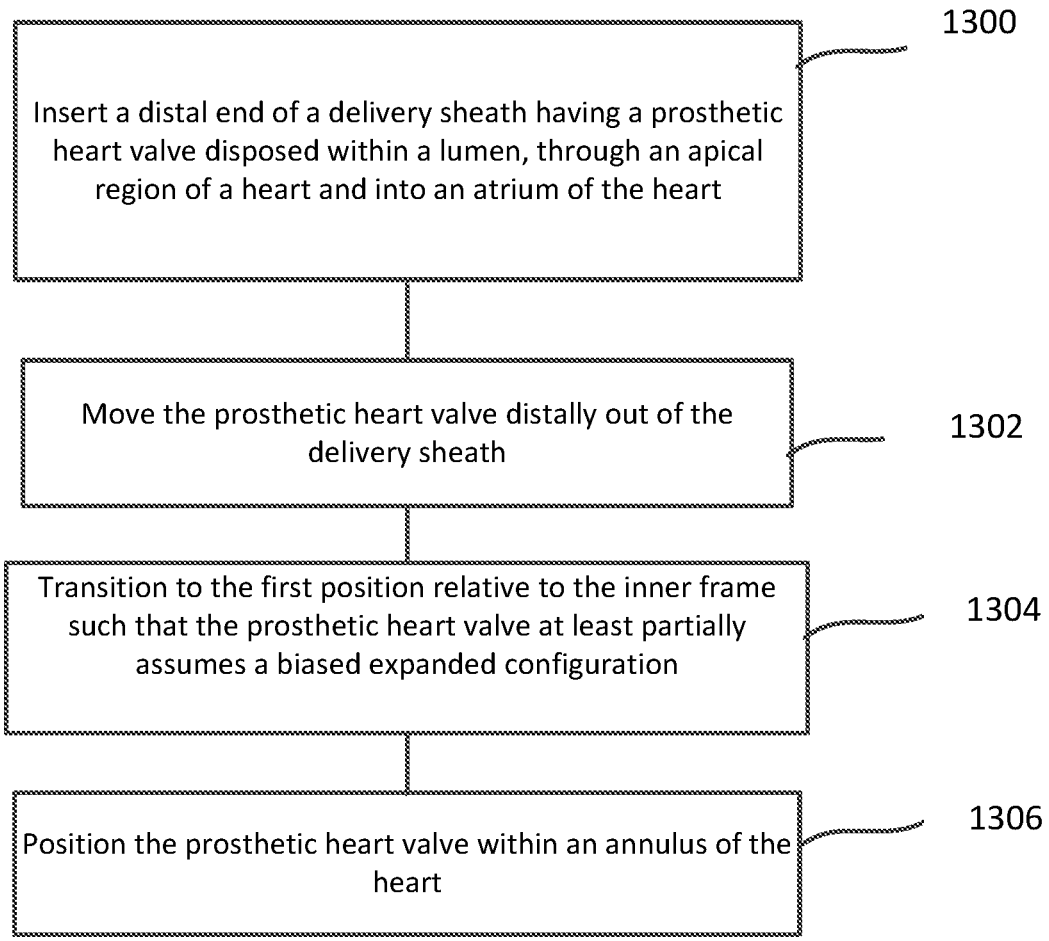
FIG. 43 is a flowchart illustrating a method of delivering and deploying a prosthetic valve within a heart, according to an embodiment.

FIG. 43 is a flowchart illustrating a method of delivering and deploying a prosthetic valve within a heart. The method includes at 1300, inserting a distal end of a delivery sheath through an apical region of a heart and into an atrium of the heart. The delivery sheath has a prosthetic heart valve disposed within a lumen of the delivery sheath. The prosthetic heart valve includes an outer frame and an inner frame coupled to the outer frame. The outer frame is movable between a first position relative to the inner frame and a second position relative to the inner frame in which the outer frame is inverted relative to the inner frame. The prosthetic valve is disposed within the lumen of the delivery sheath with the outer frame in the second position relative to the inner frame during the inserting. At 1302, the prosthetic heart valve is moved distally out of the delivery sheath. At 1304, the outer frame of the prosthetic heart valve is transitioned to the first position relative to the inner frame such that the prosthetic heart valve at least partially assumes a biased expanded configuration. At 1306, the prosthetic heart valve is positioned within an annulus of the heart.

Figure 44:
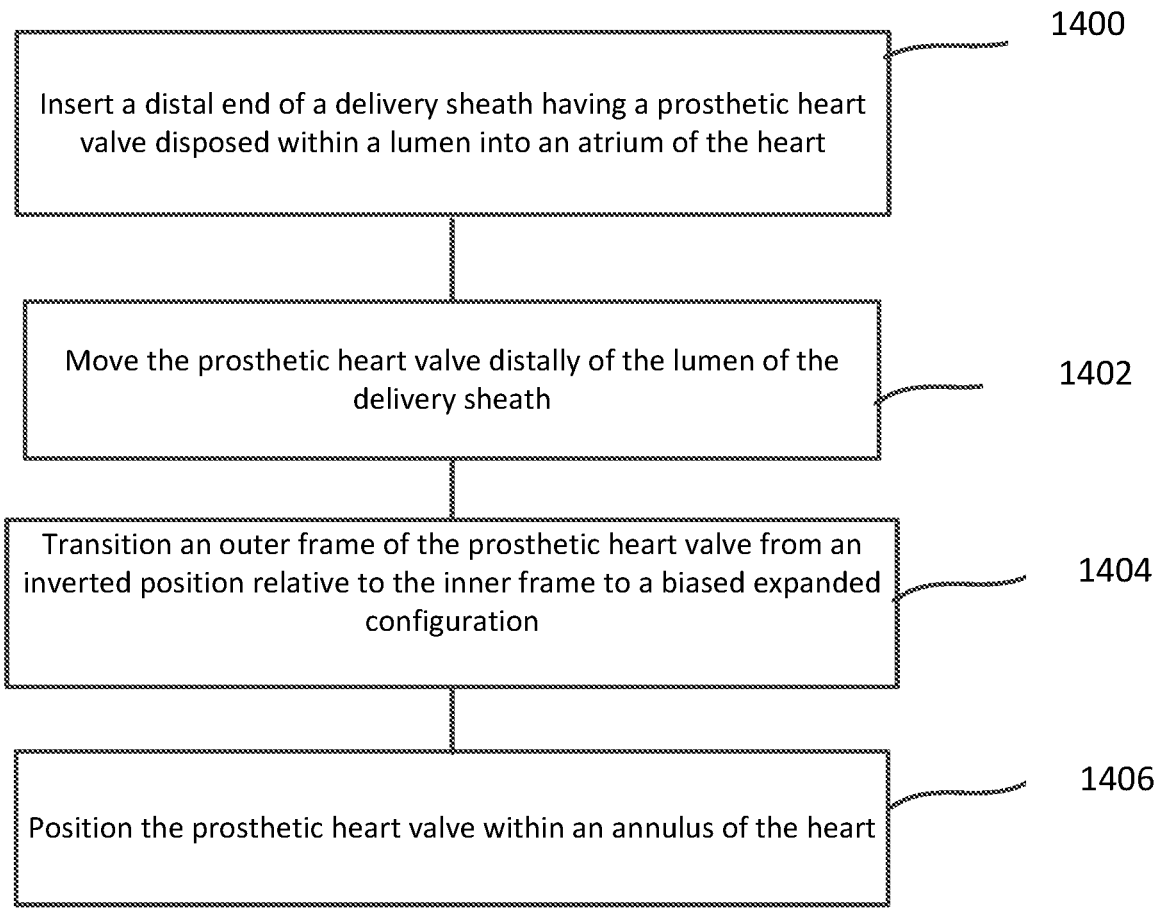
FIG. 44 is a flowchart illustrating a method of delivering and deploying a prosthetic valve within a heart, according to an embodiment.

FIG. 44 is a flowchart illustrating a method of delivering and deploying a prosthetic valve within a heart. At 1400 a distal end portion of a delivery sheath is inserted into an atrium of a heart. The delivery sheath has a prosthetic heart valve disposed within a lumen of the delivery sheath. The prosthetic heart valve includes an outer frame and an inner frame coupled to the outer frame. The outer frame is movable between a first position relative to the inner frame and a second position relative to the inner frame in which the outer frame is inverted relative to the inner frame. The prosthetic heart valve is disposed within the lumen of the delivery sheath with the outer frame in the second position relative to the inner frame and disposed at least partially axially proximal to the inner frame during the inserting. At 1402, the prosthetic heart valve is moved distally out of the delivery sheath. At 1404 the outer frame of the prosthetic heart valve is transitioned to the first position relative to the inner frame such that the prosthetic heart valve at least partially assumes a biased expanded configuration. At 1406, the prosthetic heart valve is positioned within an annulus of the heart.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

For example, although not specifically described for each embodiment, any of the embodiments of a delivery system can include a dilator device or member such as balloon dilator member. Further, the prosthetic heart valves described herein can be secured to a heart using an epicardial pad device as described with respect to FIGS. 43-48 and 72 of the '305 PCT Application. Moreover, although not shown for each embodiment, any of the embodiments of a delivery device or system can include a valve holder or valve pusher configured to urge the valve out the distal end of the delivery sheath during delivery of the valve.

Further, although not shown, any of the embodiments of a delivery device or system can include a handle or handle assembly to which the various delivery sheaths and components can be operatively coupled and which a user (e.g., physician) can grasp and use to manipulate the delivery device or system.

In addition, the systems and methods described herein can also be adapted for use with a prosthetic tricuspid valve. For example, in such a case, a procedural catheter can be inserted into the right ventricle of the heart, and the delivery sheath delivered to the right atrium of the heart either directly (transatrial), or via the jugular or femoral vein.

In addition, the systems and methods described herein can also be adapted for use with a prosthetic tricuspid valve. For example, in such a case, a delivery sheath can be delivered to the heart transapically.

The invention claimed is:

1. A method of delivering a prosthetic heart valve to an annulus of a heart, the method comprising:
    inserting a distal end portion of a delivery sheath into an atrium of the heart, the delivery sheath having the prosthetic heart valve disposed within a lumen of the delivery sheath, the prosthetic heart valve including an outer frame and an inner frame coupled to the outer frame, the outer frame being disposed distal to the inner frame when the prosthetic heart valve is disposed within the lumen of the delivery sheath;
    moving the prosthetic heart valve distally out of the delivery sheath so that the outer frame begins to deploy from the delivery sheath prior to the inner frame deploying from the delivery sheath;
    causing the outer frame of the prosthetic heart valve to begin to transition from an inverted position in which the outer frame is disposed distal to the inner frame to a reverted position in which the outer frame at least partially surrounds the inner frame; and
    positioning the prosthetic heart valve within the annulus of the heart,
    wherein as the prosthetic heart valve transitions from the inverted position to the reverted position,
    couplers of the inner frame are received within recesses of a valve holder within the delivery sheath to prevent the inner frame from moving axially relative to the valve holder;
    wherein causing the outer frame of the prosthetic heart valve to begin to transition from the inverted position to the reverted position includes pulling an actuation wire coupled to the outer frame in a proximal direction while the couplers of the inner frame are received within the recesses of the valve holder.

2. The method of claim 1, wherein the couplers of the inner frame are "T"-shaped.

3. The method of claim 1, further comprising:
    after causing the outer frame of the prosthetic heart valve to begin to transition from the inverted position to the reverted position, fully deploying the inner frame from the delivery sheath.

4. The method of claim 3, wherein an inner diameter of the delivery sheath is sized such that, when the valve holder and the prosthetic heart valve are disposed therein, the couplers are unable to exit the recesses.

5. The method of claim 4, wherein fully deploying the inner frame from the delivery sheath includes allowing the couplers to exit the recesses of the valve holder when the recesses are positioned distal to the distal end portion of the delivery sheath.

6. The method of claim 1, wherein an inner sheath is movably positioned within the delivery sheath, and the valve holder is movably positioned within the inner sheath.

7. The method of claim 1, wherein the actuation wire includes a first actuation wire releasably coupled to a first portion of the outer frame, and a second actuation wire releasably coupled to a second portion of the outer frame.

8. The method of claim 7, wherein the first actuation wire is threaded circumferentially through a first group of loops on the first portion of the outer frame, and the second actuation wire is threaded circumferentially through a second group of loops on the second portion of the outer frame.

9. The method of claim 1, further comprising decoupling the actuation wire from the outer frame after the outer frame has transitioned to the reverted position.

10. The method of claim 9, wherein decoupling the actuation wire from the outer frame is performed while a portion of the prosthetic heart valve is still disposed within the delivery sheath.

11. The method of claim 9, wherein decoupling the actuation wire from the outer frame is performed after the prosthetic heart valve is seated within the annulus of the heart.

12. The method of claim 1, wherein inserting the distal end portion of the delivery sheath into the atrium of the heart includes piercing an atrial septum, and the atrium is a left atrium.

13. The method of claim 12, wherein the annulus of the heart is a mitral valve annulus.

14. The method of claim 1, wherein inserting the distal end portion of the delivery sheath into the atrium of the heart is performed via a transjugular or transfemoral approach.

15. The method of claim 14, wherein the atrium of the heart is a right atrium, and the annulus of the heart is a tricuspid valve annulus.

16. The method of claim 1, wherein the prosthetic heart valve includes a tether positioned within a tether coupling portion of the inner frame.

17. The method of claim 16, further comprising positioning the tether so that it passes through the annulus of the heart, through a ventricle of the heart, and out a puncture site at an apex of the heart.

18. The method of claim 17, wherein moving the prosthetic heart valve distally out of the delivery sheath is performed, at least in part, by pulling on the tether.

19. The method of claim 17, wherein moving the prosthetic heart valve distally out of the delivery sheath is performed, at least in part, by pushing with the valve holder while pulling on the tether.

* * * * *